(12) United States Patent
Agarwal et al.

(10) Patent No.: US 7,365,069 B2
(45) Date of Patent: Apr. 29, 2008

(54) PYRIMIDONE DERIVATIVES

(75) Inventors: Shiv Kumar Agarwal, Chennai (IN); Ravikumar Tadiparthi, Chennai (IN); Pawan Aggarwal, Chennai (IN); Savithiri Shivakumar, Chennai (IN); Debendranath Dey, Fremont, CA (US); Biswajit Nag, Union City, CA (US)

(73) Assignee: Bexel Pharmaceuticals Inc., Union City, CA (US)

( * ) Notice: Subject to any disclaimer, the term of this patent is extended or adjusted under 35 U.S.C. 154(b) by 324 days.

(21) Appl. No.: 10/827,368

(22) Filed: Apr. 20, 2004

(65) Prior Publication Data

US 2004/0259891 A1 Dec. 23, 2004

Related U.S. Application Data

(63) Continuation-in-part of application No. 10/409,045, filed on Apr. 9, 2003, now abandoned.

(30) Foreign Application Priority Data

Oct. 4, 2002 (IN) .......................... 266/MAS/2002

(51) Int. Cl.
*C07D 239/36* (2006.01)
*A61K 31/513* (2006.01)
(52) U.S. Cl. ............................ 514/235.8; 514/252.14; 514/252.18; 514/269; 544/122; 544/295; 544/319
(58) Field of Classification Search ................ 544/319, 544/122, 295; 514/269, 235.8, 252.18, 252.14
See application file for complete search history.

(56) References Cited

OTHER PUBLICATIONS

Robev, CAPLUS Abstract 88:22768, 1978.*
Briel et al., CAPLUS Abstract 104:148820, 1986.*
Yokoyama et al., CAPLUS Abstract 107:7151, 1987.*
Mukherjee et al., CAPLUS Abstract 128:308465, 1998.*
Ulrich, Chapter 4: Crystallization, Kirk-Othmer Encyclopedia of Chemical Technology, Aug. 2002.*
Vippagunta et al., Crystalline Solids, Advanced Drug Delivery Reviews, 48, pp. 3-26, 2001.*
Sharma et al., CAPLUS Abstract 123:313866, 1995.*
Mazumdar et al., CAPLUS Abstract 121:157595, 1994.*

* cited by examiner

*Primary Examiner*—Deepak Rao
(74) *Attorney, Agent, or Firm*—Oliff & Berridge, PLC

(57) ABSTRACT

The present invention relates to novel pyrimidones of the general formula (I), their derivatives, their analogs, their tautomeric forms, their stereoisomers, their polymorphs, their hydrates, their solvates, their pharmaceutically acceptable salts and pharmaceutically acceptable compositions containing them. The present invention more particularly novel pyrimidones of the general formula (I)

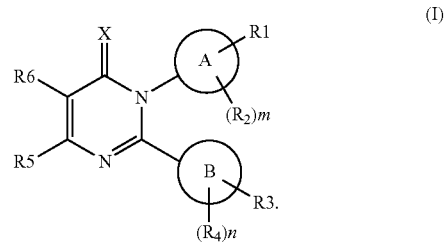

14 Claims, No Drawings

PYRIMIDONE DERIVATIVES

This is a Continuation-in-Part of application Ser. No. 10/409,045 filed Apr. 9, 2003 now abandoned. The entire disclosure of the prior application is hereby incorporated by reference herein in its entirety.

FIELD OF THE INVENTION

The present invention relates to novel pyrimidones of the general formula (I), their derivatives, their analogs, their tautomeric forms, their stereoisomers, their polymorphs, their hydrates, their solvates, their pharmaceutically acceptable salts and pharmaceutically acceptable compositions containing them. The present invention more particularly novel pyrimidones of the general formula (I).

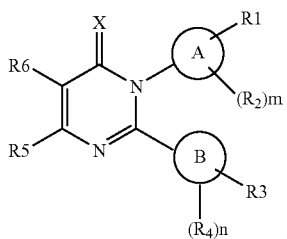

The present invention also provides a process for the preparation of the above said novel pyrimidones of the formula (I) pharmaceutically acceptable salts, their derivatives, their analogs, their tautomeric forms, their stereoisomers, their polymorphs, their hydrates, their solvates, their pharmaceutically acceptable salts, and pharmaceutical compositions containing them.

The novel pyrimidones of the present invention are useful for the treatment of inflammation and immunological diseases. Particularly the compounds of the present invention are useful for the treatment of inflammation and immunological diseases those mediated by cytokines such as TNF-α, IL-1, IL-6, IL-1β, IL-8 and cyclooxygenase such as COX-2 and COX-3. The compounds of the present invention are also useful for the treatment rheumatoid arthritis; osteoporosis; multiple myeloma; uveitis; acute and chronic myelogenous leukemia; ischemic heart disease; atherosclerosis; cancer; ischemic-induced cell damage; pancreatic β cell destruction; osteoarthritis; rheumatoid spondylitis; gouty arthritis; inflammatory bowel disease; adult respiratory distress syndrome (ARDS); psoriasis; Crohin's disease; allergic rhinitis; ulcerative colitis; anaphylaxis; contact dermatitis; asthma; muscle degeneration; cachexia; type I and type II diabetes; bone resorption diseases; ischemia reperfusion injury; atherosclerosis; brain trauma; multiple sclerosis; cerebral malaria; sepsis; septic shock; toxic shock syndrome; fever, and myalgias due to infection; and diseases mediated by HIV-1; HIV-2; HIV-3; *cytomegalovirus* (CMV); influenza; adenovirus; the herpes viruses (including HSV-1, HSV-2) and herpes zoster viruses.

BACKGROUND OF INVENTION

It has been reported that Cyclooxygenase enzyme exists in three isoforms, namely, COX-1, COX-2 and COX-3. COX-1 enzyme is essential and primarily responsible for the regulation of gastric fluids whereas COX-2 enzyme is present at the basal levels and is reported to have a major role in the prostaglandin synthesis for inflammatory response. These prostaglandins are known to cause inflammation in the body. Hence, if the synthesis of these prostaglandins is stopped by way of inhibiting COX-2 enzyme, inflammation and its related disorders can be treated. COX-3 possesses glycosylation-dependent cyclooxygenase activity. Comparison of canine COX-3 activity with murine COX-1 and COX-2 demonstrated that this enzyme is selectively inhibited by analgesic/antipyretic drugs such as acetaminophen, phenacetin, antipyrine, and dipyrone, and is potently inhibited by some nonsteroidal antiinflammatory drugs. Thus, inhibition of COX-3 could represent a primary central mechanism by which these drugs decrease pain and possibly fever. Recent reports show that inhibitors of COX-1 enzyme causes gastric ulcers, where as selective COX-2 and COX-3 enzyme inhibitors are devoid of this function and hence are found to be safe.

The present invention is concerned with treatment of immunological diseases or inflammation, notably such diseases are mediated by cytokines or cyclooxygenase. The principal elements of the immune system are macrophages or antigen-presenting cells, T cells and B cells. The role of other immune cells such as NK cells, basophils, mast cells and dendritic cells are known, but their role in primary immunologic disorders is uncertain. Macrophages are important mediators of both inflammation and providing the necessary "help" for T cell stimulation and proliferation. Most importantly macrophages make IL-1, IL-12 and TNF-α all of which are potent proinflammatory molecules and also provide help for T cells. In addition, activation of macrophages results in the induction of enzymes, such as cyclooxygenase-2 (COX-2) and cyclooxygenase-3 (COX-3), inducible nitric oxide synthase (iNOS) and production of free radicals capable of damaging normal cells. Many factors activate macrophages, including bacterial products, superantigens and interferon gamma (IFNγ). It is believed that phosphotyrosine kinases (PTKs) and other undefined cellular kinases are involved in the activation process.

Cytokines are molecules secreted by immune cells that are important in mediating immune responses. Cytokine production may lead to the secretion of other cytokines, altered cellular function, cell division or differentiation. Inflammation is the body's normal response to injury or infection. However, in inflammatory diseases such as rheumatoid arthritis, pathologic inflammatory processes can lead to morbidity and mortality. The cytokine tumor necrosis factor-alpha (TNF-α) plays a central role in the inflammatory response and has been targeted as a point of intervention in inflammatory disease. TNF-α is a polypeptide hormone released by activated macrophages and other cells. At low concentrations, TNF-α participates in the protective inflammatory response by activating leukocytes and promoting their migration to extravascular sites of inflammation (Moser et al., J Clin Invest, 83, 444-55, 1989). At higher concentrations, TNF-α can act as a potent pyrogen and induce the production of other pro-inflammatory cytokines (Haworth et al., Eur J Immunol, 21, 2575-79, 1991; Brennan et al., Lancet, 2, 244-7, 1989). TNF-α also stimulates the synthesis of acute-phase proteins. In rheumatoid arthritis, a chronic and progressive inflammatory disease affecting about 1% of the adult U.S. population, TNF-α mediates the cytokine cascade that leads to joint damage and destruction (Arend et al., Arthritis Rheum, 38, 151-60, 1995). Inhibitors of TNF-α, including soluble TNF receptors (etanercept) (Goldenberg, Clin Ther, 21, 75-87, 1999) and anti-TNF-α antibody (infliximab) (Luong et al., Ann Pharmacother, 34, 743-60, 2000), have recently been approved by the U.S.

Food and Drug Administration (FDA) as agents for the treatment of rheumatoid arthritis.

Elevated levels of TNF-α have also been implicated in many other disorders and disease conditions, including cachexia, septic shock syndrome, osteoarthritis, inflammatory bowel disease such as Crohn's disease and ulcerative colitis etc.

Elevated levels of TNF-α and/or IL-1 over basal levels have been implicated in mediating or exacerbating a number of disease states including rheumatoid arthritis; osteoporosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; type I and type II diabetes; bone resorption diseases; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, *cytomegalovirus* (CMV), influenza, adenovirus, the herpes viruses (including HSV-1, HSV-2), and herpes zoster are also exacerbated by TNF-α.

It can be seen that inhibitors of TNF-α are potentially useful in the treatment of a wide variety of diseases. Compounds that inhibit TNF-α have been described in several patents.

Excessive production of IL-6 is implicated in several disease states, it is highly desirable to develop compounds that inhibit IL-6 secretion. Compounds that inhibit IL-6 have been described in U.S. Pat. Nos. 6,004,813; 5,527,546 and 5,166,137.

The cytokine IL-1β also participates in the inflammatory response. It stimulates thymocyte proliferation, fibroblast growth factor activity, and the release of prostaglandin from synovial cells. Elevated or unregulated levels of the cytokine IL-1 have been associated with a number of inflammatory diseases and other disease states, including but not limited to adult respiratory distress syndrome, allergy, Alzheimer's disease etc. Since overproduction of IL-1β is associated with numerous disease conditions, it is desirable to develop compounds that inhibit the production or activity of IL-1β.

In rheumatoid arthritis models in animals, multiple intra-articular injections of IL-1 have led to an acute and destructive form of arthritis (Chandrasekhar et al., Clinical Immunol Immunopathol. 55, 382, 1990). In studies using cultured rheumatoid synovial cells, IL-1 is a more potent inducer of stromelysin than TNF-α. (Firestein, Am. J. Pathol. 140, 1309, 1992). At sites of local injection, neutrophil, lymphocyte, and monocyte emigration has been observed. The emigration is attributed to the induction of chemokines (e.g., IL-8), and the up-regulation of adhesion molecules (Dinarello, Eur. Cytokine Netw. 5, 517-531, 1994).

In rheumatoid arthritis, both IL-1β and TNF-α induce synoviocytes and chondrocytes to produce collagenase and neutral proteases, which leads to tissue destruction within the arthritic joints. In a model of arthritis (collagen-induced arthritis (CIA) in rats and mice) intra-articular administration of TNF-α either prior to or after the induction of CIA led to an accelerated onset of arthritis and a more severe course of the disease (Brahn et al., Lymphokine Cytokine Res. 11, 253, 1992; and Cooper, Clin. Exp. Immunol. 898, 244, 1992).

IL-8 has been implicated in exacerbating and/or causing many disease states in which massive neutrophil in filtration into sites of inflammation or injury (e.g., ischemia) is mediated chemotactic nature of IL-8, including, but not limited to, the following: asthma, inflammatory bowl disease, psoriasis, adult respiratory distress syndrome, cardiac and renal reperfusion injury, thrombosis and glomerulonephritis. In addition to the chemotaxis effect on neutrophils, IL-8 has also has ability to activate neutrophils. Thus, reduction in IL-8 levels may lead to diminished neutrophil infiltration.

Few prior art references, which disclose the closest compounds, are given here:

i) U.S. Pat. Nos. 5,726,124 and 5,300,477 disclose novel herbicidal compounds of formula (IIa)

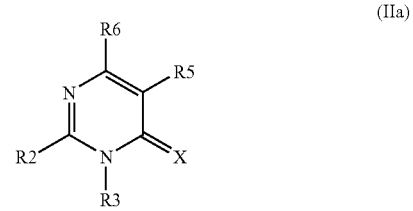

(IIa)

$R_2$ is a substituted or unsubstituted aryl group or a substituted or unsubstituted heteroaromatic group (e.g. a heteroaromatic ring structure having four to five carbon atoms and one heteroatom selected from the group consisting of nitrogen, sulfur and oxygen); $R_3$ is an alkyl, haloalkyl, polyhaloalkyl, haloalkenyl, polyhaloalkenyl, alkenyl, alkynyl, haloalkynyl, polyhaloalkynyl, alkoxyalkyl, dialkoxyalkyl, haloalkoxyalkyl, oxoalkyl, trimethylsilylalkynyl, cyanoalkyl or aryl group; $R_5$ is a hydrogen, halo, acyl, alkyl, alkenyl, alkynyl, alkoxy, alkylthio, alkoxyalkyl, alkoxyimino, alkoxycarbonylalkyl, dialkoxyalkyl, formyl, haloalkyl, haloalkenyl, haloalkynyl, haloalkoxy, hydroxyalkyl, hydroxyimino, polyhaloalkyl, polyhaloalkenyl, polyhaloalkynyl, polyhaloalkoxy, trimethylsilylalkynyl, alkoxyalkoxy, aminocarbonylalkyl, alkylaminocarbonylalkyl, dialkylaminocarbonylalkyl, cyanoalkyl, hydroxy or cyano group; and $R_6$ is a hydrogen, halo, alkyl, alkenyl, alkynyl, alkoxy, alkylthio, alkoxyalkyl, alkoxycarbonyl, alkoxycarbonylalkyl, haloalkyl, haloalkenyl, haloalkynyl, haloalkoxy, haloalkylthio, polyhaloalkyl, polyhaloalkenyl, polyhaloalkynyl, polyhaloalkoxy, polyhaloalkylthio, cycloalkyl, aryl, aryloxy, heterocyclyl, aralkyl, alkylamino, dialkylamino, dialkylaminocarbonyl, or cyano group; and X is oxygen or sulfur.

An example of these compounds is shown in formula (IIb)

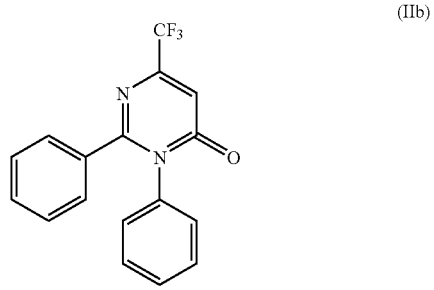

(IIb)

ii) U.S. Pat. No. 5,474,996 discloses novel compounds of formula (IIc)

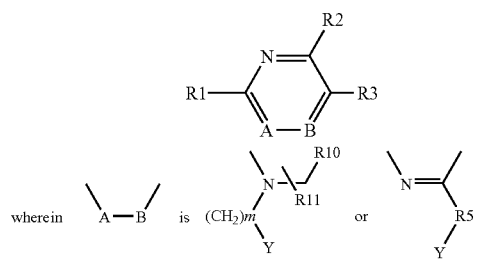

$R_5$ is a single bond or —$(CH_2)_m$—, —NH—, etc., m is an integer of 0 to 4; Y is $Y_1$-B-$Y_2$ is a monocyclic aryl of 5 to 6 ring member or condensed ring of 8 to 10 ring members optionally containing at least one heteroatom chosen from oxygen, nitrogen and sulfur; $R_{10}$ and $R_{11}$ together form oxo group; $R_2$ is chosen from the group consisting of hydrogen, halogen, hydroxyl, mercapto, cyano, nitro, formyl, benzoyl, acyl of 1 to 6 carbon atoms, alkyl, alkenyl, alkoxy, alkylthio of up to 10 carbon atoms, phenyl, phenoxy, naphthyl, benzyl, phenylthio, biphenyl, biphenylmethyl and indole; $R_3$ is alkyl substituted with carboxy or esterified carboxy.

An example of these compounds is shown in formula (IId)

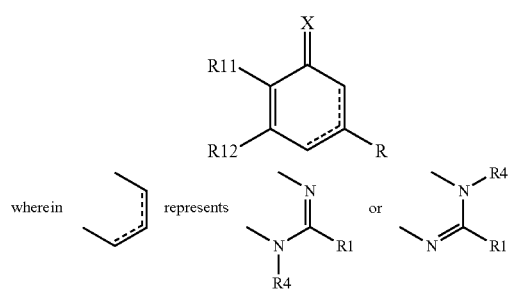

iii) U.S. Pat. Nos. 6,420,385 and 6,410,729 discloses novel compounds of formula (IIe)

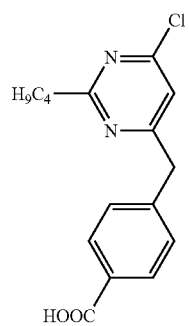

X is O, S or $NR_5$; $R_1$ and $R_2$ are each independently represent —Y or —Z—Y, and $R_3$ and $R_4$ are each independently —Z—Y or $R_3$ is a hydrogen radical; provided that $R_4$ is other than a substituted-aryl, (substituted-aryl)methyl or (substituted-aryl)ethyl radical; wherein each Z is independently optionally substituted alkyl, alkenyl, alkynyl, heterocyclyl, aryl or heteroaryl; Y is independently a hydrogen; halo, cyano, nitro, etc., $R_5$ is independently a hydrogen, optionally substituted alkyl, alkenyl, alkynyl etc., $R_{11}$ and $R_{12}$ each independently represent optionally substituted aryl or heteroaryl.

An example of these compounds is shown in formula (IIf)

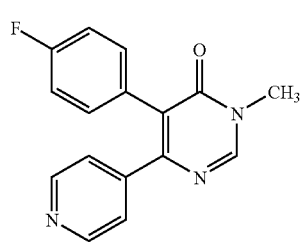

iv) U.S. Pat. No. 4,771,040 discloses 6-oxopyrimidinyl (thiono)phosphate pesticide compounds and intermediate of formula (IIg)

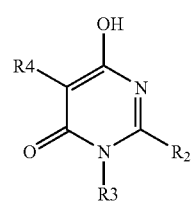

wherein $R_2$ represents hydrogen, optionally substituted alkyl, or alkoxy, alkylthio, dialkylamino or aryl; $R_3$ represents alkyl or aryl; $R_4$ represents hydrogen, halogen or alkyl.

An example of these compounds is shown in formula (IIh)

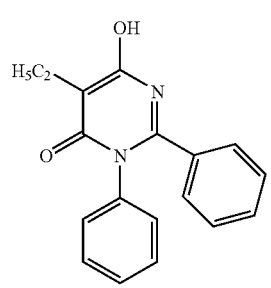

v) DE 2142317 discloses hypnotic uracil derivatives of formula (IIi)

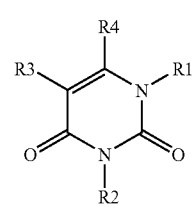

wherein R₁ is H, alkyl, alkenyl, dialkylaminoalkyl, or aralkyl; R₂ is H, alkyl, aryl, or halogen; R₃ is alkyl, alkenyl, cycloalkyl, aralkyl, aralkenyl, or aryl, R₄ is alkyl, alkenyl, cycloalkyl, aralkyl, aryl, etc.

An example of these compounds is shown in formula (IIj)

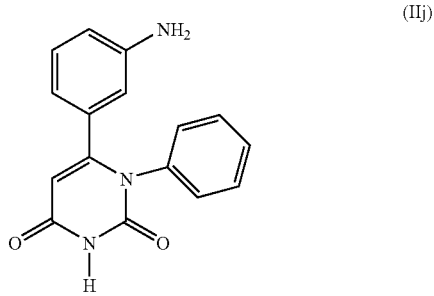

vi) U.S. Pat. No. 5,470,975 discloses dihydropyrimidine derivatives of formula (IIk)

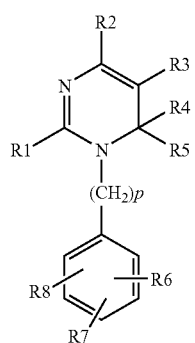

R₁ is alkyl, alkenyl, alkynyl, cycloalkyl, NR₄R₅ etc., R₂ is hydrogen, halogen, SR₄, etc., R₃ is R₄, —COOR, —CONH₂, CN, etc., R₄, R₅ are independently selected from hydrogen, alkyl, alkenyl, alkynyl, aryl, arylalkyl, cycloalkyl etc., or R₄ and R₅ together with the carbon atoms to which they are attached form a carbonyl or a thiocarbonyl group; R₆ is —CN, alkyl, acyloxy, SO₂NH₂, aryl, furyl; R₇ is H, halogen, etc., R₈ is H, halogen, alkyl, alkoxy etc., An example of these compounds is shown in formula (III)

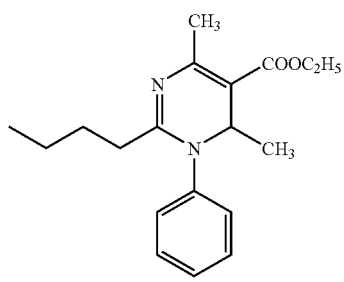

OBJECTIVE OF THE INVENTION

We have focused our research to identify selective COX-2 and COX-3 inhibitors which are devoid of any side effects normally associated with anti-inflammatory agents. Our sustained efforts have resulted in novel pyrimidones of the formula (I). The derivatives may be useful in the treatment of inflammation and immunological diseases. Particularly the compounds of the present invention are useful for the treatment of inflammation and immunological diseases those mediated by cytokines such as TNF-α, IL-1, IL-6, IL-1β, IL-8 and cyclooxygenase such as COX-2 and COX-3. The compounds of the present invention are also useful in the treatment of rheumatoid arthritis; osteoporosis; multiple myeloma; uveitis; acute and chronic myelogenous leukemia; ischemic heart disease; atherosclerosis; cancer; ischemic-induced cell damage; pancreatic β-cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; type I and type II diabetes; bone resorption diseases; ischemia reperfusion injury; atherosclerosis; brain trauma; multiple sclerosis; cerebral malaria; sepsis; septic shock; toxic shock syndrome; fever, and myalgias due to infection; and diseases mediated by HIV-1; HIV-2; HIV-3; *cytomegalovirus* (CMV); influenza; adenovirus; the herpes viruses (including HSV-1, HSV-2) and herpes zoster viruses.

SUMMARY OF THE INVENTION

The present invention relates to novel pyrimidones of the formula (I)

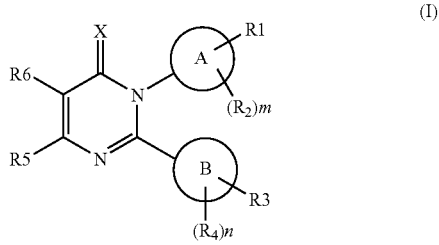

their derivatives, their analogs, their tautomeric forms, their stereoisomers, their polymorphs, and their pharmaceutically acceptable salts, wherein X represents oxygen, sulfur or NR, wherein R represents hydrogen, hydroxyl, acyl, alkyl, alkoxy, aryl, amino, hydroxylamino, alkylamino, arylamino, acylamino, alkoxyamino group; the rings represented by A and B are selected from aryl or heteroaryl; $R^1$ and $R^3$ may be same or different and independently represent hydrogen, $SR^7$, $S(O)_pR^8$; $R^2$ and $R^4$ may be same or different and independently represent hydrogen, halogen, hydroxyl, nitro, cyano, azido, nitroso, amino, formyl, alkyl, haloalkyl, acyl, alkoxy, monoalkylamino, dialkylamino, acylamino, alkoxycarbonyl, $SR^7$, $S(O)_pR^8$, alkoxyalkyl groups or carboxylic acids or its derivatives; $R^5$ and $R^6$ may be same or different and independently represent hydrogen, halogen, hydroxyl, nitro, cyano, azido, nitroso, amino, formyl, alkyl, aryl, aralkyl, haloalkyl, acyl, alkoxy, aryloxy, aralkoxy, heteroaryl, heterocyclyl, monoalkylamino, dialkylamino, acylamino, alkoxycarbonyl, $SR^7$, $S(O)_pR^8$, alkoxyalkyl groups or $COR^9$; $R^7$ represents hydrogen, alkyl or aryl; $R^8$ represents halogen, alkyl, amino, acylamino, arylamino or aryl group; $R^9$ represents hydrogen, hydroxyl, amino, halogen, alkyl, alkoxy, aryloxy, monoalkylamino, dialkylamino, acylamino, arylamino, groups; m is an integer and is in the range of 0 to 4; n is an integer and is in the range of 0 to 4; p represents an integer of 1 or 2; with a proviso that when $R^1$ represents hydrogen $R^2$ is not hydrogen.

DETAILED DESCRIPTION OF THE INVENTION

Suitable ring systems represented by A and B are selected from phenyl, naphthyl, pyrrolidinyl, morpholinyl, thiomorpholinyl, piperidinyl, piperazinyl, pyridyl, thienyl, furyl, pyrrolyl, oxazolyl, thiazolyl, imidazolyl, pyrazolyl, oxadiazolyl, thiadiazolyl, tetrazolyl, pyrimidinyl, benzopyranyl, benzofuranyl, benzimidazolyl, benzoxazolyl, benzothiazolyl, benzopyrrolyl, benzoxadiazolyl, benzothiadiazolyl, quinolinyl, isoquinolinyl, benzothienyl, benzofuranyl, indolyl and the like.

Suitable groups represented by $R^1$ and $R^3$ are selected from hydrogen, $SR^7$, or $S(O)_p R^8$, Suitable groups represented by $R^2$ and $R^4$ are selected from hydrogen, halogen atom such as fluorine, chlorine, bromine, iodine; hydroxyl, nitro, cyano, azido, nitroso, amino, formyl, linear or branched $(C_1-C_6)$ alkyl group, such as methyl, ethyl, n-propyl, isopropyl, n-butyl, isobutyl, t-butyl, n-pentyl, isopentyl, hexyl and the like; haloalkyl such as chloromethyl, chloroethyl, trifluoromethyl, trifluoroethyl, dichloromethyl, dichloroethyl and the like; acyl group such as —C(=O)CH$_3$, —C(=O)C$_2$H$_5$, —C(=O)C$_3$H$_7$, —C(=O)C$_6$H$_{13}$, —C(=S)CH$_3$, —C(=S)C$_2$H$_5$, —C(=S)C$_3$H$_7$, —C(=S)C$_6$H$_{13}$, benzoyl; linear or branched $(C_1-C_6)$ alkoxy group, such as methoxy, ethoxy, n-propoxy, isopropoxy and the like; monoalkylamino group such as NHCH$_3$, NHC$_2$H$_5$, NHC$_3$H$_7$, NHC$_6$H$_{13}$, and the like; dialkylamino group such as N(CH$_3$)$_2$, NCH$_3$(C$_2$H$_5$), N(C$_2$H$_5$)$_2$ and the like; acylamino group such as NHC(=O)CH$_3$, NHC(=O)C$_2$H$_5$, NHC(=O)C$_3$H$_7$, NHC(=O)C$_6$H$_{13}$, and the like; alkoxycarbonyl group such as methoxycarbonyl, ethoxycarbonyl, n-propoxycarbonyl, isopropoxycarbonyl and the like; alkoxyalkyl group such as methoxymethyl, ethoxymethyl, methoxyethyl, ethoxyethyl and the like; carboxylic acid or its derivatives such as esters, amides and acid halides, $SR^7$, or $S(O)_p R^8$.

Suitable groups represented by $R^5$ and $R^6$ are selected from hydrogen, halogen atom such as fluorine, chlorine, bromine, iodine; hydroxyl, nitro, cyano, azido, nitroso, amino, formyl, linear or branched $(C_1-C_6)$ alkyl group, such as methyl, ethyl, n-propyl, isopropyl, n-butyl, isobutyl, t-butyl, n-pentyl, isopentyl, hexyl and the like; haloalkyl such as wherein the alkyl is as defined above; aryl such as phenyl, naphthyl and the like; aralkyl such as benzyl, phenylethyl, phenylpropyl and the like; aryloxy group such as phenoxy, napthoxy and the like; aralkoxy group such as phenylmethoxy, phenylethoxy, phenylpropoxy, and the like; heteroaryl group such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, benzopyranyl, benzofuranyl, benzimidazolyl, benzoxazolyl, benzothiazolyl, benzopyrrolyl, benzoxadiazolyl, benzothiadiazolyl and the like; heterocyclyl group such as pyrrolidinyl, morpholinyl, thiomorpholinyl, piperidinyl, piperazinyl, and the like; acyl group such as —C(=O)CH$_3$, —C(=O)C$_2$H$_5$, —C(=O)C$_3$H$_7$, —C(=O)C$_6$H$_{13}$, —C(=S)CH$_3$, —C(=S)C$_2$H$_5$, —C(=S)C$_3$H$_7$, —C(=S)C$_6$H$_{13}$, benzoyl; linear or branched $(C_1-C_6)$ alkoxy group, such as methoxy, ethoxy, n-propoxy, isopropoxy and the like; monoalkylamino group such as NHCH$_3$, NHC$_2$H$_5$, NHC$_3$H$_7$, NHC$_6$H$_{13}$, and the like; dialkylamino group such as N(CH$_3$)$_2$, NCH$_3$(C$_2$H$_5$), N(C$_2$H$_5$)$_2$ and the like; acylamino group such as NHC(=O)CH$_3$, NHC(=O)C$_2$H$_5$, NHC(=O)C$_3$H$_7$, NHC(=O)C$_6$H$_{13}$, and the like; alkoxycarbonyl group such as methoxycarbonyl, ethoxycarbonyl, n-propoxycarbonyl, isopropoxycarbonyl and the like; alkoxyalkyl group such as methoxymethyl, ethoxymethyl, methoxyethyl, ethoxyethyl and the like or COR$^9$, SR$^7$, or S(O)$_p$R$^8$.

The groups represented by $R^5$ and $R^6$ may be substituted with the substituents selected from halogen, hydroxyl, nitro, cyano, azido, nitroso, amino, formyl, alkyl, aryl, aralkyl, haloalkyl, acyl, alkoxy, aryloxy, aralkoxy, heteroaryl, heterocyclyl, monoalkylamino, dialkylamino, acylamino, alkoxycarbonyl, alkylsulfonyl, alkylsulfinyl, alkylsulfanyl, sulfamoyl, alkoxyalkyl groups or carboxylic acids or its derivatives. The substituents are as defined above.

Suitable groups represented by $R^7$ are selected from hydrogen, linear or branched $(C_1-C_6)$alkyl group, such as methyl, ethyl, n-propyl, isopropyl, n-butyl, isobutyl, t-butyl, n-pentyl, isopentyl, hexyl and the like; aryl group such as phenyl or naphthyl.

Suitable groups represented by $R^8$ are selected from amino, halogen atom such as fluorine, chlorine, bromine, iodine; linear or branched $(C_1-C_6)$alkyl group, such as methyl, ethyl, n-propyl, isopropyl, n-butyl, isobutyl, t-butyl, n-pentyl, isopentyl, hexyl and the like; aryl group such as phenyl or naphthyl; arylamino such as phenyl amino, naphthyl amino and the like; acylamino group such as NHC(=O)CH$_3$, NHC(=O)C$_2$H$_5$, NHC(=O)C$_3$H$_7$, NHC(=O)C$_6$H$_{13}$, and the like.

Suitable groups represented by $R^9$ are selected from hydrogen, hydroxyl, amino, halogen atom such as fluorine, chlorine, bromine, iodine; linear or branched $(C_1-C_6)$alkyl group, such as methyl, ethyl, n-propyl, isopropyl, n-butyl, isobutyl, t-butyl, n-pentyl, isopentyl, hexyl and the like; linear or branched $(C_1-C_6)$ alkoxy group, such as methoxy, ethoxy, n-propoxy, isopropoxy and the like; monoalkylamino group such as NHCH$_3$, NHC$_2$H$_5$, NHC$_3$H$_7$, NHC$_6$H$_{13}$, and the like, which may be substituted; dialkylamino group such as N(CH$_3$)$_2$, NCH$_3$(C$_2$H$_5$), N(C$_2$H$_5$)$_2$ and the like; aryloxy group such as phenoxy, napthoxy and the like; arylamino such as phenyl amino, naphthyl amino and the like; acylamino group such as NHC(=O)CH$_3$, NHC(=O)C$_2$H$_5$, NHC(=O)C$_3$H$_7$, NHC(=O)C$_6$H$_{13}$, and the like.

Suitable groups represented by R are selected from hydrogen, hydroxyl, amino, hydroxylamino, linear or branched $(C_1-C_6)$alkyl group, such as methyl, ethyl, n-propyl, isopropyl, n-butyl, isobutyl, t-butyl, n-pentyl, isopentyl, hexyl and the like; linear or branched $(C_1-C_6)$ alkoxy group, such as methoxy, ethoxy, n-propoxy, isopropoxy and the like; aryl group such as phenyl, naphthyl and the like; acyl group such as —C(=O)CH$_3$, —C(=O)C$_2$H$_5$, —C(=O)C$_3$H$_7$, —C(=O)C$_6$H$_{13}$, —C(=S)CH$_3$, —C(=S)C$_2$H$_5$, —C(=S)C$_3$H$_7$, —C(=S)C$_6$H$_{13}$, benzoyl; aryl group such as phenyl or naphthyl; alkylamino group such as NHCH$_3$, NHC$_2$H$_5$, NHC$_3$H$_7$, NHC$_6$H$_{13}$, N(CH$_3$)$_2$, NCH$_3$(C$_2$H$_5$), N(C$_2$H$_5$)$_2$ and the like; acylamino group such as NHC(=O)CH$_3$, NHC(=O)C$_2$H$_5$, NHC(=O)C$_3$H$_7$, NHC(=O)C$_6$H$_{13}$, and the like; arylamino such as phenyl amino, naphthyl amino and the like; alkoxyamino such as methoxyamino, ethoxyamino, propoxy amino and the like.

m and n are integers ranging from 0-4.

Pharmaceutically acceptable salts of the present invention include alkali metal salts like Li, Na, and K salts, alkaline earth metal salts like Ca and Mg salts, salts of organic bases such as diethanolamine, α-phenylethylamine, benzylamine, piperidine, morpholine, pyridine, hydroxyethylpyrrolidine, hydroxyethylpiperidine, guanidine, choline and the like, ammonium or substituted ammonium salts, aluminum salts. Salts also include amino acid salts such as glycine, alanine, cystine, cysteine, lysine, arginine, phenylalanine etc. Salts may include sulphates, nitrates, phosphates, perchlorates, borates, hydrohalides, acetates, tartrates, maleates, citrates, succinates, palmoates, methanesulphonates, tosylates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Representative compounds according to the present invention include:

5-Cyano-2-(4-chlorophenyl)-4-(methylthio)-1-[4-(methylthio)phenyl]-6-oxo-1,6-dihydropyrimidine;
5-Cyano-2-(4-fluorophenyl)-4-(methylthio)-1-[4-(methylthio)phenyl]-6-oxo-1,6-dihydropyrimidine;
5-Cyano-2-phenyl-4-(methylthio)-1-[4-(methylthio)phenyl]-6-oxo-1,6-dihydropyrimidine;
5-Cyano-2-(trifluoromethylphenyl)-4-(methylthio)-1-[4-(methylthio)phenyl]-6-oxo-1,6-dihydropyrimidine;
5-Cyano-2-[(4-methylthio)phenyl]-4-(methylthio)-1-[4-fluorophenyl]-6-oxo-1,6-dihydropyrimidine;
5-Cyano-1-(4-methylphenyl)-4-(methylthio)-2-[4-(methylthio)phenyl]-6-oxo-1,6-dihydropyrimidine;
5-Cyano-2-[(4-methylsulfonyl)phenyl]-4-(methylthio) 1-[4-methylphenyl]-6-oxo-1,6-dihydropyrimidine;
5-Carboxy-2-[(4-methylthio)phenyl]-4-(methylthio)-1-[4-methylphenyl]-6-oxo-1,6-dihydropyrimidine;
5-Cyano-1-(4-isopropylphenyl)-4-(methylthio)-2-[4-(methylthio)phenyl]-6-oxo-1,6-dihydropyrimidine;
5-Cyano-1-(3,4-dimethylphenyl)-4-(methylthio)-2-[4-(methylthio)phenyl]-6-oxo-1,6-dihydropyrimidine;
5-Cyano-1-(4-isopropylphenyl)-2-[4-(methylsulfonyl)phenyl]-4-(methylthio)-6-oxo-1,6-dihydropyrimidine;
5-Cyano-1-(3,4-dimethylphenyl)-2-[4-(methylsulfonyl)phenyl]-4-(methylthio)-6-oxo-1,6-dihydropyrimidine;
5-Cyano-1-(3,4,5-trimethoxyphenyl)-4-(methylthio)-2-[4-(methylthio)phenyl]-6-oxo-1,6-dihydropyrimidine;
5-Cyano-1-(4-ethylphenyl)-4-(methylthio)-2-[4-(methylthio)phenyl]-6-oxo-1,6-dihydropyrimidine;
1-(4-Bromophenyl)-5-cyano-4-(methylthio)-2-[4-(methylthio)phenyl]-6-oxo-1,6-dihydropyrimidine;
5-Cyano-1-(4-methoxyphenyl)-4-(methylthio)-2-[4-(methylthio)phenyl]-6-oxo-1,6-dihydropyrimidine;
5-Cyano-1-(4-fluorophenyl)-4-(methylthio)-2-phenyl-6-oxo-1,6-dihydropyrimidine;
1-(4-Chlorophenyl)-5-cyano-4-(methylthio)-2-[4-(methylthio)phenyl]-6-oxo-1,6-dihydropyrimidine;
5-Cyano-1-(2,4-dimethylphenyl)-4-(methylthio)-2-[4-(methylthio)phenyl]-6-oxo-1,6-dihydropyrimidine;
5-Cyano-2-(4-methylphenyl)-4-(methylthio)-1-[4-(methylthio)phenyl]-6-oxo-1,6-dihydropyrimidine;
5-Cyano-1-(4-methoxyphenyl)-4-(methylthio)-2-[4-(methylthio)phenyl]-6-oxo-1,6-dihydropyrimidine;
1-(4-tert-Butylphenyl)-5-cyano-4-(methylthio)-2-[4-(methylthio)phenyl]-6-oxo-1,6-dihydropyrimidine;
5-Cyano-1-(4-methylphenyl)-4-(methylthio)-6-oxo-2-phenyl-1,6-dihydropyrimidine;
1-(4-n-Butylphenyl)-5-cyano-4-(methylthio)-2-[4-(methylthio)phenyl]-6-oxo-1,6-dihydropyrimidine;
5-Cyano-1-(4-fluorophenyl)-4-(methylthio)-6-oxo-2-pyridin-4-yl-1,6-dihydropyrimidine;
5-Cyano-1-(4-fluorophenyl)-4-(methylthio)-6-oxo-2-pyridin-3-yl-1,6-dihydropyrimidine;
5-Cyano-4-(methylthio)-1-[4-(methylthio)phenyl]-6-oxo-2-pyridin-3-yl-1,6-dihydropyrimidine;
5-Cyano-4-(methylthio)-1-[4-(methylthio)phenyl]-6-oxo-2-pyridin-4-yl-1,6-dihydropyrimidine;
5-Cyano-1-(4-fluorophenyl)-4-(methylthio)-6-oxo-2-pyridin-2-yl-1,6-dihydropyrimidine;
5-Cyano-4-(methylthio)-1-[4-(methylthio)phenyl]-6-oxo-2-pyridin-2-yl-1,6-dihydropyrimidine;
5-Cyano-4-(methylthio)-1-(4-methoxyphenyl)-6-oxo-2-pyridin-2-yl-1,6-dihydropyrimidine;
5-Cyano-4-(methylthio)-1-(3,4-dimethylphenyl)-6-oxo-2-pyridin-2-yl-1,6-dihydropyrimidine;
5-Cyano-4-(methylthio)-1-(4-ethylphenyl)-6-oxo-2-pyridin-2-yl-1,6-dihydropyrimidine;
5-Cyano-4-(methylthio)-1-(4-methylphenyl)-6-oxo-2-pyridin-2-yl-1,6-dihydropyrimidine;
5-Cyano-4-(methylthio)-1-(4-ethoxyphenyl)-6-oxo-2-pyridin-4-yl-1,6-dihydropyrimidine;
5-Cyano-4-(methylthio)-1-(4-methylphenyl)-6-oxo-2-pyridin-4-yl-1,6-dihydropyrimidine;
5-Cyano-4-(methylthio)-1-(4-isopropylphenyl)-6-oxo-2-pyridin-4-yl-1,6-dihydropyrimidine;
5-Cyano-4-(methylthio)-1-(4-ethylphenyl)-6-oxo-2-pyridin-3-yl-1,6-dihydropyrimidine;
5-Cyano-4-(methylthio)-1-(3,4-dimethylphenyl)-6-oxo-2-pyridin-3-yl-1,6-dihydropyrimidine;
5-Cyano-4-(methylthio)-1-(4-methoxyphenyl)-6-oxo-2-pyridin-3-yl-1,6-dihydropyrimidine;
Ethyl 1-(4-methylphenyl)-4-(methylthio)-2-[4-(methylthio)phenyl]-6-oxo-1,6-dihydropyrimidine-5-carboxylate;
Ethyl 1-(4-fluorophenyl)-4-(methylthio)-2-[4-(methylthio)phenyl]-6-oxo-1,6-dihydropyrimidine-5-carboxylate;
Ethyl 2-(4-fluorophenyl)-4-(methylthio)-1-[4-(methylthio)phenyl]-6-oxo-1,6-dihydropyrimidine-5-carboxylate;
5-Carboxamido-1-(4-methylphenyl)-4-(methylsulfonyl)-2-[4-(methylsulfonyl)phenyl]-6-oxo-1,6-dihydropyrimidine;
5-Carboxamido-1-(4-methylphenyl)-2-[4-(methylsulfonyl)phenyl]-6-oxo-4-piperazin-1-yl-1,6-dihydropyrimidine;
5-Carboxamido-4-(methylamino)-1-(4-methylphenyl)-2-[4-(methylsulfonyl)phenyl]-6-oxo-1,6-dihydropyrimidine;
5-Carboxamido-1-(4-methylphenyl)-2-[4-(methylsulfonyl)phenyl]-4-morpholin-4-yl-6-oxo-1,6-dihydropyrimidine;
5-Carboxamido-2-(4-fluorophenyl)-4-(methylsulfonyl)-1-[4-(methylsulfonyl)phenyl]-6-oxo-1,6-dihydropyrimidine;
5-Carboxamido-2-(4-fluorophenyl)-4-(methylamino)-1-[4-(methylsulfonyl)phenyl]-6-oxo-1,6-dihydropyrimidine;
5-Carboxamido-2-(4-fluorophenyl)-1-[4-(methylsulfonyl)phenyl]-4-morpholin-4-yl-6-oxo-1,6-dihydropyrimidine;
5-Carboxamido-1-(3,4-dimethylphenyl)-4-(methylsulfonyl)-2-[4-(methylsulfonyl)phenyl]-6-oxo-1,6-dihydropyrimidine;
5-Cyano-2-(4-fluorophenyl)-4-hydroxy-1-[4-(methylsulfonyl)phenyl]-6-oxo-1,6-dihydropyrimidine;
5-Cyano-1-(3,4-dimethylphenyl)-4-hydroxy-2-[4-(methylsulfonyl)phenyl]-6-oxo-1,6-dihydropyrimidine;
5-Cyano-4-(methylamino)-1-(4-methylphenyl)-2-[4-(methylthio)phenyl]-6-oxo-1,6-dihydropyrimidine;
5-Cyano-1-(3,4-dimethylphenyl)-4-(methylamino)-2-[4-(methylthio)phenyl]-6-oxo-1,6-dihydropyrimidine;
5-Cyano-2-(4-fluorophenyl)-4-(methylamino)-1-[4-(methylthio)phenyl]-6-oxo-1,6-dihydropyrimidine;
4-[5-Cyano-1-(3,4-dimethylphenyl)-4-(methylthio)-6-oxo-1,6-dihydropyrimidin-2-yl]benzenesulfonyl chloride;
4-[5-Cyano-2-(4-ethoxyphenyl)-4-(methylthio)-6-oxopyrimidin-1 (6H)-yl]benzenesulfonyl chloride;
4-[5-Cyano-1-(4-methylphenyl)-4-(methylthio)-6-oxo-1,6-dihydropyrimidin-2-yl]benzenesulfonamide;

N-({4-[5-Cyano-1-(4-methylphenyl)-4-(methylthio)-6-oxo-1,6-dihydropyrimidin-2-yl]phenyl}sulfonyl)acetamide;

N-({4-[5-Cyano-1-(3,4-dimethylphenyl)-4-(methylthio)-6-oxo-1,6-dihydropyrimidin-2-yl]phenyl}sulfonyl)acetamide;

N-({4-[5-Cyano-1-(4-methylphenyl)-4-(methylthio)-6-oxo-1,6-dihydropyrimidin-2-yl]phenyl}sulfonyl)-2,2,2-trifluoroacetamide;

N-({4-[5-Cyano-1-(3,4-dimethylphenyl)-4-(methylthio)-6-oxo-1,6-dihydropyrimidin-2-yl]phenyl}sulfonyl)-2,2,2-trifluoroacetamide;

N-({4-[5-Cyano-1-(4-methylphenyl)-4-(methylthio)-6-oxo-1,6-dihydropyrimidin-2-yl]phenyl}sulfonyl)benzamide and N-({4-[5-Cyano-1-(3,4-dimethylphenyl)-4-(methylthio)-6-oxo-1,6-dihydropyrimidin-2-yl]phenyl}sulfonyl)benzamide.

According to another embodiment of the present invention, there is provided a process for the preparation of novel pyrimidones of the formula (I) wherein all symbols are as defined earlier, which comprises reacting a compound of the formula (Ia)

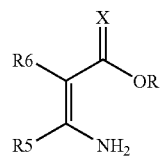

(Ia)

where R represent ($C_1$-$C_3$) alkyl group, X, $R^5$ and $R^6$ are as defined above, with a compound of the formula (Ib)

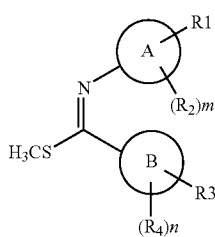

(Ib)

wherein all symbols are as defined above, to produce a compound of formula (I).

The reaction of compound of formula (Ia) with compound of formula (Ib) may be carried out using appropriate solvents like toluene, xylene, tetrahydrofuran, dioxane, chloroform, dichloromethane, dichloroethane, o-dichlorobenzene, acetone, ethyl acetate, acetonitrile, N,N-dimethylformamide, dimethylsulfoxide, pyridine, ethanol, methanol, isopropylalcohol, tert-butylalchol, acetic acid, propionic acid etc, a mixture thereof or the like or by neat reactions. The condensation reaction may be carried out under acidic conditions using mineral or organic acids, or basic conditions viz. carbonates, bicarbonates, hydrides, hydroxides, alkyls and alkoxides of alkali metals and alkaline earth metals. The reaction may be carried out by using phase transfer catalysts viz. triethylbenzylammonium chloride, tetrabutylammonium bromide, tetrabutylammonium hydrogensulphate, tricaprylylmethylammonium chloride (aliquat 336) and the like. The reaction is usually carried out under cooling to refluxing conditions. The final product purified by using chromatographic techniques or by recrystallization. The reaction may be carried out for period in the range of 2 to 20 h.

According to another embodiment of the present invention, there is provided a process for the preparation of novel pyrimidones of the formula (I) wherein all symbols are as defined earlier, which comprises reacting a compound of the formula (Ic)

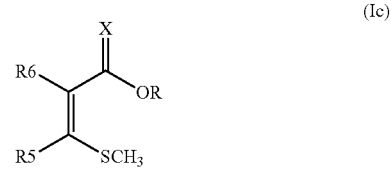

(Ic)

where R represent ($C_1$-$C_3$) alkyl group and all other symbols are as defined above, with a compound of the formula (Id)

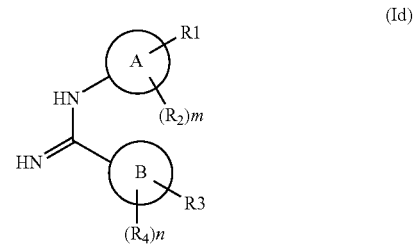

(Id)

wherein all symbols are as defined above, to produce a compound of formula (I).

The reaction of compound of formula (Ic) with compound of formula (Id) may be carried out using appropriate solvents like toluene, xylene, tetrahydrofuran, dioxane, chloroform, dichloromethane, dichloroethane, o-dichlorobenzene, acetone, ethyl acetate, acetonitrile, N,N-dimethylformamide, dimethylsulfoxide, pyridine, ethanol, methanol, isopropylalcohol, tert-butylalcohol, acetic acid, propionic acid etc, a mixture thereof or the like or by neat reactions. The condensation reaction may be carried out under acidic conditions using mineral or organic acids, or basic conditions viz. carbonates, bicarbonates, hydrides, hydroxides, alkyls and alkoxides of alkali metals and alkaline earth metals. The reaction may be carried out by using phase transfer catalysts viz. triethylbenzylammonium chloride, tetrabutylammonium bromide, tetrabutylammonium hydrogensulphate, tricaprylylmethylammonium chloride (aliquat 336) and the like. The reaction is usually carried out under cooling to refluxing conditions. The final product purified by using chromatographic techniques or by recrystallization. The reaction may be carried out for period in the range of 30 min. to 10 hours.

According to yet another embodiment of the present invention there is provided a process for the conversion of novel pyrimidones of the formula (I) wherein any of the groups $R^1$ or $R^3$ represent $SR^7$, wherein $R^7$ represents hydrogen, alkyl or aryl to novel pyrimidones of the formula (I) wherein any of the groups $R^1$ or $R^3$ represent $S(O)_pR^8$, where p represents 1 or 2 and $R^8$ represents alkyl or aryl; by using suitable oxidizing agent. The oxidizing agent may be selected from potassium peroxymonosulfate (Oxone), hydrogen peroxide, tert-butylperoxide, Jones reagent, peracid [e.g peracetic acid, perbenzoic acid, m-chloroperbenzoic acid etc], chromic acid, potassium permanganate, alkali metal periodate [e.g sodium periodate, etc], magnesium mono peroxypthalate, osmium tetroxide/N-methylmorpholine-N-oxide, sodium tungstate, and the like. The oxidation is usually carried out in a solvent which does not adversely influence the reaction such as acetic acid, dichloromethane, acetone, ethyl acetate, chloroform, water, an alcohol such as, methanol, ethanol, isopropanol and the like or mixture thereof. The reaction temperature is usually carried out under cooling to refluxing conditions.

According to yet another embodiment of the present invention there is provided a process for the conversion of novel pyrimidones of the formula (I) wherein $R^1$ or $R^3$ represent $S(O)_pR^8$, where p is 1 or 2, $R^8$ represents alkyl or aryl may be converted to novel pyrimidones of the formula (I) wherein $R^1$ or $R^3$ represent $S(O)_pR^8$, where p is 1 or 2, $R^8$ represents amino by using the procedure described in the literature (Huang et. al. Tetrahedron Lett., 39, 7201, 1994).

In yet another embodiment of the present invention, there is provided a process for the preparation of novel pyrimidones of the formula (I) wherein either of $R^1$ or $R^3$ represent $S(O)_pR^8$, wherein $R^8$ represents amino group and p represents an integer of 1 or 2 and all other symbols are as defined earlier, which comprises reacting compound of formula (Ie) wherein all symbols are as defined earlier

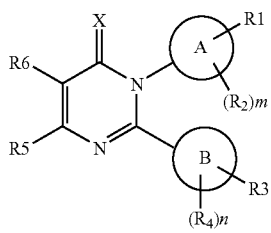

(Ie)

where either of $R^1$ or $R^3$ represents hydrogen with chlorosulfonic acid and ammonia.

The reaction of compound of formula (Ie) with chlorosulfonic acid and ammonia may be carried out in the presence of solvents such as acetic acid, dichloromethane, acetone, tetrahydrofuran, dioxane, ethyl acetate, chloroform, water, an alcohol and the like or a mixture thereof or in absence of solvents. The reaction may be carried out at a temperature in the range of 0° C. to reflux temperature for period in the range of 2 to 24 h.

In yet another embodiment of the present invention, there is provided a novel intermediate of formula (Ib)

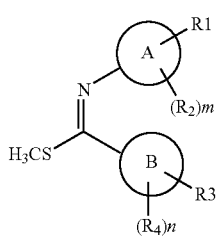

(Ib)

their derivatives, their analogs, their tautomeric forms, their stereoisomers, their polymorphs, and their pharmaceutically acceptable salts, wherein the rings represented by A and B are selected from aryl or heteroaryl; $R^1$ and $R^3$ are different and represent hydrogen, $SR^7$, wherein $R^7$ represents hydrogen, alkyl or aryl, or $S(O)_pR^8$, wherein $R^8$ represents alkyl, amino or aryl group and p represents an integer of 1 or 2; $R^2$ and $R^4$ may be same or different and independently represent hydrogen, halogen, hydroxyl, nitro, cyano, azido, nitroso, amino, formyl, alkyl, haloalkyl, acyl, alkoxy, monoalkylamino, dialkylamino, acylamino, alkoxycarbonyl, alkylsulfonyl, alkylsulfinyl, alkylsulfanyl, sulfamoyl, alkoxyalkyl groups or carboxylic acids or its derivatives; m is an integer and is in the range of 0 to 4; n is an integer and is in the range of 0 to 4.

In yet another embodiment of the present invention, there is provided a process for the preparation of novel intermediate of formula (Ib), which comprises, methylating the compound of formula (Ib-2)

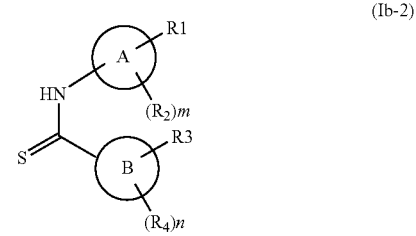

(Ib-2)

The methylation of Ib-2 may be carried out by treating with methylating agent like methyliodide, dimethylsulphate and diazomethane etc., in the presence of base such as sodium hydroxide, potassium hydroxide, sodium methoxide, sodium hydride, potassium t-butoxide, calcium hydroxide, magnesium hydroxide and the like, in solvents like ether, tetrahydrofuran, methanol, t-butanol, dioxane, isopropanol, ethanol, water etc.

In yet another embodiment of the present invention, there is provided a process for the preparation of novel intermediate of formula (Ib-2), which comprises, reacting compound of formula (Ib-3)

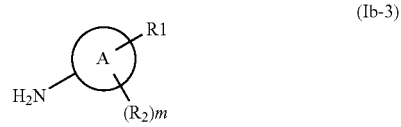

(Ib-3)

where $R_1$ and $R_2$ all are as defined above with compound of formula (Ib-4)

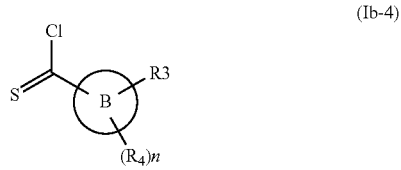

(Ib-4)

where all symbols are as defined above.

The reaction of compound of formula (Ib-3) with compound of formula (Ib-4) may be carried out in solvents like toluene, xylene, tetrahydrofuran, dioxane, chloroform, dichloromethane, dichloroethane, o-dichlorobenzene, acetone, ethyl acetate, acetonitrile, N,N-dimethylformamide, dimethylsulfoxide, pyridine, ethanol, methanol, isopropylalcohol, tert-butylalcohol, acetic acid, propionic acid etc, a mixture thereof or the like or by neat reactions. The reaction may be carried out at a temperature in the range of 0 to 200° C. for period in the range of 30 min. to 5 hours.

In yet another embodiment of the present invention, there is provided a novel intermediate of formula (Id)

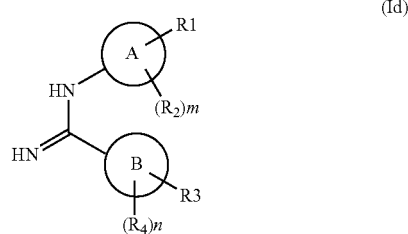

their derivatives, their analogs, their tautomeric forms, their stereoisomers, their polymorphs, and their pharmaceutically acceptable salts, wherein the rings represented by A and B are selected from aryl or heteroaryl; $R^1$ and $R^3$ are different and represent hydrogen, $SR^7$, wherein $R^7$ represents hydrogen, alkyl or aryl, or $S(O)_p R^8$, wherein $R^8$ represents alkyl, amino or aryl group and p represents an integer of 1 or 2; $R^2$ and $R^4$ may be same or different and independently represent hydrogen, halogen, hydroxyl, nitro, cyano, azido, nitroso, amino, formyl, alkyl, haloalkyl, acyl, alkoxy, monoalkylamino, dialkylamino, acylamino, alkoxycarbonyl, alkylsulfonyl, alkylsulfinyl, alkylsulfanyl, sulfamoyl, alkoxyalkyl groups or carboxylic acids or its derivatives; m is an integer and is in the range of 0 to 4; n is an integer and is in the range of 0 to 4.

In yet another embodiment of the present invention, there is provided a process for the preparation of novel intermediate of formula (Id), which comprises, reacting compound of formula (Ib-3)

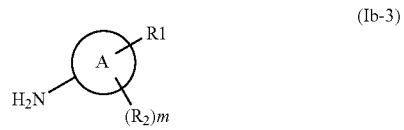

where $R_1$ and $R_2$ all are as defined above with compound of formula (Id-1)

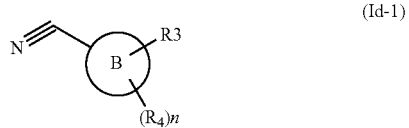

where all symbols are as defined above.

The reaction of compound of formula (Ib-3) with compound of formula (Id-1) may be carried out in the presence of catalysts like aluminium chloride, triethyl aluminium, sodium hydride, sodium methoxide, butyl lithium, lithium diisopropylamine, sodium bis trimethyl silylamide, lithium bis trimethyl silylamide, using solvents like toluene, xylene, tetrahydrofuran, dioxane, chloroform, dichloromethane, dichloroethane, o-dichlorobenzene, acetone, ethyl acetate, acetonitrile, N,N-dimethylformamide, dimethylsulfoxide, ethanol, methanol, isopropylalcohol, tert-butylalchol, acetic acid, propionic acid etc, a mixture thereof or the like or by neat reactions. The reaction may be carried out at a temperature in the range of 0 to 200° C. for period in the range of 30 min. to 10 hours.

It is appreciated that in any of the above-mentioned reactions, any reactive group in the substrate molecule may be protected according to conventional chemical practice. Suitable protecting groups in any of the above-mentioned reactions are those used conventionally in the art. The methods of formation and removal of such protecting groups are those conventional methods appropriate to the molecule being protected.

The pharmaceutically acceptable salts are prepared by reacting the compound of formula (I) with 1 to 4 equivalents of a base such as sodium hydroxide, sodium methoxide, sodium hydride, potassium t-butoxide, calcium hydroxide, magnesium hydroxide and the like, in solvents like ether, tetrahydrofuran, methanol, t-butanol, dioxane, isopropanol, ethanol etc. Mixture of solvents may be used. Organic bases such as diethanolamine, α-phenylethylamine, benzylamine, piperidine, morpholine, pyridine, hydroxyethylpyrrolidine, hydroxyethylpiperidine, choline, guanidine and the like, ammonium or substituted ammonium salts, aluminum salts. Amino acid such as glycine, alanine, cystine, cysteine, lysine, arginine, phenylalanine etc may be used for the preparation of amino acid salts. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzenesulfonic acid, tartaric acid and in solvents like ethyl acetate, ether, alcohols, acetone, tetrahydrofuran, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). More specifically the compound of formula (I) may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula (I) may be prepared by hydrolysing the pure diastereomeric amide.

Various polymorphs of compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, ir spectroscopy, differential scanning calorimetry, powder X-ray diffraction or such other techniques.

Pharmaceutically acceptable solvates of the compounds of formula (I) forming part of this invention may be prepared by conventional methods such as dissolving the compounds of formula (I) in solvents such as water, methanol, ethanol, mixture of solvents such as acetone:water, dioxane:water, N,N-dimethylformamide:water and the like, preferably water and recrystallizing by using different crystallization techniques.

The present invention provides a pharmaceutical composition, containing the compounds of the general formula (I) as defined above, their derivatives, their analogs, their tautomeric forms, their stereoisomers, their polymorphs, their pharmaceutically acceptable hydrates and solvates in combination with the usual pharmaceutically employed carriers, diluents and the like, useful for the treatment of inflammation, arthritis, pain, fever, psoriasis, allergic diseases, asthma, inflammatory bowel syndrome, gastro-intestinal ulcers, cardiovascular disorders including ischemic heart disease, atherosclerosis, cancer, ischemic-induced cell damage, particularly brain damage caused by stroke, other pathological disorders associated with free radicals.

The pharmaceutical composition may be in the forms normally employed, such as tablets, capsules, powders, syrups, solutions, aerosols, suspensions and the like, may contain flavoring agents, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carriers, diluents or solvents.

The present invention is provided by the examples given below, which are provided by way of illustration only and should not be considered to limit the scope of the invention.

Preparation 1

4-Chloro-N-[4-(methylthio)phenyl]benzenecarboximidamide

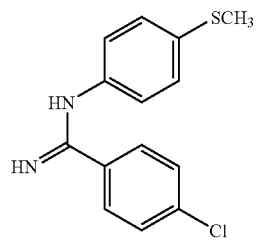

Finely powdered anhydrous aluminium chloride (0.83 g, 6 mmol) was added to a stirred mixture of 4-chlorobenzonitrile (0.6875 g, 5 mmol) and 4-methylthioaniline (0.695 g, 5 mmol) over a period of 30 min. The reaction mixture was heated at 180-190° C. for 3 hours with stirring and allowed to cool to 50° C. The resultant mixture was triturated with ethyl acetate and basified with sodium hydroxide (20%) solution. The ethyl acetate layer was washed with water, dried over anhydrous sodium sulphate and concentrated to give the crude product, which was purified by column chromatography to yield the title compound (0.6 g, 43.4%, purity 98.8% by HPLC), mp 148-150° C. $^1$H-NMR (CDCl$_3$):δ 2.48 (s, 3H), 6.90-6.97(m, 2H), 7.11-7.41(m, 4H), 7.74 (bs, 2H). MS m/z:277.0 (M$^+$)

Preparation 2

4-Fluoro-N-[4-(methylthio)phenyl]benzenecarboximidamide

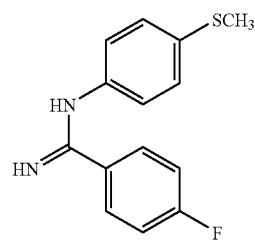

The title compound was prepared from 4-fluorobenzonitrile (2.176 g, 17.98 mmol) and 4-methylthioaniline (2.5 g, 17.98 mmol) by following the procedure described in preparation 1, (2.06 g, 44.1%, purity 98.8% by HPLC), mp 121-124° C. $^1$H-NMR (CDCl$_3$):δ 2.48 (s, 3H), 4.82 (bs, 2H, D$_2$O exchangeable), 6.91-6.93 (d, 2H), 7.1-7.14 (m, 2H), 7.26-7.30 (m, 2H), 7.86 (bs, 2H). MS m/z:261.1(M$^+$)

Preparation 3

N-[4-(Methylthio)phenyl]benzenecarboximidamide

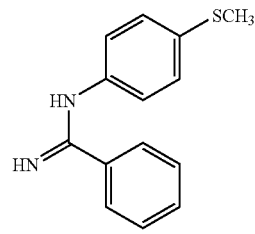

The title compound was prepared from benzonitrile (3.705 g, 35.97 mmol) and 4-methylthioaniline (5.0 g, 35.97 mmol) by following the procedure described in preparation 1, (3.66 g, 42.1%, purity 99.8% by HPLC), mp 129-131° C. $^1$H-NMR (CDCl$_3$):δ 2.49 (s, 3H), 4.84 (bs, 2H), 6.94-6.96 (d, 2H), 7.26-7.31 (m, 2H), 7.45-7.49 (m, 3H), 7.87-7.88 (d, 2H). MS m/z:243.2 (M$^+$)

Preparation 4

N-[4-(Methylthio)phenyl]-4-(trifluoromethyl)benzenecarboximidamide

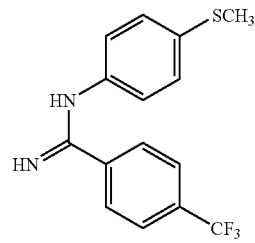

The title compound was prepared from 4-trifluoromethylbenzonitrile (0.62 g, 3.6 mmol) and 4-methylthioaniline (0.5 g, 3.6 mmol) by following the procedure described in preparation 1, (0.495 g, 44.4%, purity 98.3% by HPLC), mp 144-146° C. $^1$H-NMR (CDCl$_3$): δ 2.49 (s, 3H), 4.8 (bs, 2H), 6.93-6.95 (d, 2H), 7.26-7.32 (m, 2H), 7.70-7.72 (d, 2H), 7.99-8.01 (d, 2H). MS m/z:311.1(M$^+$).

Preparation 5

N-(4-Fluorophenyl)-4-(methylthio)benzenecarboximidamide

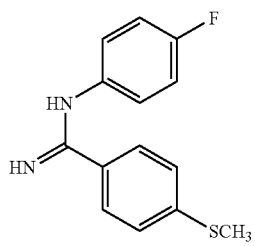

The title compound was prepared from 4-methylthiobenzonitrile (0.50 g, 33.6 mmol) and 4-fluoroaniline (0.372 g, 33.6 mmol) by following the procedure described in preparation 1, (0.43 g, 49.3%, mp 145-147° C., purity 94.7% by HPLC). $^1$H-NMR (CDCl$_3$): δ 2.52 (s, 3H), 6.93-6.94 (m, 3H), 7.17-7.32 (m, 5H). MS m/z:261.1(M$^+$)

Preparation 6

N-(4-Methylphenyl)-4-(methylthio)benzenecarboximidamide

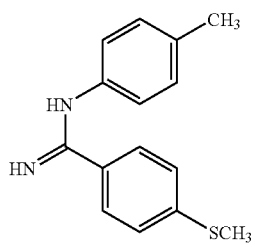

The title compound was prepared from 4-methylthiobenzonitrile (2.50 g, 16.78 mmol) and 4-methylaniline (1.789 g, 16.78 mmol) by following the procedure described in preparation 1, (2.05 g, 47.6%, purity 79% by HPLC), mp 143-145° C. $^1$H-NMR (CDCl$_3$): δ 2.33 (s, 3H), 2.52 (s, 3H), 4.75 (bs, 2H, D$_2$O exchangeable), 6.87-6.89 (d, 2H), 7.14-7.16 (d, 2H), 7.27-7.29 (d, 2H), 7.7-7.79 (d, 2H). MS m/z: 257.1(M$^+$).

Preparation 7

4-Methylsulphonylbenzonitrile

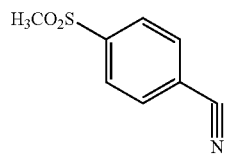

A solution of oxone (18.42 g, 0.03 mol) in water (70 ml) was added dropwise to the vigorous stirred solution of 4-methylthiobenzonitrile (1.49 g, 0.01 mol) in methanol (50 ml) at 20° C. and stirring was continued for three hours. The reaction mixture was diluted with water (50 ml) and extracted with ethyl acetate. The ethyl acetate extract was washed with water, dried over anhydrous sodium sulphate and concentrated under reduced pressure to finish the title compound (1.3 g, 72.2%), mp 145-149° C. The compound was used with out any purification for the next step. $^1$H-NMR (CDCl$_3$): δ 3.1 (s, 3H), 7.8-7.9 (d, 2H), 8.08-8.1 (d, 2H).

Preparation 8

N-(4-Methylphenyl)-4-(methylsulfonyl)benzenecarboximidamide

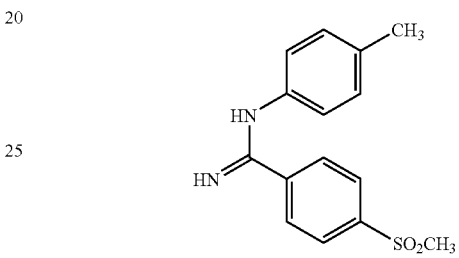

The title compound was obtained from 4-methylsulphonylbenzonitrile (2.00 g, 11 mmol) (obtained according to the procedure described in preparation 7) and 4-methylaniline (1.18 g, 11 mmol) according to the procedure described in preparation 1, (1.25 g, 39.3%, purity 90.7% by HPLC), mp 187-189° C. $^1$H-NMR (CDCl$_3$): δ 2.34 (s, 3H), 3.07(s, 3H), 4.92 (bs, 2H, D$_2$O exchangeable), 6.87-6.89 (d, 2H), 7.18-7.20 (d, 2H), 8.01-8.03 (d, 2H), 8.08-8.1 (d, 2H). MS m/z:289.1(M$^+$).

Preparation 9

N-(4-Isopropylphenyl)-4-(methylthio)benzenecarboximidamide

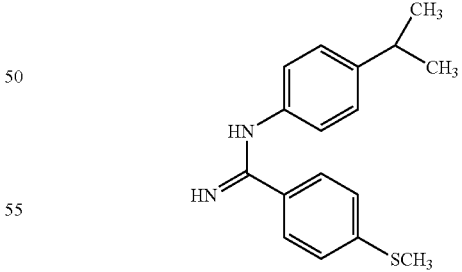

The title compound was obtained from 4-methylthiobenzonitrile (7.45 g, 50 mmol) and 4-isopropylaniline (6.75 g, 50 mmol) by following the procedure described in preparation 1 (7.41 g, yield 52.11%, purity 97.9% by HPLC). $^1$H-NMR (CDCl$_3$): δ 1.24-1.26 (d, 6H), 2.52 (s, 3H), 2.87-2.91 (m, 1H), 4.8 (bs, 2H, D$_2$O exchangeable), 6.89-6.91 (d, 2H), 7.20-7.22 (d, 2H), 7.27-7.30 (d, 2H), 7.79-7.81 (d, 2H). MS m/z:285.1 (M$^+$).

Preparation 10

N-(3,4-Dimethylphenyl)-4-(methylthio)benzenecarboximidamide

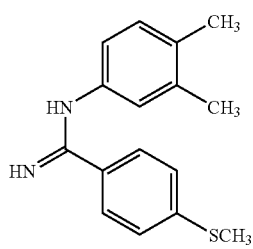

To a solution of 3,4-dimethylaniline (10 g, 83 mmol) in THF (10 ml), lithium bis(trimethylsilyl)amide (20% in THF, 93 ml, 99 mmol) was added under stirring in nitrogen blanket for a period of 20 minutes followed by 4-methylthiobenzonitrile (12.31 g, 83 mmol) over a period of 10 min. After 1 hour the reaction mixture was poured over ammonium chloride solution (30%, 100 ml). The resultant mixture was extracted with ethyl acetate and washed with water, dried over anhydrous sodium sulphate. The ethyl acetate extract was concentrated to yield the title compound (19 g, yield 85.1%, mp 111-113° C., purity 99.1% by HPLC). $^1$H-NMR (CDCl$_3$):δ 2.23-2.24 (d, 6H), 2.51 (s, 3H), 4.81 (bs, 2H, D$_2$O exchangeable), 6.70-6.72 (m, 1H), 6.77 (s, 1H), 7.08-7.1 (d, 1H), 7.25-7.27 (d, 2H), 7.76-7.78 (d, 2H). MS m/z: 271.3 (M$^+$).

Preparation 11

N-(4-Isopropylphenyl)-4-(methylsulfonyl)benzenecarboximidamide

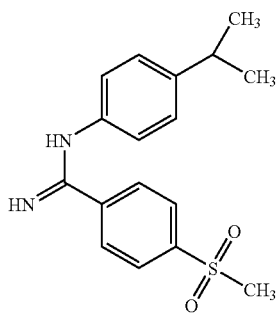

The title compound was prepared from 4-methylsulfonylbenzonitrile (5.43 g, 30 mmol) and 4-isopropylaniline (4.05 g, 30 mmol) by following the procedure described in preparation 1 (5.66 g, yield 60%, purity 88% by HPLC). $^1$H-NMR (CDCl$_3$):δ 1.25-1.27 (d, 6H), 2.9-2.95 (m, 1H), 3.07 (s, 3H), 4.92 (bs, 2H, D$_2$O exchangeable), 6.90-6.92 (d, 2H), 7.23-7.26 (d, 2H), 8.01-8.03 (d, 2H), 8.08-8.1 (d, 2H). MS m/z:317.2 (M$^+$).

Preparation 12

N-(3,4-Dimethylphenyl)-4-(methylsulfonyl)benzenecarboximidamide

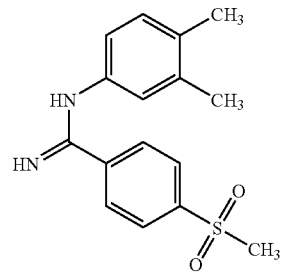

The title compound was prepared from 4-methylsulfonylbenzonitrile (5.0 g, 28 mmol) and 3,4-dimethylaniline (3.36 g, 28 mmol) by following the procedure described in preparation 1 (3.75 g, yield 45%, purity 97.1% by HPLC). $^1$H-NMR (CDCl$_3$):δ 2.25-2.26 (d, 6H), 3.07 (s, 3H), 4.91 (bs, 2H, D$_2$O exchangeable), 6.71-6.73 (m, 1H), 6.78 (s, 1H), 7.12-7.14 (d, 1H), 8-8.02 (d, 2H), 8.07-8.09 (d, 2H). MS m/z:303.2 (M$^+$).

Preparation 13

N-(3,4,5-Trimethoxyphenyl)-4-(methylthio)benzenecarboximidamide

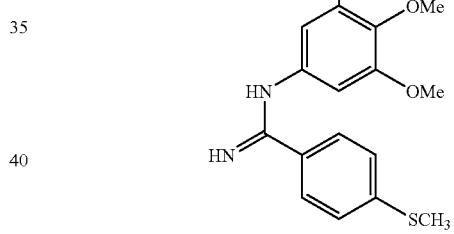

The title compound was prepared from 4-methylthiobenzonitrile (4.1 g, 27 mmol) and 3,4,5-trimethoxyaniline (5 g, 27 mmol) by following the procedure described in preparation 10 (7.8 g, yield 86.32%). $^1$H-NMR (CDCl$_3$):δ 2.51 (s, 3H), 3.8 (s, 9H), 4.9 (bs, 2H, D$_2$O exchangeable), 6.23 (s, 2H), 7.24-7.30 (m, 2H), 7.78-7.8 (d, 2H). MS m/z:333.5 (M$^+$).

Preparation 14

N-(4-Ethylphenyl)-4-(methylthio)benzenecarboximidamide

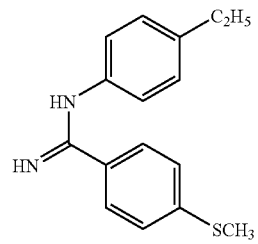

The title compound was prepared from 4-methylthiobenzonitrile (1.23 g, 8.2 mmol) and 4-ethylaniline (1 g, 8.2 mmol) by following the procedure described in preparation 10 (1.81 g, yield 81.1%, mp 156-158° C., purity 98.6% by HPLC). $^1$H-NMR (CDCl$_3$): δ 1.22-1.26 (t, 3H), 2.51 (s, 3H), 2.60-2.66 (q, 2H), 4.70 (bs, 2H, D$_2$O exchangeable), 6.89-6.91 (d, 2H), 7.17-7.19 (d, 2H), 7.26-7.29 (m, 2H), 7.79-7.81 (d, 2H). MS m/z:271.3 (M$^+$).

Preparation 15

N-(4-Bromophenyl)-4-(methylthio)benzenecarboximidamide

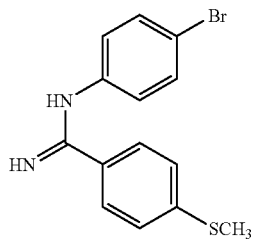

The title compound was prepared from 4-methylthiobenzonitrile (17.3 g, 116 mmol) and 4-bromoaniline (20 g, 116 mmol) by following the procedure described in preparation 10 (29 g, yield 77.7%, purity 99.8% by HPLC). MS m/z: 321.1/323.2 (M$^+$).

Preparation 16

N-(4-Methoxyphenyl)-4-(methylthio)benzenecarboximidamide

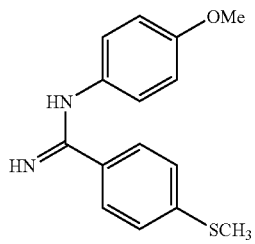

The title compound was prepared from 4-methylthiobenzonitrile (12.11 g, 81 mmol) and 4-methoxyaniline (10 g, 81 mmol) by following the procedure described in preparation 10 (17 g, yield 76.84%, mp 166-168° C., purity 97.25% by HPLC). $^1$H-NMR (CDCl$_3$): δ 2.51 (s, 3H), 3.80 (s, 3H), 4.80 (bs, 2H, D$_2$O exchangeable), 6.91 (s, 4H), 7.26-7.29 (m, 2H), 7.78-7.8 (d, 2H). IR (KBr) cm$^{-1}$: 3461, 3320, 2949, 2922, 2829, 1615. MS m/z:273.1 (M$^+$).

Preparation 17

N-(4-Fluorophenyl)benzenecarboximidamide

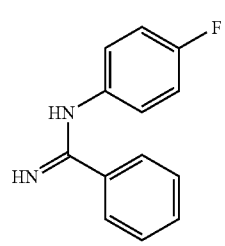

The title compound was prepared from benzonitrile (13.9 g, 135 mmol) and 4-fluoroaniline (15 g, 135 mmol) by following the procedure described in preparation 10 (24.6 g, yield 85.1%, purity 99.7% by HPLC). MS m/z:215.2 (M$^+$).

Preparation 18

N-(4-Chlorophenyl)-4-(methylthio)benzenecarboximidamide

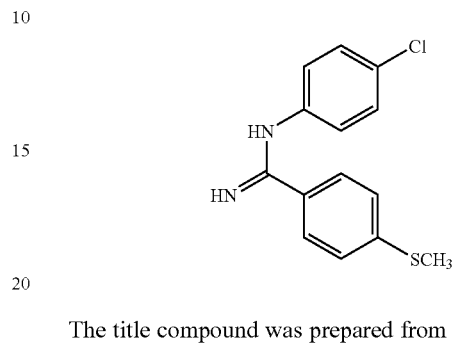

The title compound was prepared from 4-methylthiobenzonitrile (11.7 g, 78 mmol) and 4-chloroaniline (10 g, 78 mmol) by following the procedure described in preparation 10 (18.06 g, yield 83.26%, purity 98.9% by HPLC). MS m/z:277.1/278.7 (M$^+$).

Preparation 19

N-(2,4-Dimethylphenyl)-4-(methylthio)benzenecarboximidamide

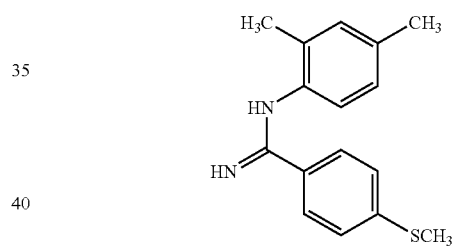

The title compound was prepared from 4-methylthiobenzonitrile (18.46 g, 123 mmol) and 2,4-dimethylaniline (15 g, 123 mmol) by following the procedure described in preparation 10 (25.17 g, yield 75.2%, purity 99% by HPLC). $^1$H-NMR (CDCl$_3$):δ 2.16 (s, 3H), 2.31 (s, 3H), 2.53 (s, 3H), 4.5 (bs, 2H, D$_2$O exchangeable), 6.76-6.78 (d, 1H), 6.98-7.0 (d, 1H), 7.05 (s, 1H), 7.27-7.31 (m, 2H), 7.81-7.83 (d, 2H). MS m/z:271.3 (M$^+$).

Preparation 20

4-Methyl-N-(4-methylthio)benzenecarboximidamide

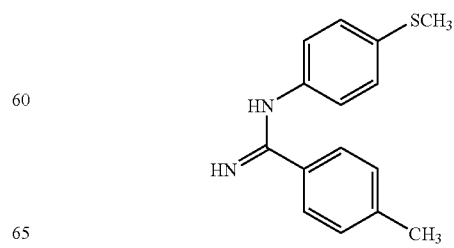

The title compound was prepared from 4-methylbenzonitrile (8.42 g, 72 mmol) and 4-methylthioaniline (10 g, 72 mmol) by following the procedure described in preparation 10 (12.25 g, yield 66.5%, purity 99.8% by HPLC). $^1$H-NMR (CDCl$_3$):δ 2.40 (s, 3H), 2.48 (s, 3H), 4.82 (bs, 2H, D$_2$O exchangeable), 6.92-6.94 (d, 2H), 7.22-7.29 (m, 4H), 7.74-7.75 (d, 2H). MS m/z:257.1 (M$^+$).

Preparation 21

N-(4-Ethoxyphenyl)-4-(methylthio)benzenecarboximidamide

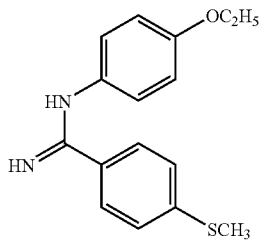

The title compound was prepared from 4-methylthiobenzonitrile (10.87 g, 73 mmol) and 4-ethoxyaniline (10 g, 73 mmol) by following the procedure described in preparation 10 (12.7 g, yield 61%, purity 96.27% by HPLC). $^1$H-NMR (CDCl$_3$):δ 1.39-1.43 (t, 3H), 2.51 (s, 3H), 3.99-4.04 (q, 2H), 4.75 (bs, 2H, D$_2$O exchangeable), 6.90 (s, 4H), 7.26-7.29 (m, 2H), 7.77-7.79 (d, 2H). MS m/z:287.2 (M$^+$).

Preparation 22

N-(4-tert-Butylphenyl)-4-(methylthio)benzenecarboximidamide

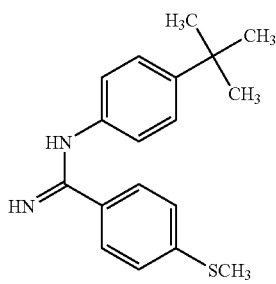

The title compound was prepared from 4-methylthiobenzonitrile (1 g, 6.7 mmol) and 4-tert-butylaniline (1 g, 6.7 mmol) by following the procedure described in preparation 10 (1.24 g, yield 62.13%, purity 98.67% by HPLC). $^1$H-NMR (CDCl$_3$):δ 1.32 (s, 9H), 2.51 (s, 3H), 4.81 (bs, 2H, D$_2$O exchangeable), 6.90-6.92 (d, 2H), 7.26-7.29 (m, 2H), 7.35-7.37 (m, 2H), 7.78-7.8 (d, 2H). MS m/z:299.4 (M$^+$).

Preparation 23

N-(4-Methylphenyl)benzenecarboximidamide

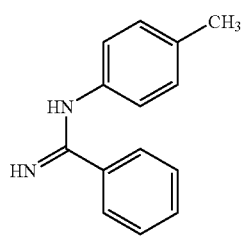

The title compound was prepared from benzonitrile (0.96 g, 9 mmol) and 4-methylaniline (1 g, 9 mmol) by following the procedure described in preparation 10 (1.08 g, yield 55%, purity 98.42% by HPLC). $^1$H-NMR (CDCl$_3$):δ 2.33 (s, 3H), 5 (bs, 2H, D$_2$O exchangeable), 6.89-6.91 (d, 2H), 7.15-7.17 (d, 2H), 7.44-7.46 (m, 3H), 8 (bs, 2H). MS m/z:211.2 (M$^+$).

Preparation 24

N-(4-Butylphenyl)-4-(methylthio)benzenecarboximidamide

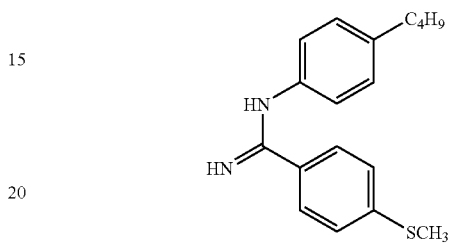

The title compound was prepared from 4-methylthiobenzonitrile (1 g, 6.7 mmol) and 4-n-butylaniline (1 g, 6.7 mmol) by following the procedure described in preparation 10 (1.27 g, yield 63.66%). $^1$H-NMR (CDCl$_3$):δ 0.91-0.95 (t, 3H), 1.33-1.39 (m, 2H), 1.56-1.63 (m, 2H), 2.52 (s, 3H), 2.56-2.6 (m, 2H), 4.8 (bs, 2H, D$_2$O exchangeable), 6.88-6.9 (d, 2H), 7.15-7.17 (d, 2H), 7.27-7.29 (m, 2H), 7.79-7.81 (d, 2H). MS m/z:299.3 (M$^+$).

Preparation 25

N-(4-Fluorophenyl)pyridine-4-carboximidamide

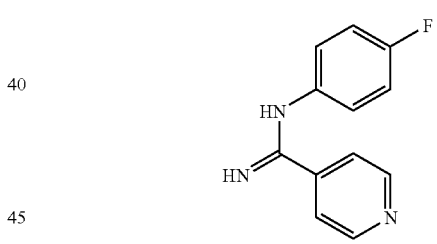

The title compound was prepared from 4-cyanopyridine (0.94 g, 9 mmol) and 4-fluoroaniline (1 g, 9 mmol) by following the procedure described in preparation 10 (1.1 g, yield 56.5%).

Preparation 26

N-(4-Fluorophenyl)pyridine-3-carboximidamide

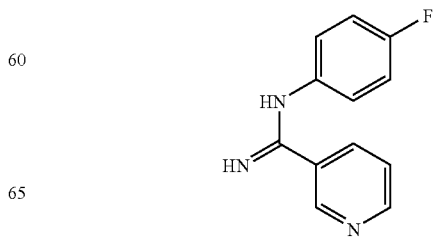

The title compound was prepared from 3-cyanopyridine (0.94 g, 9 mmol) and 4-fluoroaniline (1 g, 9 mmol) by following the procedure described in preparation 10 (1.5 g, yield 76.9%, purity 97.95% by HPLC). $^1$H-NMR (CDCl$_3$):δ 4.93 (bs, 2H, D$_2$O exchangeable), 6.92-6.96 (m, 2H), 7.05-7.07 (m, 2H), 7.38-7.41 (m, 1H), 8.22 (s, 1H), 8.71-8.72 (d, 1H), 9.06 (s, 1H). MS m/z:216.3 (M$^+$).

Preparation 27

N-[(4-Methylthio)phenyl]pyridine-3-carboximidamide

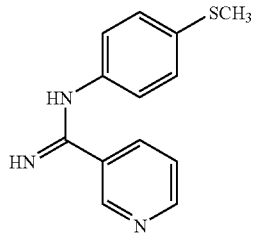

The title compound was prepared from 3-cyanopyridine (1.5 g, 14 mmol) and 4-methylthioaniline (2 g, 14 mmol) by following the procedure described in preparation 10 (2.43 g, yield 69.43%, mp 172-183 C purity 92.1% by HPLC). $^1$H-NMR (CDCl$_3$): δ 2.49 (s, 3H), 4.92 (bs, 2H, D$_2$O exchangeable), 6.93-6.95 (d, 2H), 7.26-7.41 (m, 3H), 8.22-8.24 (d, 1H), 8.71-8.72 (d, 1H), 9 (s, 1H). IR (KBr) cm$^{-1}$: 3069, 2917, 1662. MS m/z:244.3 (M$^+$).

Preparation 28

N-[(4-Methylthio)phenyl]pyridine-4-carboximidamide

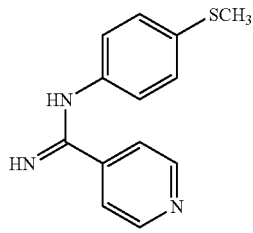

The title compound was prepared from 4-cyanopyridine (1.5 g, 14 mmol) and 4-methylthioaniline (2 g, 14 mmol) by following the procedure described in preparation 10 (1.87 g, yield 53.6%).

Preparation 29

N-(4-Fluorophenyl)pyridine-2-carboximidamide

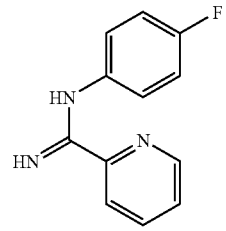

The title compound was prepared from 2-cyanopyridine (0.94 g, 9 mmol) and 4-fluoroaniline (1 g, 9 mmol) by following the procedure described in preparation 10 (1.1 g, yield 56.81%). $^1$H-NMR (CDCl$_3$):δ 6.98-7.09 (m, 2H), 7.26 (s, 2H), 7.39-7.42 (d, 1H), 7.82-7.84 (m, 1H), 8.38-8.4 (d, 1H), 8.57-8.58 (s, 1H). MS m/z: 216.3 (M$^+$).

Preparation 30

N-[(4-Methylthio)phenyl]pyridine-2-carboximidamide

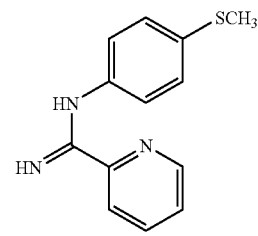

The title compound was prepared from 2-cyanopyridine (1.5 g, 14 mmol) and 4-methylthioaniline (2 g, 14 mmol) by following the procedure described in preparation 10 [3.0 g, yield 85.71%(crude basis)].

Preparation 31

N-(4-Methoxyphenyl)pyridine-2-carboximidamide

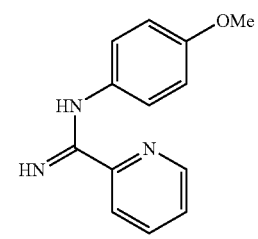

The title compound was prepared from 2-cyanopyridine (8.46 g, 81 mmol) and 4-methoxyaniline (10 g, 81 mmol) by following the procedure described in preparation 10 (16 g, yield 86.7%, mp 73-75° C., purity 97.6% by HPLC). $^1$H-NMR (CDCl$_3$):δ 3.81 (s, 3H), 5.5-6 (bs, 2H, D$_2$O exchangeable), 6.91-6.98 (m, 4H), 7.37-7.4 (m, 1H), 7.79-7.83 (m, 1H), 8.39-8.41 (d, 1H), 8.56-8.57 (d, 1H). IR (KBr) cm$^{-1}$: 3456, 3540, 3410, 1663. MS m/z:228.2 (M$^+$).

Preparation 32

N-(3,4-Dimethylphenyl)pyridine-2-carboximidamide

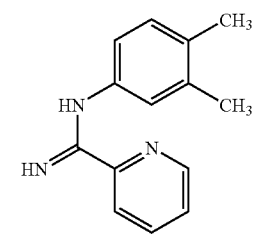

The title compound was prepared from 2-cyanopyridine (8.6 g, 83 mmol) and 3,4-dimethylaniline (10 g, 83 mmol) by following the procedure described in preparation 10 (13.2 g, yield 71.2%, mp 105-107° C., purity 99.9% by HPLC).

$^1$H-NMR (CDCl$_3$): δ 2.24-2.25 (d, 6H), 5.75-6 (bs, 2H, D$_2$O exchangeable), 6.75-6.81 (m, 2H), 7.11-7.13 (d, 1H), 7.36-7.39 (m, 1H), 7.78-7.82 (m, 1H) 8.39-8.41 (d, 1H), 8.55-8.57 (m, 1H). IR (KBr) cm$^{-1}$: 3445, 3303, 1645, 1625. MS m/z:227 (M$^+$).

Preparation 33

N-(4-Ethylphenyl)pyridine-2-carboximidamide

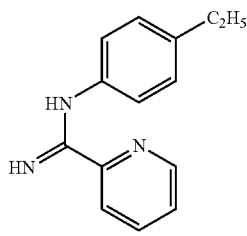

The title compound was prepared from 2-cyanopyridine (8.5 g, 82 mmol) and 4-ethylaniline (10 g, 82 mmol) by following the procedure described in preparation 10 (13.22 g, yield 71%, mp 75-77 C, purity 99.9% by HPLC). $^1$H-NMR (CDCl$_3$):δ 1.22-1.26 (t, 3H), 2.61-2.66 (q, 2H), 6.93-6.95 (d, 2H), 7.18-7.25 (m, 2H), 7.36-7.39 (m, 1H), 7.78-7.82 (m, 1H), 8.40-8.42 (d, 1H), 8.56-8.57 (d, 1H). MS m/z: 227.3 (M$^+$).

Preparation 34

N-(4-Methylphenyl)pyridine-2-carboximidamide

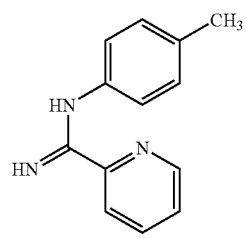

The title compound was prepared from 2-cyanopyridine (9.7 g, 93 mmol) and 4-methylaniline (10 g, 93 mmol) by following the procedure described in preparation 10 (8.2 g, yield 41.6%). MS m/z:212.1(M$^+$).

Preparation 35

N-(4-Ethoxyphenyl)pyridine-4-carboximidamide

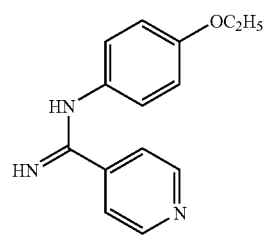

The title compound was prepared from 4-cyanopyridine (7.58 g, 72 mmol) and 4-ethoxyaniline (10 g, 72 mmol) by following the procedure described in preparation 10 (15.70 g, yield 89.3%, purity 99.4% by HPLC). MS m/z:242.3 (M$^+$).

Preparation 36

N-(4-Methylphenyl)pyridine-4-carboximidamide

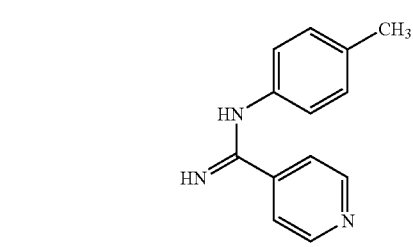

The title compound was prepared from 4-cyanopyridine (9.72 g, 93 mmol) and 4-methylaniline (10 g, 93 mmol) by following the procedure described in preparation 10 (14.3 g, yield 72.5%, mp 120-123° C., purity 98.75% by HPLC). $^1$H-NMR (CDCl$_3$):δ 2.33 (s, 3H), 5.06 (bs, 2H, D$_2$O exchangeable), 6.84-6.86 (d, 2H), 7.16-7.18 (d, 2H), 7.71-7.72 (d, 2H), 8.66-8.67 (d, 2H). IR (KBr) cm$^{-1}$: 3437, 3138, 1644. MS m/z:212.1 (M$^+$).

Preparation 37

N-(4-Isopropylphenyl)pyridine-4-carboximidamide

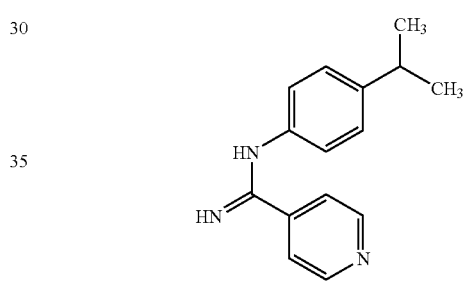

The title compound was prepared from 4-cyanopyridine (7.7 g, 74 mmol) and 4-isopropylaniline (10 g, 74 mmol) by following the procedure described in preparation 10 (16 g, yield 90.4%, mp 131-134 C, purity 96.43% by HPLC). $^1$H-NMR (DMSO): δ 1.20-1.22 (d, 6H), 2.82-2.87 (m, 1H), 6.54 (bs, 2H, D$_2$O exchangeable), 6.8-6.82 (d, 2H), 7.18-7.2 (d, 2H), 7.89-7.9 (d, 2H), 8.65-8.67 (d, 2H). IR (KBr) cm$^{-1}$: 3452, 3299, 3163, 2955, 1647, 1597. MS m/z:240.2 (M$^+$).

Preparation 38

N-(4-Ethylphenyl)pyridine-3-carboximidamide

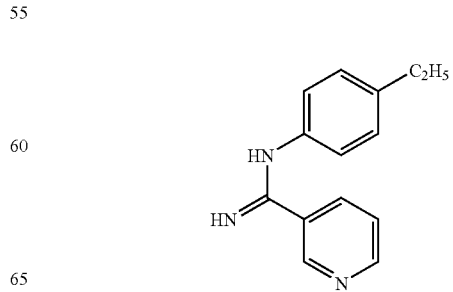

The title compound was prepared from 3-cyanopyridine (8.5 g, 83 mmol) and 4-ethylaniline (10 g, 83 mmol) by following the procedure described in preparation 10 (15.8 g, yield 84.9%, mp 134-136 C, purity 99.8% by HPLC). $^1$H-NMR (CDCl$_3$):δ 1.22-1.26 (t, 3H), 2.60-2.65 (q, 2H), 5.09 (bs, 2H, D$_2$O exchangeable), 6.88-6.89 (d, 2H), 7.18-7.19 (d, 2H), 7.32-7.35 (m, 1H), 8.18-8.20 (d, 1H), 8.64-8.65 (d, 1H), 9.03 (s, 1H). IR (KBr) cm$^{-1}$: 3302, 3108, 2965, 2928, 2844, 1655. MS m/z: 227.1 (M$^+$).

Preparation 39

N-(3,4-Dimethylphenyl)pyridine-3-carboximidamide

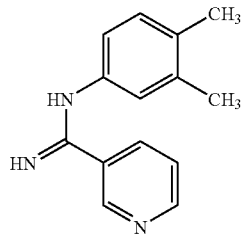

The title compound was prepared from 3-cyanopyridine (8.6 g, 83 mmol) and 3,4-dimetylaniline (10 g, 83 mmol) by following the procedure described in preparation 10 (15.6 g, yield 84%, mp 132-134 C, purity 99.7% by HPLC). $^1$H-NMR (CDCl$_3$):δ 2.24-2.26 (d, 6H), 4.92 (bs, 2H, D$_2$O exchangeable), 6.72-6.74 (d, 1H), 6.78 (s, 1H), 7.11-7.13 (d, 1H), 7.36-74 (m, 1H), 8.22-8.24 (d, 1H), 8.69-8.7 (d, 1H), 9.06 (d, 1H). IR (KBr) cm$^{-1}$: 3313, 3142, 2997, 2958, 2918, 1651. MS m/z:226.1 (M$^+$).

Preparation 40

N-(4-Methoxyphenyl)pyridine-3-carboximidamide

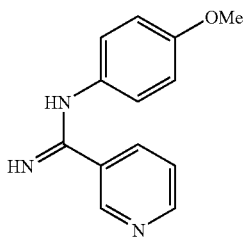

The title compound was prepared from 3-cyanopyridine (8.5 g, 83 mmol) and 4-methoxyaniline (10 g, 83 mmol) by following the procedure described in preparation 10 (11.6 g, yield 62.82%, mp 137-139° C., purity 97.2% by HPLC). $^1$H-NMR (CDCl$_3$):δ 3.81 (s, 3H), 4.94 (bs, 2H, D$_2$O exchangeable), 6.93 (s, 4H), 7.37-7.4 (d, 1H), 8.22-8.24 (d, 1H), 8.70-8.71 (d, 1H), 9.0 (s, 1H). IR (KBr) cm$^{-1}$: 3281, 3085, 3001, 2960, 2937, 1660. MS m/z:228.2 (M$^+$).

Preparation 41

N-(3,4-Dimethylphenyl)benzenecarboximidamide

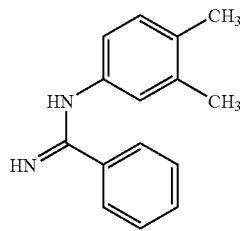

The title compound was prepared from benzonitrile (4.25 g, 41 mmol) and 3,4-dimethylaniline (5 g, 41 mmol) by following the procedure described in preparation 10 (7.2 g, yield 77.8%, purity 99.8% by HPLC). $^1$H-NMR (CDCl$_3$):δ 2.24-2.25 (d, 6H), 4.84 (bs, 2H, D$_2$O exchangeable), 6.73-6.75 (d, 1H), 6.79 (s, 1H), 7.1-7.11 (d, 1H), 7.41-7.49 (m, 3H), 7.86-7.88 (d, 2H). MS m/z:225.2 (M$^+$).

EXAMPLE 1

Synthesis of 5-cyano-2-(4-chlorophenyl)-4-(methylthio)-1-[4-(methylthio)phenyl]-6-oxo-1,6-dihydropyrimidine

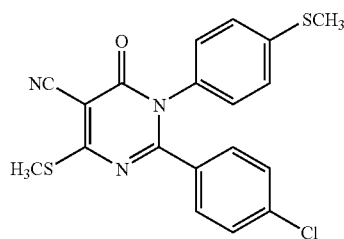

A mixture of ethyl 2-cyano-3,3-dimethylthioacrylate (1.345 g, 6.2 mmol) and 4-chloro-N-[4-(methylthio)phenyl]benzenecarboximidamide (1.7 g, 6.2 mmol) (obtained according to the procedure described in preparation 1) was heated at 110-120° C. for 2 hours. The gummy mass thus obtained was purified by column chromatography to give the title compound (1.1 g, yield 44.4%, purity 94.6% by HPLC), mp 206-207° C. $^1$H-NMR (CDCl$_3$):δ 2.47 (s, 3H), 2.66 (s, 3H), 6.99-7.01 (d, 2H), 7.18-7.30 (m, 6H). IR (KBr) cm$^{-1}$: 2218(—CN), 1672 (—C═O). MS m/z:400.1(M$^+$).

EXAMPLE 2

Synthesis of 5-cyano-2-(4-fluorophenyl)-4-(methylthio)-1-[4-(methylthio)phenyl]-6-oxo-1,6-dihydropyrimidine

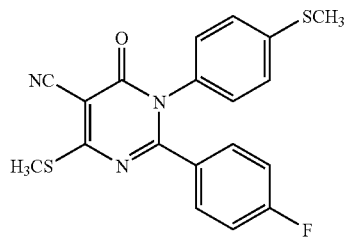

The title compound was prepared from ethyl 2-cyano-3, 3-dimethylthioacrylate (1.25 g, 5.76 mmol) and 4-fluoro-N-[4-(methylthio)phenyl]benzenecarboximidamide (1.50 g, 5.76 mmol) (obtained in preparation 2) according to the procedure described in example 1, (1.8 g, 81.8%, purity 99.4% by HPLC), mp 204-207° C. $^1$H-NMR (CDCl$_3$):δ 2.46 (s, 3H), 2.67 (s, 3H), 6.94-7.01 (m, 4H), 7.17-7.26 (m, 2H), 7.35-7.38 (m, 2H). IR (KBr) cm$^{-1}$: 2218(—CN), 1678 (—C═O). MS m/z:384 (M$^+$)

EXAMPLE 3

Synthesis of 5-cyano-2-phenyl-4-(methylthio)-1-[4-(methylthio)phenyl]-6-oxo-1,6-dihydropyrimidine

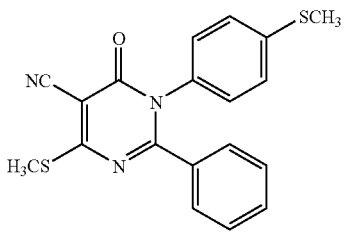

The title compound was prepared from ethyl 2-cyano-3,3-dimethylthioacrylate (1.345 g, 6.2 mmol) and N-[4-(methylthio)phenyl]benzenecarboximidamide (1.50 g, 6.2 mmol) (obtained in preparation 3) by following the procedure described in example 1, (1.28 g, yield 56.6%, purity 98.8% by HPLC), mp 204-205° C. $^1$H-NMR (CDCl$_3$):δ 2.45 (s, 3H), 2.67 (s, 3H), 6.99-7.01 (m, 2H), 7.15-7.17 (m, 2H), 7.26-7.37 (m, 5H). IR (KBr) cm$^{-1}$: 2218 (—CN), 1682 (—C=O). MS m/z:366 (M$^+$).

EXAMPLE 4

Synthesis of 5-cyano-2-(trifluoromethylphenyl)-4-(methylthio)-1-[4-(methylthio)phenyl]-6-oxo-1,6-dihydropyrimidine

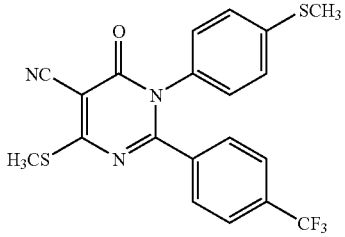

The title compound was prepared from ethyl 2-cyano-3,3-dimethylthioacrylate (1.0 g, 4.6 mmol) and the N-[4-(methylthio)phenyl]-4-(trifluoromethyl)benzenecarboximidamide (1.50 g, 4.8 mmol) (obtained according to the procedure described in preparation 4) by following the procedure described in example 1, (1.6 g, 80.1%, purity 99.3% by HPLC), mp 228-229° C. $^1$H-NMR (CDCl$_3$):δ 2.46 (s, 3H), 2.66 (s, 3H), 6.99-7.01 (d, 2H), 7.17-7.19 (d, 2H), 7.46-7.48 (d, 2H), 7.54-7.56 (d, 2H). IR (KBr) cm$^{-1}$: 2215 (—CN), 1680 (—C=O). MS m/z: 434.2 (M$^+$).

EXAMPLE 5

Synthesis of 5-cyano-2-[(4-methylthio)phenyl]-4-(methylthio)-1-[4-fluorophenyl]-6-oxo-1,6-dihydropyrimidine

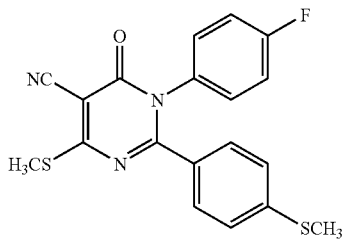

The title compound was prepared from ethyl 2-cyano-3,3-dimethylthioacrylate (0.334 g, 1.54 mmol) and N-(4-fluorophenyl)-4-(methylthio)benzenecarboximidamide (0.40 g, 1.54 mmol) (obtained in preparation 5) by following the procedure described in example 1, (0.32 g, 54.3%, purity 99.2% by HPLC), mp 219-221° C. $^1$H-NMR (CDCl$_3$):δ 2.46 (s, 3H), 2.68 (s, 3H), 7.05-7.12 (m, 6H), 7.23-7.27 (m, 2H). IR (KBr) cm$^{-1}$: 2218 (—CN), 1667 (—C=O). MS m/z:384 (M$^+$).

EXAMPLE 6

Synthesis of 5-cyano-1-(4-methylphenyl)-4-(methylthio)-2-[4-(methylthio)phenyl]-6-oxo-1,6-dihydropyrimidine

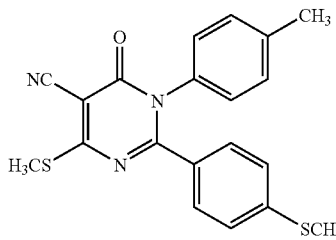

The title compound was prepared from ethyl 2-cyano-3,3-dimethylthioacrylate (0.848 g, 3.9 mmol) and N-(4-methylphenyl)-4-(methylthio)benzenecarboximidamide (1.0 g, 3.9 mmol) (obtained in preparation 6) by following the procedure described in example 1, (0.68 g, 46%, purity 99.3% by HPLC), mp 196-198° C. $^1$H-NMR (CDCl$_3$):δ 2.34 (s, 3H), 2.45 (s, 3H), 2.67 (s, 3H), 6.99-7.01 (m, 2H), 7.04-7.06 (m, 2H), 7.14-7.18 (m, 2H), 7.26-7.28 (m, 2H). IR (KBr) cm$^{-1}$: 2215 (—CN), 1688 (—C=O). MS m/z:380.4 (M$^+$).

EXAMPLE 7

Synthesis of 5-cyano-2-[(4-methylsulphonyl)phenyl]-4-(methylthio)-1-(4-methylphenyl)-6-oxo-1,6-dihydropyrimidine

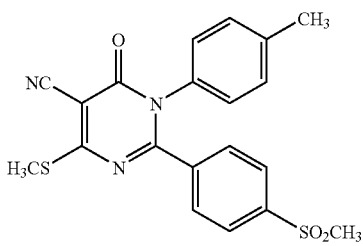

The title compound was prepared from ethyl 2-cyano-3,3-dimethylthioacrylate (0.378 g, 1.74 mmol) and N-(4-methylphenyl)-4-(methylsulfonyl)benzenecarboximidamide (0.5 g, 1.74 mmol) (obtained in preparation 8) according to the procedure described in example 1, (0.43 g, 59.6%, purity 99.1% by HPLC), mp 242-244° C. $^1$H-NMR (CDCl$_3$):δ 2.34 (s, 3H), 2.65 (s, 3H), 3.04 (s, 3H), 6.95-6.97 (d, 2H), 7.15-7.17 (d, 2H), 7.51-7.54 (d, 2H), 7.82-7.84 (d, 2H). IR (KBr) cm$^{-1}$: 2217 (—CN), 1696 (—C=O). MS m/z:412 (M$^+$).

EXAMPLE 8

Synthesis of 5-carboxy-2-[(4-methylthio)phenyl]-4-(methylthio)-1-(4-methylphenyl)-6-oxo-1,6-dihydropyrimidine

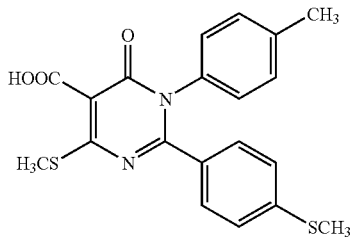

A mixture of 5-cyano-1-(4-methylphenyl)-4-(methylthio)-2-[4-(methylthio)phenyl]-6-oxo-1,6-dihydropyrimidine (2.5 g, 6.59 mmol) (obtained according to the procedure described in example 6) and potassium hydroxide (40%, 25 ml) solution was refluxed for 2 hours. The reaction mixture was poured onto ice-water, neutralised with dilute hydrochloric acid and filtered. The solid thus obtained was washed with water and dried to yield title compound (2.12 g, 80.8%, purity 91.6% by HPLC), mp 173-175° C. $^1$H-NMR (CDCl$_3$):δ 2.34 (s, 3H), 2.53 (s, 3H), 2.69 (s, 3H), 7.16-7.18 (d, 2H), 7.26-7.37 (m, 4H), 7.92-7.94 (d, 2H), 14.0 (s, 1H, D$_2$O exchangeable). IR (KBr) cm$^{-1}$: 3311(—COOH), 1702 (—C=O). MS m/z:398.5 (M$^+$).

EXAMPLE 9

Synthesis of 5-cyano-1-(4-isopropylphenyl)-4-(methylthio)-2-[4-(methylthio)phenyl]-6-oxo-1,6-dihydropyrimidine

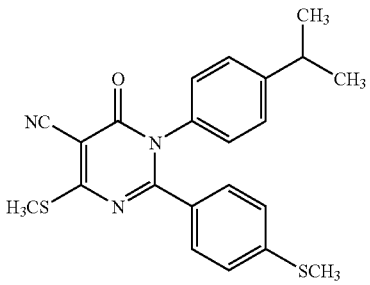

A mixture of ethyl 2-cyano-3,3-dimethylthioacrylate (3.8 g, 17.6 mmol) and N-(4-isopropylphenyl)-4-(methylthio)benzenecarboximidamide (5 g, 17 mmol) (obtained according to preparation 9) was heated at 110-120° C. for 3 hours. The crude solid was triturated with diethyl ether and filtered to give the title compound (1.22 g, yield 17.1%, mp 180-181° C., purity 99.29% by HPLC). $^1$H-NMR (CDCl$_3$):δ 1.21-1.23 (d, 6H), 2.44 (s, 3H), 2.67 (s, 3H), 2.9-2.92 (m, 1H), 7.02-7.04 (m, 4H), 7.2-7.26 (m, 4H). IR (KBr) cm$^{-1}$: 2920, 2955, 2215 (—CN), 1686 (—C=O). MS m/z:408.2 (M$^+$).

EXAMPLE 10

Synthesis of 5-cyano-1-(3,4-dimethylphenyl)-4-(methylthio)-2-[4-(methylthio)phenyl]-6-oxo-1,6-dihydropyrimidine

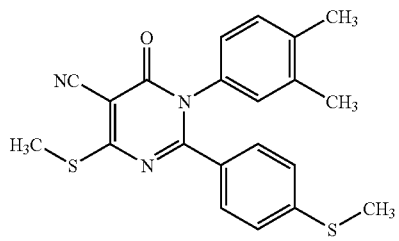

The title compound was prepared from ethyl 2-cyano-3,3-dimethylthioacrylate (6.59 g, 30.3 mmol) and N-(3,4-dimethylphenyl)-4-(methylthio)benzenecarboximidamide (8.2 g, 30.3 mmol) (obtained according to preparation 10) according to the procedure described in example 9 (10.8 g, yield 90.4%, mp 234-236° C., purity 99.77% by HPLC). $^1$H-NMR (CDCl$_3$):δ 2.2 (s, 3H), 2.24 (s, 3H), 2.45 (s, 3H), 2.66 (s, 3H), 6.78-6.8 (m, 1H), 6.92-6.93 (d, 1H), 7.03-7.10 (m, 3H), 7.26-7.29 (m, 2H). IR (KBr) cm$^{-1}$: 3436, 2972, 2922, 2213 (—CN), 1679 (—C=O). MS m/z:394.1(M$^+$).

EXAMPLE 11

Synthesis of 5-cyano-1-(4-isopropylphenyl)-2-[4-(methylsulfonyl)phenyl]-4-(methylthio)-6-oxo-1,6-dihydropyrimidine

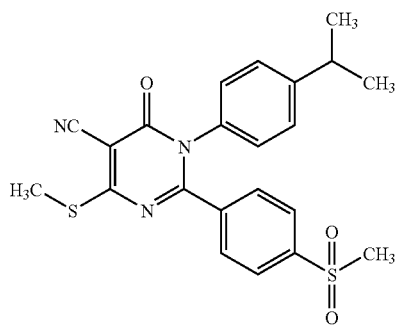

The title compound was prepared from ethyl 2-cyano-3,3-dimethylthioacrylate (1.37 g, 6 mmol) and N-(4-isopropylphenyl)-4-(methylsulfonyl)benzenecarboximidamide (2.0 g, 6 mmol) (obtained according to preparation 11) according to the procedure described in example 9 (1.82 g, yield 65.7%, mp 211-212° C., purity 95.24% by HPLC). $^1$H-NMR (CDCl$_3$):δ 1.19-1.21 (d, 6H), 2.66 (s, 3H), 2.87-2.90 (m, 1H), 3.01 (s, 3H), 6.99-7.01 (d, 2H), 7.19-7.21 (d, 2H), 7.51-7.53 (d, 2H), 7.81-7.83 (d, 2H). IR (KBr) cm$^{-1}$: 3435, 2961, 2929, 2221 (—CN), 1686 (—C=O). MS m/z: 440.1(M$^+$).

EXAMPLE 12

Synthesis of 5-cyano-1-(3,4-dimethylphenyl)-2-[4-(methylsulfonyl)phenyl]-4-(methylthio)-6-oxo-1,6-dihydropyrimidine

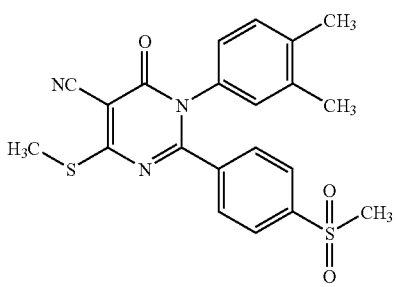

The title compound was prepared from ethyl 2-cyano-3,3-dimethylthioacrylate (2.68 g, 12.4 mmol) and N-(3,4-dimethylphenyl)-4-(methylsulfonyl)benzenecarboximidamide (3.75 g, 12.4 mmol) (obtained according to preparation 12) according to the procedure described in example 9 (1.9 g, yield 36.1%, mp 245-247° C., purity 99.24% by HPLC). $^1$H-NMR (CDCl$_3$):δ2.18 (s, 3H), 2.23 (s, 3H), 2.65 (s, 3H), 3.03 (s, 3H), 6.75-6.77 (m, 1H), 6.9-6.91 (d, 1H), 7.06-7.08 (d, 1H), 7.54-7.57 (d, 2H), 7.81-7.84 (d, 2H). IR (KBr) cm$^{-1}$: 3432, 2979, 2924, 2215 (—CN), 1693 (—C=O). MS m/z:426.0(M$^+$).

EXAMPLE 13

Synthesis of 5-cyano-1-(3,4,5-trimethoxyphenyl)-4-(methylthio)-2-[4-(methylthio)phenyl]-6-oxo-1,6-dihydropyrimidine

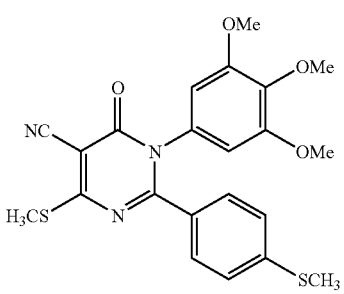

The title compound was prepared from ethyl 2-cyano-3,3-dimethylthioacrylate (0.57 g, 2.6 mmol) and N-(3,4,5-trimethoxyphenyl)-4-(methylthio)benzenecarboximidamide (0.87 g, 2.6 mmol) (obtained according to preparation 13) according to the procedure described in example 9 (0.48 g, yield 40.3%, mp 192-195° C., purity 97.52% by HPLC). $^1$H-NMR (CDCl$_3$):δ 2.45 (s, 3H), 2.67 (s, 3H), 3.71 (s, 6H), 3.84 (s, 3H), 6.35 (s, 2H), 7.06-7.08 (d, 2H), 7.30-7.32 (d, 2H). IR (KBr) cm$^{-1}$: 3436, 3078, 2216 (—CN), 1663 (—C=O). MS m/z:456.2 (M$^+$).

EXAMPLE 14

Synthesis of 5-cyano-1-(4-ethylphenyl)-4-(methylthio)-2-[4-(methylthio)phenyl]-6-oxo-1,6-dihydropyrimidine

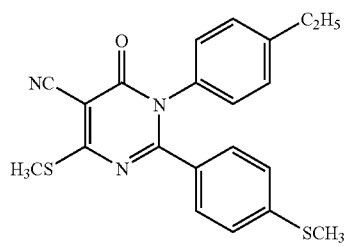

The title compound was prepared from ethyl 2-cyano-3,3-dimethylthioacrylate (16 g, 74 mmol) and N-(4-ethylphenyl)-4-(methylthio)benzenecarboximidamide (20 g, 74 mmol) (obtained according to preparation 14) according to the procedure described in example 9 (26 g, yield 89.2%, mp 223-225° C., purity 99.42% by HPLC). $^1$H-NMR (CDCl$_3$):δ 1.19-1.23 (t, 3H), 2.44 (s, 3H), 2.63-2.66 (q, 2H), 2.67 (s, 3H), 7.01-7.05 (m, 4H), 7.17-7.19 (d, 2H), 7.25-7.27 (m, 2H). IR (KBr) cm$^{-1}$: 3432, 2963, 2213 (—CN), 1689 (—C=O). MS m/z:394.1 (M$^+$).

EXAMPLE 15

Synthesis of 1-(4-bromophenyl)-5-cyano-4-(methylthio)-2-[4-(methylthio)phenyl]-6-oxo-1,6-dihydropyrimidine

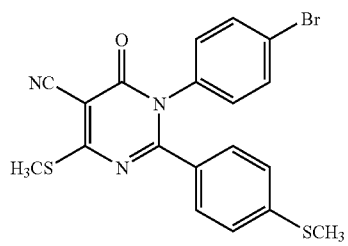

The title compound was prepared from ethyl 2-cyano-3,3-dimethylthioacrylate (0.36 g, 1.64 mmol) and N-(4-bromophenyl)-4-(methylthio)benzenecarboximidamide (0.53 g, 1.64 mmol) (obtained according to preparation 15) according to the procedure described in example 9 (0.4 g, yield 55%, mp 213-215° C., purity 99.0% by HPLC). $^1$H-NMR (CDCl$_3$):δ 2.46 (s, 3H), 2.67 (s, 3H), 7.0-7.02 (m, 2H), 7.06-7.09 (d, 2H), 7.22-7.26 (d, 2H), 7.5-7.52 (d, 2H). IR (KBr) cm$^{-1}$: 3432, 3091, 2926, 2213 (—CN), 1678 (—C=O). MS m/z:445.8 (M$^+$).

EXAMPLE 16

Synthesis of 5-cyano-1-(4-methoxyphenyl)-4-(methylthio)-2-[4-(methylthio)phenyl]-6-oxo-1,6-dihydropyrimidine

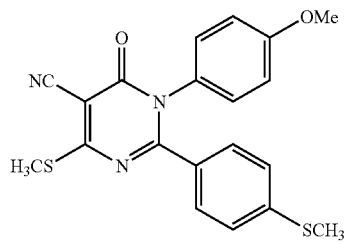

The title compound was prepared from ethyl 2-cyano-3,3-dimethylthioacrylate (5 g, 23 mmol) and N-(4-methoxyphenyl)-4-(methylthio)benzenecarboximidamide (6.27 g, 23 mmol) (obtained according to preparation 16) according to the procedure described in example 9 (7.2 g, yield 79.0%, mp 214-216° C., purity 97.42% by HPLC). $^1$H-NMR (CDCl$_3$):δ 2.49 (s, 3H), 2.71 (s, 3H), 3.84 (s, 3H), 6.89-6.92 (d, 2H), 7.06-7.11 (m, 4H), 7.30-7.32 (2H). IR (KBr) cm$^{-1}$: 3057, 2968, 2934, 2838, 2215 (—CN), 1687 (—C=O). MS m/z:396.1 (M$^+$).

EXAMPLE 17

Synthesis of 5-cyano-1-(4-fluorophenyl)-4-(methylthio)-2-phenyl-6-oxo-1,6-dihydropyrimidine

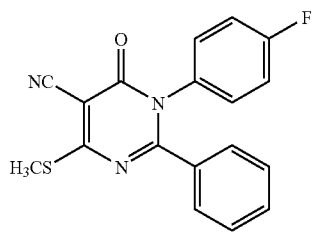

The title compound was prepared from ethyl 2-cyano-3,3-dimethylthioacrylate (5.0 g, 23 mmol) and N-(4-fluorophenyl)benzenecarboximidamide (4.93 g, 23 mmol) (obtained according to preparation 17) according to the procedure described in example 9 (6.5 g, yield 83.7%, mp 204-205° C., purity 99.7% by HPLC). $^1$H-NMR (CDCl$_3$):δ 2.67 (s, 3H), 7.01-7.11 (m, 4H), 7.26-7.58 (m, 5H). IR (KBr) cm$^{-1}$: 3421, 3059, 3021, 2211 (—CN), 1690(—C=O). MS m/z:338.1(M$^+$).

EXAMPLE 18

Synthesis of 1-(4-chlorophenyl)-5-cyano-4-(methylthio)-2-[4-(methylthio)phenyl]-6-oxo-1,6-dihydropyrimidine

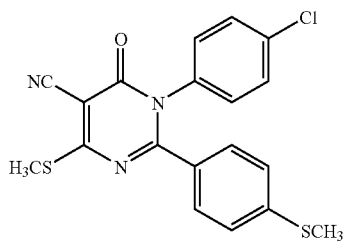

The title compound was prepared from ethyl 2-cyano-3,3-dimethylthioacrylate (0.313 g, 1.44 mmol) and N-(4-chlorophenyl)-4-(methylthio)benzenecarboximidamide (0.4 g, 1.44 mmol) (obtained according to preparation 18) according to the procedure described in example 9 (0.35 g, yield 61%, mp 203-205° C., purity 99.92% by HPLC). $^1$H-NMR (CDCl$_3$):δ 2.46 (s, 3H), 2.67 (s, 3H), 7.06-7.08 (m, 4H), 7.25-7.26 (d, 2H), 7.34-7.36 (d, 2H). IR (KBr) cm$^{-1}$: 3434, 3095, 2927, 2214 (—CN), 1678 (—C=O). MS m/z: 400.1 (M$^+$).

EXAMPLE 19

Synthesis of 5-cyano-1-(2,4-dimethylphenyl)-4-(methylthio)-2-[4-(methylthio)phenyl]-6-oxo-1,6-dihydropyrimidine

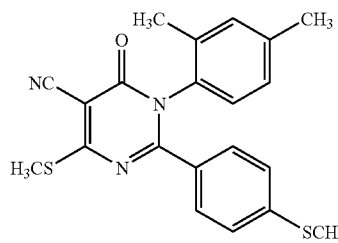

The title compound was prepared from ethyl 2-cyano-3,3-dimethylthioacrylate (7.22 g, 33.2 mmol) and N-(2,4-dimethylphenyl)-4-(methylthio)benzenecarboximidamide (9.0 g, 33.2 mmol) (obtained according to preparation 19) according to the procedure described in example 9 (10.6 g, yield 81%, mp 203-205° C., purity 99.4% by HPLC). $^1$H-NMR (DMSO):δ 1.94 (s, 3H), 2.21 (s, 3H), 2.38 (s, 3H), 2.62 (s, 3H), 6.97-7.13 (m, 5H), 7.28-7.30 (m, 2H). IR (KBr) cm$^{-1}$: 3435, 2922, 2212 (—CN), 1686 (—C=O). MS m/z:394.1 (M$^+$).

EXAMPLE 20

Synthesis of 5-cyano-2-(4-methylphenyl)-4-(methylthio)-1-[4-(methylthio)phenyl]-6-oxo-1,6-dihydropyrimidine

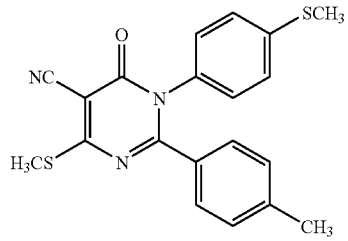

The title compound was prepared from ethyl 2-cyano-3,3-dimethylthioacrylate (1.69 g, 7.8 mmol) and 4-methyl-N-(4-methylthio)benzenecarboximidamide (2.0 g, 7.8 mmol) (obtained according to preparation 20) according to the procedure described in example 9 (2.5 g, yield 84.5%, mp 230-233° C., purity 99.54% by HPLC). $^1$H-NMR (CDCl$_3$):δ 2.32 (s, 3H), 2.46 (s, 3H), 2.66 (s, 3H), 7.0-7.07 (m, 4H), 7.16-7.26 (m, 4H). IR (KBr) cm$^{-1}$: 3433, 2922, 2213 (—CN), 1691 (—C=O). MS m/z:380.2 (M$^+$).

EXAMPLE 21

Synthesis of 5-cyano-1-(4-ethoxyphenyl)-4-(methylthio)-2-[4-(methylthio)phenyl]-6-oxo-1,6-dihydropyrimidine

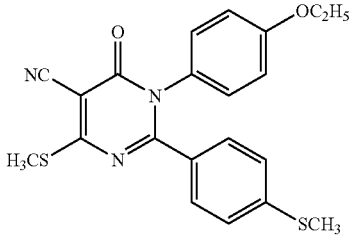

The title compound was prepared from ethyl 2-cyano-3, 3-dimethylthioacrylate (5.0 g, 23 mmol) and N-(4-ethoxyphenyl)-4-(methylthio)benzenecarboximidamide (6.59 g, 23 mmol) (obtained according to preparation 21) according to the procedure described in example 9 (7.5 g, yield 80%, mp 209-213° C., purity 99.11% by HPLC). $^1$H-NMR (CDCl$_3$):δ 1.39-1.56 (t, 3H), 2.45 (s, 3H), 2.66 (s, 3H), 3.98-4.03 (q, 2H), 6.83-6.86 (d, 2H), 6.99-7.06 (m, 4H), 7.25-7.27 (d, 2H). IR (KBr) cm$^{-1}$: 2926, 2216 (—CN), 1687(—C=O). MS m/z:410.2 (M$^+$).

EXAMPLE 22

Synthesis of 1-(4-tert-butylphenyl)-5-cyano-4-(methylthio)-2-[4-(methylthio)phenyl]-6-oxo-1,6-dihydropyrimidine

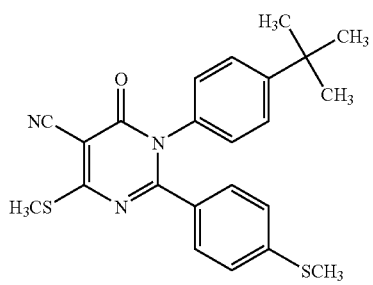

The title compound was prepared from ethyl 2-cyano-3, 3-dimethylthioacrylate (0.35 g, 1.67 mmol) and N-(4-tert-butylphenyl)-4-(methylthio)benzenecarboximidamide (0.5 g, 1.67 mmol) (obtained according to preparation 22) according to the procedure described in example 9 (0.46 g, yield 66%, mp 233-236° C., purity 99.28% by HPLC). $^1$H-NMR (CDCl$_3$):δ 1.29 (s, 9H), 2.44 (s, 3H), 2.67 (s, 3H), 7.01-7.04 (m, 4H), 7.24-7.26 (d, 2H), 7.36-7.38 (d, 2H). IR (KBr) cm$^{-1}$: 3431, 3052, 2955, 2217 (—CN), 1681 (—C=O). MS m/z:422.2 (M$^+$).

EXAMPLE 23

Synthesis of 5-cyano-1-(4-methylphenyl)-4-(methylthio)-6-oxo-2-phenyl-1,6-dihydropyrimidine

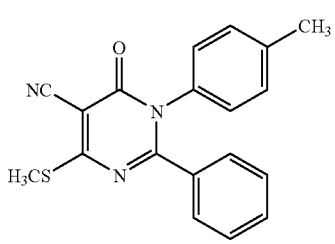

The title compound was prepared from ethyl 2-cyano-3, 3-dimethylthioacrylate (0.51 g, 2.4 mmol) and N-(4-methylphenyl)benzenecarboximidamide (0.5 g, 2.4 mmol) (obtained according to preparation 23) according to the procedure described in example 9 (0.61 g, yield 77.2%, mp 258-260° C., purity 99.73% by HPLC). $^1$H-NMR (CDCl$_3$):δ 2.32 (s, 3H), 2.66 (s, 3H), 6.96-6.98 (d, 2H), 7.12-7.14 (d, 2H), 7.22-7.35 (m, 5H). IR (KBr) cm$^{-1}$: 3061, 2932, 2213 (—CN), 1693 (—C=O). MS m/z: 334.2 (M$^+$).

EXAMPLE 24

Synthesis of 1-(4-n-butylphenyl)-5-cyano-4-(methylthio)-2-[4-(methylthio)phenyl]-6-oxo-1,6-dihydropyrimidine

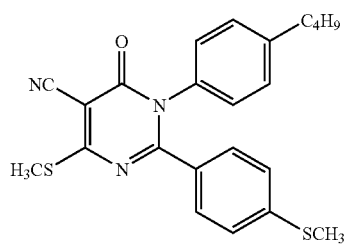

The title compound was prepared from ethyl 2-cyano-3, 3-dimethylthioacrylate (0.35 g, 1.67 mmol) and N-(4-butylphenyl)-4-(methylthio)benzenecarboximidamide (0.5 g, 1.67 mmol) (obtained according to preparation 24) according to the procedure described in example 9 (0.36 g, yield 53%, mp 138-141° C., purity 99.21% by HPLC). $^1$H-NMR (DMSO):δ 0.84-0.87 (m, 3H), 1.20-1.24 (m, 2H), 1.51-1.53 (m, 2H), 2.42 (s, 3H), 2.50-2.55 (m, 2H), 2.65 (s, 3H), 7.08-7.10 (m, 2H), 7.18-7.21 (m, 4H), 7.29-7.31 (m, 2H). IR (KBr) cm$^{-1}$: 2926, 2857, 2215 (—CN), 1687(—C=O). MS m/z:422.1 (M$^+$).

EXAMPLE 25

Synthesis of 5-cyano-1-(4-fluorophenyl)-4-(methylthio)-6-oxo-2-pyridin-4-yl-1,6-dihydropyrimidine

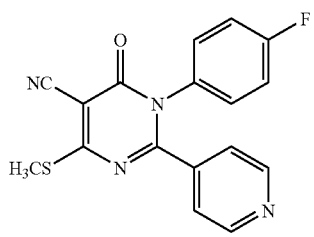

The title compound was prepared from ethyl 2-cyano-3, 3-dimethylthioacrylate (1.0 g, 4.6 mmol) and N-(4-fluorophenyl)pyridine-4-carboximidamide (1.0 g, 4.6 mmol) (obtained according to preparation 25) according to the procedure described in example 9 (0.72 g, yield 45.4%, mp 301-303° C., purity 99.86% by HPLC). $^1$H-NMR (DMSO):δ 2.64 (s, 3H), 7.2-7.24 (m, 2H), 7.35-7.36 (d, 2H), 7.43-7.46 (m, 2H), 8.54-8.55 (d, 2H). IR (KBr) cm$^{-1}$: 3433, 3072, 2214 (—CN), 1671, 1599 (—C=O). MS m/z:339.1(M$^+$).

EXAMPLE 26

Synthesis of 5-cyano-1-(4-fluorophenyl)-4-(methylthio)-6-oxo-2-pyridin-3-yl-1,6-dihydropyrimidine

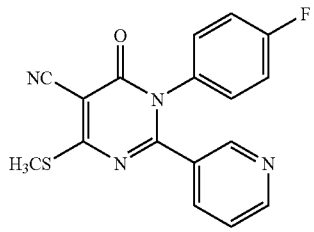

The title compound was prepared from ethyl 2-cyano-3,3-dimethylthioacrylate (0.5 g, 2.3 mmol) and N-(4-fluorophenyl)pyridine-3-carboximidamide (0.5 g, 2,3 mmol) (obtained according to preparation 26) according to the procedure described in example 9 (0.5 g, yield 63.6%, mp 190-193° C., purity 95.11% by HPLC). $^1$H-NMR (CDCl$_3$):δ 2.68 (s, 3H), 7.05-7.26 (m, 5H), 7.54-7.56 (d, 1H), 8.59-8.64 (m, 2H). IR (KBr) cm$^{-1}$: 3435, 3064, 3024, 2934, 2219 (—CN), 1667 (—C=O). MS m/z: 339.2(M$^+$).

EXAMPLE 27

Synthesis of 5-cyano-4-(methylthio)-1-[4-(methylthio)phenyl]-6-oxo-2-pyridin-3-yl-1,6-dihydropyrimidine

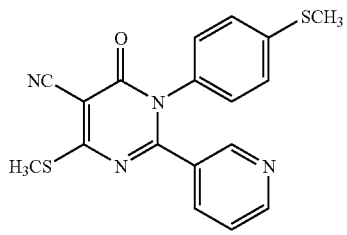

The title compound was prepared from ethyl 2-cyano-3,3-dimethylthioacrylate (2.2 g, 10.1 mmol) and N-[(4-methylthio)phenyl]pyridine-3-carboximidamide (2.4 g, 10.1 mmol) (obtained according to preparation 27) according to the procedure described in example 9 (1.7 g, yield 46.7%, mp 212-215° C., purity 99.8% by HPLC). $^1$H-NMR (CDCl$_3$):δ 2.45 (s, 3H), 2.67 (s, 3H), 7.01-7.03 (d, 2H), 7.17-7.22 (m, 3H), 7.57-7.59 (d, 1H), 8.58-8.59 (d, 1H), 8.66-8.67 (d, 1H). IR (KBr) cm$^{-1}$: 3433, 2925, 2217 (—CN), 1667 (—C=O). MS m/z:367.1 (M$^+$).

EXAMPLE 28

Synthesis of 5-cyano-4-(methylthio)-1-[4-(methylthio)phenyl]-6-oxo-2-pyridin-4-yl-1,6-dihydropyrimidine

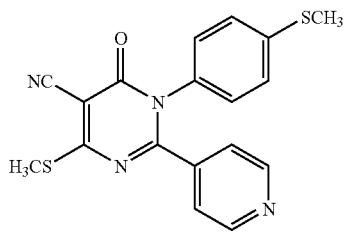

The title compound was prepared from ethyl 2-cyano-3,3-dimethylthioacrylate (1.67 g, 7.7 mmol) and N-[(4-methylthio)phenyl]pyridine-4-carboximidamide (1.87 g, 7.7 mmol) (obtained according to preparation 28) according to the procedure described in example 9 (2.0 g, yield 71.4%, mp 227-229° C., purity 98.67% by HPLC). $^1$H-NMR (CDCl$_3$):δ 2.44 (s, 3H), 2.66 (s, 3H), 6.98-7.0 (d, 2H), 7.15-7.26 (m, 4H), 8.57-8.58 (d, 2H). IR (KBr) cm$^{-1}$: 2923, 2216 (—CN), 1668 (—C=O). MS m/z:367.0 (M$^+$).

EXAMPLE 29

Synthesis of 5-cyano-1-(4-fluorophenyl)-4-(methylthio)-6-oxo-2-pyridin-2-yl-1,6-dihydropyrimidine

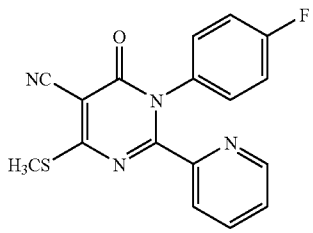

The title compound was prepared from ethyl 2-cyano-3,3-dimethylthioacrylate (1.1 g, 5.11 mmol) and N-(4-fluorophenyl)pyridine-2-carboximidamide (1.1 g, 5.11 mmol) (obtained according to preparation 29) according to the procedure described in example 9 (0.47 g, yield 27.4%, mp 221-227° C., purity 99.85% by HPLC). $^1$H-NMR (CDCl$_3$):δ 2.68 (s, 3H), 6.95-7.0 (m, 2H), 7.07-7.1 (m, 2H), 7.25-7.26 (m, 1H), 7.73-7.76 (m, 2H), 8.3-8.31 (d, 1H). IR (KBr) cm$^{-1}$: 3337, 3066, 2221 (—CN), 1676 (—C=O). MS m/z:339.1 (M$^+$).

EXAMPLE 30

Synthesis of 5-cyano-4-(methylthio)-1-[4-(methylthio)phenyl]-6-oxo-2-pyridin-2-yl-1,6-dihydropyrimidine

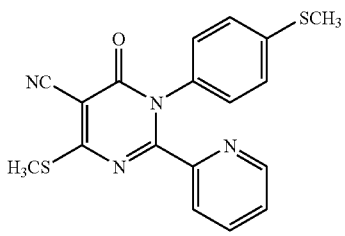

The title compound was prepared from ethyl 2-cyano-3,3-dimethylthioacrylate (1.8 g, 8.2 mmol) and N-[(4-methylthio)phenyl]pyridine-2-carboximidamide (2 g, 8.2 mmol) (obtained according to preparation 30) according to the procedure described in example 9 (1.2 g, yield 39.2%, mp 158-161° C., purity 98.8% by HPLC). $^1$H-NMR (CDCl$_3$):δ 2.43 (s, 3H), 2.67 (s, 3H), 6.98-7.01 (d, 2H), 7.1-7.12 (d, 2H), 7.65-7.67 (d, 1H), 7.72-7.74 (d, 2H), 8.33-8.34 (d, 1H). IR (KBr) cm$^{-1}$: 3370, 2922, 2216 (—CN), 1689 (—C=O). MS m/z:367.1 (M$^+$).

EXAMPLE 31

Synthesis of 5-cyano-4-(methylthio)-1-(4-methoxyphenyl)-6-oxo-2-pyridin-2-yl-1,6-dihydropyrimidine The title compound was prepared from ethyl 2-cyano-3,3-dimethylthioacrylate (15.6 g, 72 mmol) and N-(4-methoxyphenyl)pyridine-2-carboximidamide (16.32 g, 72 mmol) (obtained according to preparation 31) according to the procedure described in example 9 (13.0 g, yield 51.7%, mp 246-253° C., purity 94.57% by HPLC). $^1$H-NMR (CDCl$_3$):δ 2.66 (s, 3H), 3.75 (s, 3H), 6.77-6.79 (d, 2H), 6.99-7.01 (d, 2H), 7.23-7.26 (m, 1H), 7.59-7.61 (d, 1H), 7.72-7.73 (m, 1H), 8.35-8.37 (d, 1H). IR (KBr) cm$^{-1}$: 3431, 3060, 2217 (—CN), 1682 (—C=O). MS m/z:351.4 (M$^+$).

EXAMPLE 32

Synthesis of 5-cyano-4-(methylthio)-1-(3,4-dimethylphenyl)-6-oxo-2-pyridin-2-yl-1,6-dihydropyrimidine

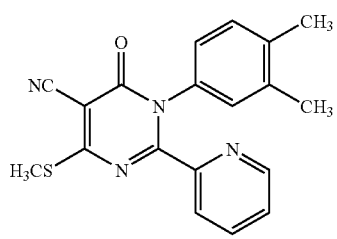

The title compound was prepared from ethyl 2-cyano-3,3-dimethylthioacrylate (13.9 g, 64 mmol) and N-(3,4-dimethylphenyl)pyridine-2-carboximidamide (14.5 g, 64 mmol) (obtained according to preparation 32) according to the procedure described in example 9 (14.5 g, yield 65%, mp 218-223° C., purity 98.7% by HPLC). $^1$H-NMR (CDCl$_3$):δ 2.15 (s, 3H), 2.18 (s, 3H), 2.66 (s, 3H), 6.76-6.78 (d, 1H), 6.90-6.91(d, 1H), 6.99-7.01 (d, 1H), 7.22-7.26 (m, 1H), 7.56-7.58 (d, 1H), 7.69-7.71 (m, 1H), 8.35-8.36 (d, 1H). IR (KBr) cm$^{-1}$: 3428, 2917, 2216 (—CN), 1686 (—C=O). MS m/z:349.2 (M$^+$).

EXAMPLE 33

Synthesis of 5-cyano-4-(methylthio)-1-(4-ethylphenyl)-6-oxo-2-pyridin-2-yl-1,6-dihydropyrimidine

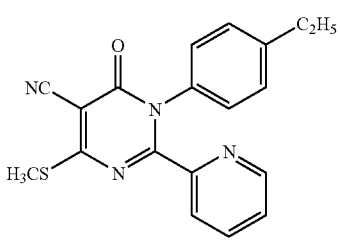

The title compound was prepared from ethyl 2-cyano-3,3-dimethylthioacrylate (14.85 g, 68.4 mmol) and N-(4-ethylphenyl)pyridine-2-carboximidamide (15.4 g, 68.4 mmol) (obtained according to preparation 33) according to the procedure described in example 9 (13.0 g, yield 54.5%, mp 172-175° C., purity 98.45% by HPLC). $^1$H-NMR (CDCl$_3$):δ 1.15-1.19 (t, 3H), 2.56-2.61 (q, 2H), 2.66 (s, 3H), 6.98-7.0 (d, 2H), 7.09-7.11 (d, 2H), 7.22-7.26 (m, 1H), 7.59-7.61 (d, 1H), 7.69-7.71 (m, 1H), 8.32-8.34 (d, 1H). IR (KBr) cm$^{-1}$: 3432, 2966, 2928, 2215 (—CN), 1680 (—C=O). MS m/z:349.2 (M$^+$).

EXAMPLE 34

Synthesis of 5-cyano-4-(methylthio)-1-(4-methylphenyl)-6-oxo-2-pyridin-2-yl-1,6-dihydropyrimidine

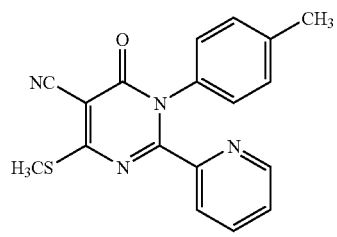

The title compound was prepared from ethyl 2-cyano-3,3-dimethylthioacrylate (2.1 g, 9.4 mmol) and N-(4-methylphenyl)pyridine-2-carboximidamide (2.0 g, 9.4 mmol) (obtained according to preparation 34) according to the procedure described in example 9 (1.2 g, yield 37.9%, mp 247-248° C., purity 99.89% by HPLC). $^1$H-NMR (CDCl$_3$):δ 2.29 (s, 3H), 2.66 (s, 3H), 6.96-6.98 (m, 2H), 7.06-7.08 (m, 2H), 7.21-7.26 (m, 1H), 7.6-7.62 (d, 1H), 7.7-7.73 (m, 1H), 8.33-8.34 (d, 1H). IR (KBr) cm$^{-1}$: 3433, 2921, 2216 (—CN), 1683 (—C=O). MS m/z:335.0 (M$^+$).

EXAMPLE 35

Synthesis of 5-cyano-4-(methylthio)-1-(4-ethoxyphenyl)-6-oxo-2-pyridin-4-yl-1,6-dihydropyrimidine

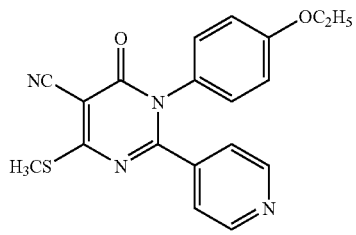

The title compound was prepared from ethyl 2-cyano-3,3-dimethylthioacrylate (2.3 g, 10 mmol) and N-(4-ethoxyphenyl)pyridine-4-carboximidamide (2.5 g, 10 mmol) (obtained according to preparation 35) according to the procedure described in example 9 (1.3 g, yield 34.4%, mp 201-204° C., purity 99.93% by HPLC). $^1$H-NMR (CDCl$_3$):δ 1.37-1.4 (t, 3H), 2.65 (s, 3H), 3.94-3.99 (q, 2H), 6.8-6.82 (d, 2H), 6.97-6.99 (d, 2H), 7.19-7.2 (d, 2H), 8.55-8.56 (d, 2H). IR (KBr) cm$^{-1}$: 2984, 2925, 2213 (—CN), 1673 (—C=O). MS m/z:365.1 (M$^+$).

EXAMPLE 36

Synthesis of 5-cyano-4-(methylthio)-1-(4-methylphenyl)-6-oxo-2-pyridin-4-yl-1,6-dihydropyrimidine

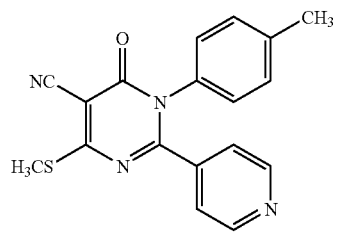

The title compound was prepared from ethyl 2-cyano-3,3-dimethylthioacrylate (1.6 g, 7.2 mmol) and N-(4-methylphenyl)pyridine-4-carboximidamide (1.5 g, 7.2 mmol) (obtained according to preparation 36) according to the procedure described in example 9 (2.0 g, yield 81.3%, mp >250° C., purity 99.28% by HPLC). $^1$H-NMR (CDCl$_3$):δ 2.33 (s, 3H), 2.66 (s, 3H), 6.96-6.98 (d, 2H), 7.14-7.17 (m, 4H), 8.55 (d, 2H). IR (KBr) cm$^{-1}$: 3430, 3032, 2925, 2213 (—CN), 1678 (—C═O). MS m/z:335.1 (M$^+$).

EXAMPLE 37

Synthesis of 5-cyano-4-(methylthio)-1-(4-isopropylphenyl)-6-oxo-2-pyridin-4-yl-1,6-dihydropyrimidine

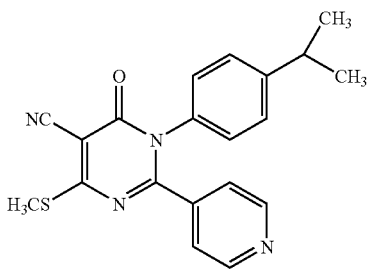

The title compound was prepared from ethyl 2-cyano-3,3-dimethylthioacrylate (1.8 g, 8.4 mmol) and N-(4-isopropylphenyl)pyridine-4-carboximidamide (2 g, 8.4 mmol) (obtained according to preparation 37) according to the procedure described in example 9 (1.63 g, yield 53.8%, mp 173-175° C., purity 99.74% by HPLC). $^1$H-NMR (CDCl$_3$):δ 1.19-1.21 (d, 6H), 2.66 (s, 3H), 2.87-2.9 (m, 1H), 6.99-7.01 (d, 2H), 7.17-7.26 (m, 4H), 8.53-8.55 (d, 2H). IR (KBr) cm$^{-1}$: 3434, 2965, 2218 (—CN), 1674 (—C═O). MS m/z:363.1 (M$^+$).

EXAMPLE 38

Synthesis of 5-cyano-4-(methylthio)-1-(4-ethylphenyl)-6-oxo-2-pyridin-3-yl-1,6-dihydropyrimidine

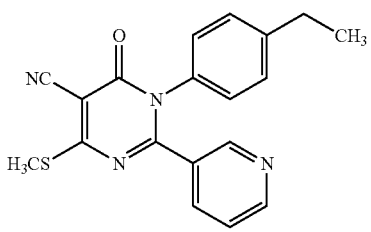

The title compound was prepared from ethyl 2-cyano-3,3-dimethylthioacrylate (1.5 g, 6.7 mmol) and N-(4-ethylphenyl)pyridine-3-carboximidamide (1.5 g, 6.7 mmol) (obtained according to preparation 38) according to the procedure described in example 9 (1.7 g, yield 73.3%, mp 207-209° C., purity 99.34% by HPLC). $^1$H-NMR (CDCl$_3$):δ 1.18-1.22 (t, 3H), 2.6-2.66 (q, 2H), 2.67 (s, 3H), 7.01-7.03 (d, 2H), 7.16-7.21 (m, 3H), 7.54-7.57 (d, 1H), 8.56-8.57 (d, 1H), 8.65-8.66 (d, 1H). IR (KBr) cm$^{-1}$: 3406, 2967, 2214 (—CN), 1694 (—C═O). MS m/z:349.2 (M$^+$).

EXAMPLE 39

Synthesis of 5-cyano-4-(methylthio)-1-(3,4-dimethylphenyl)-6-oxo-2-pyridin-3-yl-1,6-dihydropyrimidine

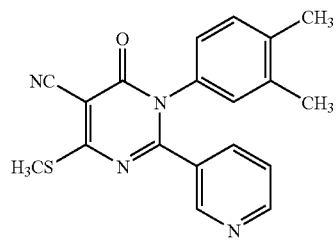

The title compound was prepared from ethyl 2-cyano-3,3-dimethylthioacrylate (1.93 g, 8.9 mmol) and N-(3,4-dimethylphenyl)pyridine-3-carboximidamide (2 g, 8.9 mmol) (obtained according to preparation 39) according to the procedure described in example 9 (2.4 g, yield 77.4%, mp >250° C., purity 99.8% by HPLC). $^1$H-NMR (CDCl$_3$):δ 2.19 (s, 3H), 2.23 (s, 3H), 2.67 (s, 3H), 6.78-6.8 (d, 1H), 6.92-6.93 (d, 1H), 7.09-7.11 (d, 1H), 7.18-7.21 (d, 1H), 7.6-7.62 (d, 1H), 8.56-8.64 (dd, 2H). IR (KBr) cm$^{-1}$: 3427, 2930, 2215 (—CN), 1688 (—C═O). MS m/z:349.1 (M$^+$).

EXAMPLE 40

Synthesis of 5-cyano-4-(methylthio)-1-(4-methoxyphenyl)-6-oxo-2-pyridin-3-yl-1,6-dihydropyrimidine

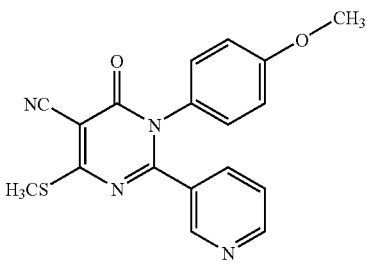

The title compound was prepared from ethyl 2-cyano-3,3-dimethylthioacrylate (1.5 g, 6.7 mmol) and N-(4-methoxyphenyl)pyridine-3-carboximidamide (1.5 g, 6.7 mmol) (obtained according to preparation 40) according to the procedure described in example 9 (1.4 g, yield 60.6%, mp 230-233° C., purity 99.75% by HPLC). $^1$H-NMR (CDCl$_3$):δ 2.67 (s, 3H), 3.79 (s, 3H), 6.85-6.88 (d, 2H), 7.01-7.04 (d, 2H), 7.20-7.21 (d, 1H), 7.56-7.58 (d, 1H), 8.57-8.58 (d, 2H). IR (KBr) cm$^{-1}$: 3054, 3009, 2836, 2213 (—CN), 1691 (—C═O). MS m/z:351.2 (M$^+$).

EXAMPLE 41

Synthesis of ethyl 1-(4-methylphenyl)-4-(methylthio)-2-[4-(methylthio)phenyl]-6-oxo-1,6-dihydropyrimidine-5-carboxylate

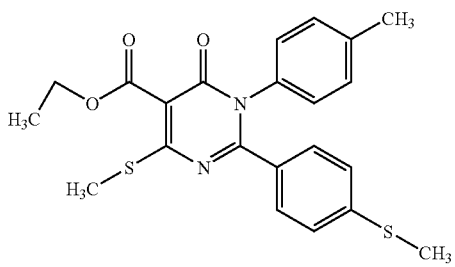

A mixture of diethyl [bis(methylthio)methylene]malonate (2.64 g, 10 mmol) and N-(4-methylphenyl)-4-(methylthio)benzenecarboximidamide (2.6 g, 10 mmol) (prepared according to the procedure described in preparation 6) was heated at 110-120° C. for 2 hours. The gummy mass thus obtained was purified by column chromatography to give the title compound (0.86 g, yield 20.2%, mp 153-155° C., purity 99.81% by HPLC). $^1$H-NMR (CDCl$_3$):δ 1.36-1.39 (t, 3H), 2.33 (s, 3H), 2.44 (s, 3H), 2.55 (s, 3H), 4.37-4.42 (q, 2H), 7.0-7.05 (m, 4H), 7.13-7.15 (d, 2H), 7.25-7.27 (d, 2H). IR (KBr) cm$^{-1}$: 2981, 2924, 1693 (—C=O). MS m/z:427.1 (M$^+$)

EXAMPLE 42

Synthesis of ethyl 1-(4-fluorophenyl)-4-(methylthio)-2-[4-(methylthio)phenyl]-6-oxo-1,6-dihydropyrimidine-5-carboxylate

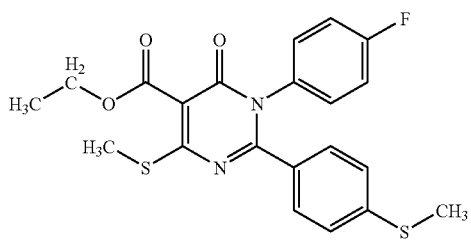

The title compound was prepared from diethyl [bis(methylthio)methylene]malonate (0.88 g, 3.3 mmol) and N-(4-fluorophenyl)-4-(methylthio)benzenecarboximidamide (0.87 g, 3.3 mmol) (prepared according to the procedure described in preparation 5) by following the procedure described in example 41 (0.22 g, yield 15.7%, mp 151-155° C., purity 99.72% by HPLC). $^1$H-NMR (CDCl$_3$):δ 1.37-1.40 (t, 3H), 2.45 (s, 3H), 2.55 (s, 3H), 4.38-4.43 (q, 2H), 7.02-7.07 (m, 4H), 7.11-7.14 (m, 2H), 7.22-7.26 (m, 2H). IR (KBr) cm$^{-1}$: 3360, 3072, 2978, 2924, 1694 (—C=O). MS m/z:431.2 (M$^+$).

EXAMPLE 43

Synthesis of ethyl 2-(4-fluorophenyl)-4-(methylthio)-1-[4-(methylthio)phenyl]-6-oxo-1,6-dihydropyrimidine-5-carboxylate

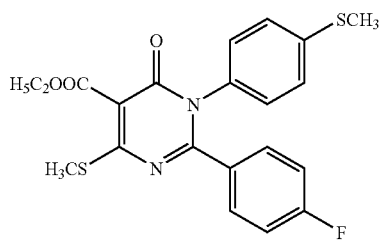

The title compound was prepared from diethyl [bis(methylthio)methylene]malonate (5.3 g, 20 mmol) and N-(4-methythiophenyl)-4-(fluoro)benzenecarboximidamide (5.2 g, 20 mmol) (prepared according to the procedure described in preparation 2) by following the procedure described in example 41 (0.25 g, yield 2.9%, mp 166-169° C., purity 96.84% by HPLC). $^1$H-NMR (CDCl$_3$):δ 1.36-1.4 (t, 3H), 2.45 (s, 3H), 2.55 (s, 3H), 4.38-4.43 (q, 2H), 6.91-6.96 (m, 2H), 7.01-7.03 (d, 2H), 7.16-7.18 (d, 2H), 7.33-7.37 (m, 2H). IR (KBr) cm$^{-1}$: 3447, 3069, 2989, 2900, 1733, 1666. MS m/z:431.2.0(M$^+$).

EXAMPLE 44

Synthesis of 5-carboxamido-1-(4-methylphenyl)-4-(methylsulfonyl)-2-[4-(methylsulfonyl)phenyl]-6-oxo-1,6-dihydropyrimidine

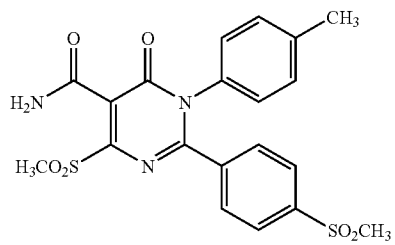

A suspension of 5-cyano-1-(4-methylphenyl)-4-(methylthio)-2-[4-(methylthio)phenyl]-6-oxo-1,6-dihydropyrimidine (5.0 g, 12.5 mmol) (prepared according to the procedure disclosed in example 6) in glacial acetic acid (30 ml) was treated with hydrogen peroxide (30 ml, 30% v/v) dropwise under stirring at 60° C. for 4 hrs. Then the reaction mass poured on to ice and the resulted solid filtered, washed thoroughly with water. The resulted solid purified from dichloromethane and methanol mixture (2.3 g, yield 39.9%, mp 260-262° C., purity 95.72% by HPLC). $^1$H-NMR (DMSO):δ 2.26 (s, 3H), 3.20 (s, 3H), 3.28 (s, 3H), 7.20 (s, 4H), 7.64-7.66 (d, 2H), 7.73 (s, 1H, D$_2$O exchangeable), 7.78 (s, 1H, D$_2$O exchangeable), 7.83-7.85 (d, 2H). IR (KBr) cm$^{-1}$: 3393, 3290, 3245, 3164, 3020, 2921, 1685 (—C=O), 1668(—C=O). MS m/z:462.2 (M$^+$).

EXAMPLE 45

Synthesis of 5-carboxamido-1-(4-methylphenyl)-2-[4-(methylsulfonyl)phenyl]-6-oxo-4-piperazin-1-yl-1,6-dihydropyrimidine

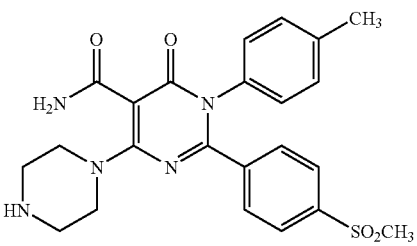

The title compound was prepared from 5-carboxamido-1-(4-methylphenyl)-4-(methylsulfonyl)-2-[4-(methylsulfonyl)phenyl]-6-oxo-1,6-dihydropyrimidine (0.5 g, 1.1 mmol) (obtained in example 44) by refluxing with piperazine (0.1 g, 1.2 mmol) in ethanol (20 ml) for 2 hrs. The resultant reaction mixture was filtered to yield the compound (0.4 g, yield 75.09%, mp 269-275° C., purity 94.87% by HPLC). $^1$H-NMR (CDCl$_3$):δ 2.33 (s, 3H), 3.03 (s, 3H), 3.84 (bs, 8H), 5.55 (s, 1H, D$_2$O exchangeable), 6.99-7.02 (d, 2H), 7.14-

7.16 (d, 2H), 7.51-7.53 (d, 2H), 7.80-7.82 (d, 2H), 8.73 (s, 1H, D$_2$O exchangeable). IR (KBr) cm$^{-1}$: 3399, 2924, 1645 (—C═O). MS m/z:468.2 (M$^+$).

EXAMPLE 46

Synthesis of 5-carboxamido-4-(methylamino)-1-(4-methylphenyl)-2-[4-(methylsulfonyl)phenyl]-6-oxo-1,6-dihydropyrimidine

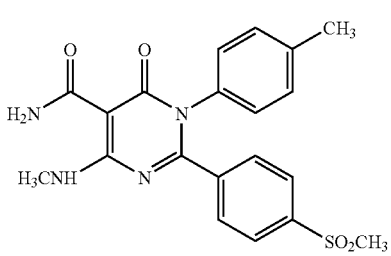

The title compound was prepared from 5-carboxamido-1-(4-methylphenyl)-4-(methylsulfonyl)-2-[4-(methylsulfonyl)phenyl]-6-oxo-1,6-dihydropyrimidine (0.3 g, 0.7 mmol) (obtained in example 44) by refluxing with methylamine (0.1 g, 3.3 mmol) in ethanol (15 ml) according to the procedure described in example 45 (0.25, yield 93.3%, mp >300° C., purity 98.59% by HPLC). $^1$H-NMR (CDCl$_3$):δ 2.32 (s, 3H), 3.02 (s, 3H), 3.13-3.14 (d, 3H), 5.43 (s, 1H, D$_2$O exchangeable), 6.96-6.98 (d, 2H), 7.12-7.14 (d, 2H), 7.52-7.54 (d, 2H), 7.79-7.81 (d, 2H), 8.75 (s, 1H, D$_2$O exchangeable). IR (KBr) cm$^{-1}$: 3320, 3155, 3020, 2926, 1656, 1607(—C═O). MS m/z: 413.3 (M$^+$).

EXAMPLE 47

Synthesis of 5-carboxamido-1-(4-methylphenyl)-2-[4-(methylsulfonyl)phenyl]-4-morpholin-4-yl-6-oxo-1,6-dihydropyrimidine

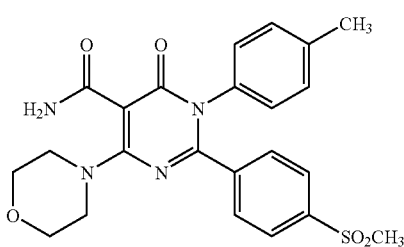

The title compound was prepared from 5-carboxamido-1-(4-methylphenyl)-4-(methylsulfonyl)-2-[4-(methylsulfonyl)phenyl]-6-oxo-1,6-dihydropyrimidine (0.5 g, 1.1 mmol) (obtained in example 44) by refluxing with morpholine (0.1 g, 1.2 mmol) in ethanol (15 ml) according to the procedure described in example 45 (0.36, yield 72%, mp 226-228° C., purity 98.86% by HPLC). $^1$H-NMR (CDCl$_3$):δ 2.33 (s, 3H), 3.02 (s, 3H), 3.79-3.82 (m, 8H), 5.52 (s, 1H, D$_2$O exchangeable), 6.98-7.0 (d, 2H), 7.13-7.15 (d, 2H), 7.49-7.51 (d, 2H), 7.79-7.81 (d, 2H), 8.72 (s, 1H, D$_2$O exchangeable). IR (KBr) cm$^{-1}$: 3440, 3319, 2965, 2927, 2857, 1658 (—C═O). MS m/z: 469.2 (M$^+$).

EXAMPLE 48

Synthesis of 5-carboxamido-2-(4-fluorophenyl)-4-(methylsulfonyl)-1-[4-(methylsulfonyl)phenyl]-6-oxo-1,6-dihydropyrimidine

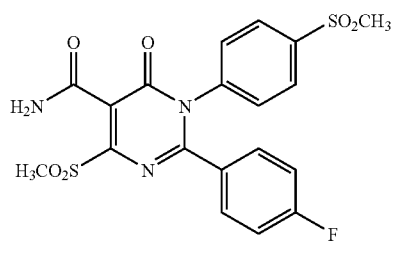

The title compound was prepared from 5-cyano-2-(4-fluorophenyl)-1-[4-(methylthio)phenyl]-4-(methylthio)-6-oxo-1,6-dihydropyrimidine (2.5 g, 6.5 mmol, prepared according to the procedure disclosed in example 2) according to the procedure described in example 44 (1.5 g, yield 49.2%, mp 237-241° C., purity 93.95% by HPLC). $^1$H-NMR (DMSO):δ 3.20 (s, 3H), 3.27 (s, 3H), 7.14-7.19 (m, 2H), 7.42-7.46 (m, 2H), 7.61-7.63 (m, 2H), 7.75 (s, 2H, D$_2$O exchangeable), 7.94-7.97 (m, 2H). IR (KBr) cm$^{-1}$: 3416, 3012, 2923, 1681 (—C═O). MS m/z:466.1 (M$^+$).

EXAMPLE 49

Synthesis of 5-carboxamido-2-(4-fluorophenyl)-4-(methylamino)-1-[4-(methylsulfonyl)phenyl]-6-oxo-1,6-dihydropyrimidine

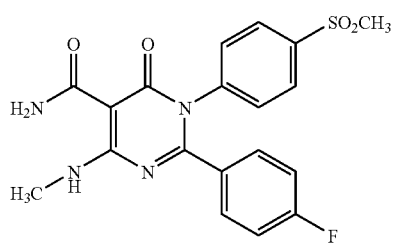

The title compound was prepared from 5-carboxamido-2-(4-fluorophenyl)-4-(methylsulfonyl)-1-[4-(methylsulfonyl)phenyl]-6-oxo-1,6-dihydropyrimidine (0.75 g, 1.6 mmol) (obtained in example 48) by refluxing with methylamine (1 g, 13 mmol) in ethanol (15 ml) according to the procedure described in example 45 (0.35, yield 52.3%, mp >300° C., purity 96.54% by HPLC). $^1$H-NMR (DMSO):δ 3.04-3.05 (d, 3H), 3.21 (s, 3H), 7.10-7.14 (m, 2H), 7.33-7.34 (d, 1H, D$_2$O exchangeable), 7.41-7.45 (m, 2H), 7.58-7.60 (d, 2H), 7.85-7.87 (d, 2H), 8.91-8.92 (d, 1H, D$_2$O exchangeable), 10.58-10.59 (d, 1H, D$_2$O exchangeable). IR (KBr) cm$^{-1}$: 3442, 3368, 3296, 3107, 3009, 2916, 1662 (—C═O). MS m/z:417.2 (M$^+$).

EXAMPLE 50

Synthesis of 5-carboxamido-2-(4-fluorophenyl)-1-[4-(methylsulfonyl)phenyl]-4-morpholin-4-yl-6-oxo-1,6-dihydropyrimidine

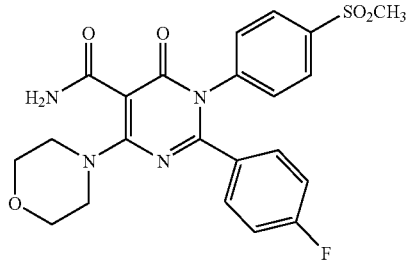

The title compound was prepared from 5-carboxamido-2-(4-fluorophenyl)-4-(methylsulfonyl)-1-[4-(methylsulfonyl)phenyl]-6-oxo-1,6-dihydropyrimidine (0.5 g, 1.1 mmol) (obtained in example 48) by refluxing with morpholine (0.25 g, 2.8 mmol) in ethanol (10 ml) according to the procedure described in example 45 (0.4, yield 78.4%, mp 255-258° C., purity 97.95% by HPLC). $^1$H-NMR (DMSO):δ 3.21 (s, 3H), 3.63-3.7 (m, 8H), 7.09-7.14 (m, 2H), 7.19 (s, 1H, D$_2$O exchangeable), 7.42-7.46 (m, 2H), 7.58-7.6 (d, 2H), 7.85-7.87 (d, 2H), 8.06 (s, 1H, D$_2$O exchangeable). IR (KBr) cm$^{-1}$: 3404, 3326, 3167, 1656 (—C=O). MS m/z:473.2 (M$^+$).

EXAMPLE 51

Synthesis of 5-carboxamido-1-(3,4-dimethylphenyl)-4-(methylsulfonyl)-2-[4-(methylsulfonyl)phenyl]-6-oxo-1,6-dihydropyrimidine

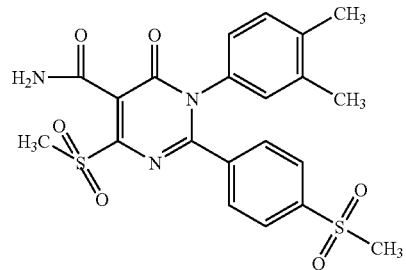

The title compound was prepared from 5-cyano-1-(3,4-dimethylphenyl)-4-(methylthio)-2-[4-(methylthio)phenyl]-6-oxo-1,6-dihydropyrimidine (5.0 g, 12 mmol, prepared according to the procedure described in example 10) according to the procedure described in example 44 (1.8 g, yield 30%, mp 245-248° C., purity 97.88% by HPLC). $^1$H-NMR (DMSO):δ 2.15-2.17 (d, 6H), 3.2 (s, 3H), 3.28 (s, 3H), 6.99-7 (s, 1H), 7.11-7.13 (d, 2H), 7.65-7.67 (d, 2H), 7.72 (s, 1H), 7.77 (s, 1H), 7.83-7.85 (d, 2H). IR (KBr) cm$^{-1}$: 3391, 3158, 2922, 1693, 1683 (—C=O). MS m/z:476.1 (M$^+$).

EXAMPLE 52

Synthesis of 5-cyano-2-(4-fluorophenyl)-4-hydroxy-1-[4-(methylsulfonyl)phenyl]-6-oxo-1,6-dihydropyrimidine

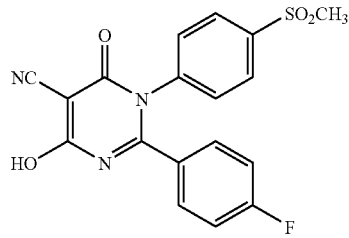

The title compound was prepared from 5-cyano-2-(4-fluorophenyl)-1-[4-(methylthio)phenyl]-4-(methylthio)-6-oxo-1,6-dihydropyrimidine (5 g, 13 mmol, prepared according to the procedure disclosed in example 2) in acetic acid (20 ml) and then added hydrogen peroxide (20 ml) under stirring. The reaction was refluxed at 80° C. for 3 hrs and filtered the solid and followed according to the procedure described in example 44 (1.2 g, yield 24%, mp >285° C., purity 93.63% by HPLC). $^1$H-NMR (DMSO):δ 3.21 (s, 3H), 3.38 (bs, 1H, D$_2$O exchangeable), 7.18-7.23 (m, 2H), 7.48-7.52 (m, 2H), 7.60-7.62 (d, 2H), 7.88-7.9 (d, 2H). IR (KBr) cm$^{-1}$: 3428, 3283, 2922, 2211 (—CN), 1701, 1668, 1606 (—C=O). MS m/z:386.1 (M$^+$).

EXAMPLE 53

Synthesis of 5-cyano-1-(3,4-dimethylphenyl)-4-hydroxy-2-[4-(methylsulfonyl)phenyl]-6-oxo-1,6-dihydropyrimidine

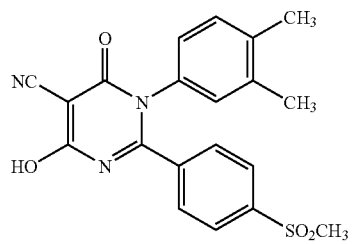

The title compound was prepared from 5-cyano-1-(3,4-dimethylphenyl)-4-(methylthio)-2-[4-(methylthio)phenyl]-6-oxo-1,6-dihydropyrimidine (1.0 g, 2.5 mmol) (prepared according to the procedure for example 10) in acetic acid (5 ml) and then added hydrogen peroxide (5 ml) under stirring and followed according to the procedure described in example 52 (0.2 g, yield 17%, mp >285° C., purity 89.27% by HPLC). $^1$H-NMR (DMSO):δ 2.1-2.12 (d, 6H), 3.19 (s, 3H), 3.36 (bs, 1H, D$_2$O exchangeable), 7.0-7.11 (m, 3H), 7.72-7.74 (d, 2H), 7.86-7.88 (d, 2H). IR (KBr) cm$^{-1}$: 3417, 3138, 3082, 2999, 2920, 2206, 1701 (—C=O). MS m/z: 396.1 (M$^+$).

EXAMPLE 54

Synthesis of 5-cyano-4-(methylamino)-1-(4-methylphenyl)-2-[4-(methylthio)phenyl]-6-oxo-1,6-dihydropyrimidine

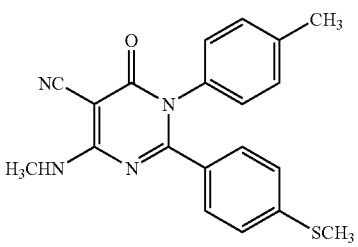

A suspension of 5-cyano-1-(4-methylphenyl)-4-(methylthio)-2-[4-(methylthio)phenyl]-6-oxo-1,6-dihydropyrimidine (2 g, 5.3 mmol) (prepared according to the procedure disclosed in example 6) in ethanol (20 ml) with methylamine (0.33 g, 10.6 mmol) was refluxed for 2 hr. Then the reaction mass poured on to ice and the resulted solid filtered, washed thoroughly with water. The resulted solid purified by column chromatography using ethyl acetate and hexane mixture as eluent to yield title compound (0.55 g, yield 25.5%, mp 268-271° C., purity 97.34% by HPLC). $^1$H-NMR (CDCl$_3$):δ 2.32 (s, 3H), 2.43 (s, 3H), 2.95 (d, 3H), 5.8 (s, 1H, D$_2$O exchangeable), 6.95-6.97 (d, 3H), 7.02-7.04 (d, 1H), 7.11-7.13 (d, 1H), 7.22-7.26 (m, 3H). IR (KBr) cm$^{-1}$: 3294, 2919, 2205 (—CN), 1666 (—C=O). MS m/z: 363.1 (M$^+$).

EXAMPLE 55

Synthesis of 5-cyano-1-(3,4-dimethylphenyl)-4-(methylamino)-2-[4-(methylthio)phenyl]-6-oxo-1,6-dihydropyrimidine

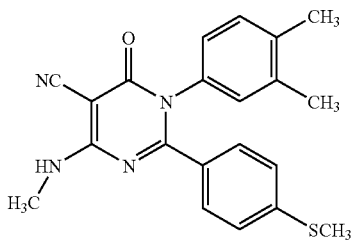

A suspension of 5-cyano-1-(3,4-dimethylphenyl)-4-(methylthio)-2-[4-(methylthio)phenyl]-6-oxo-1,6-dihydropyrimidine (1 g, 2.5 mmol) (prepared according to example 10) in ethanol (10 ml) with methylamine (0.16 g, 5 mmol) was refluxed for 3 hr. Then the reaction mass poured on to ice and the resulted solid filtered, washed thoroughly with water. The solid thus obtained was purified by column chromatography using ethyl acetate and hexane mixture as eluent to yield title compound (0.36 g, yield 38%, mp 199-205° C., purity 98.72% by HPLC). $^1$H-NMR (CDCl$_3$):δ 2.19 (s, 3H), 2.22 (s, 3H), 2.44 (s, 3H), 3.17-3.18 (d, 3H), 5.73 (s, 1H, D$_2$O exchangeable) 6.75-6.77 (d, 2H), 6.90 (s, 1H), 7.02-7.06 (m, 3H), 7.24-7.26 (d, 1H). IR (KBr) cm$^{-1}$: 3280, 2920, 2207 (—CN), 1661 (—C=O). MS m/z:377.2 (M$^+$).

EXAMPLE 56

Synthesis of 5-cyano-2-(4-fluorophenyl)-4-(methylamino)-1-[4-(methylthio)phenyl]-6-oxo-1,6-dihydropyrimidine

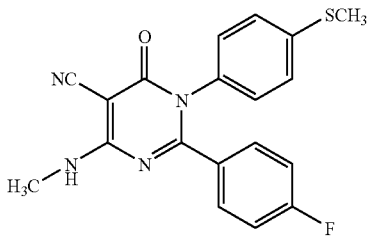

The title compound was prepared from 5-cyano-2-(4-fluorophenyl)-1-[4-(methylthio)phenyl]-4-(methylthio)-6-oxo-1,6-dihydropyrimidine (1 g, 2.6 mmol, prepared according to the procedure disclosed in example 2) in ethanol (10 ml) with methylamine (0.16 g, 5 mmol) was refluxed for 2 hr. Then the reaction mass poured on to ice and the resulted solid filtered, washed thoroughly with water. The solid thus obtained was purified by column chromatography using ethyl acetate and hexane mixture as eluent to yield title compound (0.4 g, yield 42%, mp 219-222° C. purity 95.3% by HPLC). $^1$H-NMR (CDCl$_3$):δ 2.45 (s, 3H), 3.17-3.18 (d, 3H), 6.0 (s, 1H, NH, D$_2$O exchangeable), 6.91-6.99 (m, 4H), 7.14-7.16 (d, 2H), 7.31-7.34 (m, 2H). IR (KBr) cm$^{-1}$: 3279, 2981, 2931, 2208, 1736, 1651, 1604 (—C=O). MS m/z: 367.1 (M$^+$).

EXAMPLE 57

Synthesis of 5-cyano-1-(3,4-dimethylphenyl)-4-(methylthio)-2-phenyl-6-oxo-1,6-dihydropyrimidine

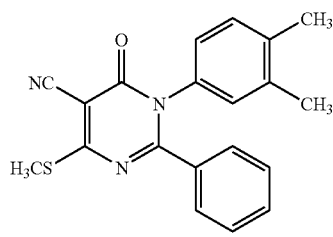

The title compound was prepared from ethyl 2-cyano-3,3-dimethylthioacrylate (4.8 g, 22 mmol) and N-(3,4-dimethylphenyl)benzenecarboximidamide (5 g, 22 mmol) (obtained according to preparation 41) according to the procedure described in example 9 (6.55 g, yield 81.3%, purity 99.7% by HPLC). $^1$H-NMR (CDCl$_3$):δ 2.18-2.21 (d, 6H), 2.66 (s, 3H), 6.75-6.78 (d, 1H), 6.89-6.9 (d, 1H), 7.05-7.07 (d, 1H), 7.22-7.26 (m, 2H), 7.33-7.36 (m, 3H). MS m/z:348.2 (M$^+$).

EXAMPLE 58

Synthesis of 4-[5-cyano-1-(3,4-dimethylphenyl)-4-(methylthio)-6-oxo-1,6-dihydropyrimidin-2-yl]benzenesulfonyl chloride

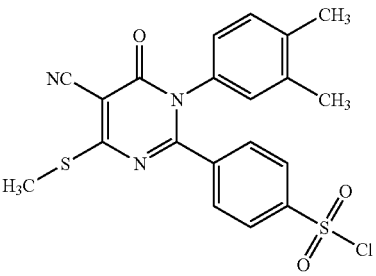

A solution of 5-cyano-1-(3,4-dimethylphenyl)-4-(methylthio)-2-phenyl-6-oxo-1,6-dihydropyrimidine (3 g, 8.6 mmol) (obtained according to example 57) in chlorosulfonic acid (50.37 g, 432 mmol) was stirred at 0° C. for 2 hr and at ambient temperature for 24 hr and then poured onto ice and extracted with chloroform. The collected chloroform layer was dried over anhydrous Na$_2$SO$_4$ and concentrated in vacuo to yield crude compound, which was further purified by column chromatography using chloroform:methanol mixture as eluent to yield title compound (0.5 g, yield 13%). $^1$H-NMR (CDCl$_3$):δ 2.37 (s, 3H), 2.65 (s, 3H), 2.68 (s, 3H), 7.26-7.55 (m, 7H). MS m/z:446.1 (M$^+$).

EXAMPLE 59

Synthesis of 4-[5-cyano-2-(4-ethoxyphenyl)-4-(methylthio)-6-oxopyrimidin-1(6H)-yl]benzenesulfonyl chloride

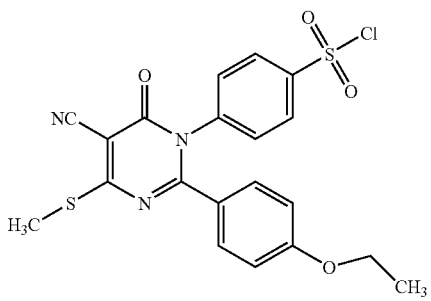

A solution of 5-cyano-2-(4-ethoxyphenyl)-1-phenyl-4-(methylthio)-6-oxo-1,6-dihydropyrimidine (1 g, 2.7 mmol) in chlorosulfonic acid (6.14 g, 53 mmol) and chloroform (30 ml) was refluxed 1 hr and then poured on to ice. The chloroform layer was collected and dried over Na$_2$SO$_4$ and concentrated under vacuo to yield title compound (0.8 g, yield 62.9%). $^1$H-NMR (DMSO):δ 1.21-1.24 (t, 3H), 2.6 (s, 3H), 3.94-3.99 (q, 2H), 6.7-6.72 (d, 1H), 7.03-7.05 (q, 1H), 7.33-7.39 (m, 5H), 8.04-8.05 (1H). MS m/z:463.7 (M$^+$).

EXAMPLE 60

Synthesis of 4-[5-cyano-1-(4-methylphenyl)-4-(methylthio)-6-oxo-1,6-dihydropyrimidin-2-yl]benzenesulfonamide

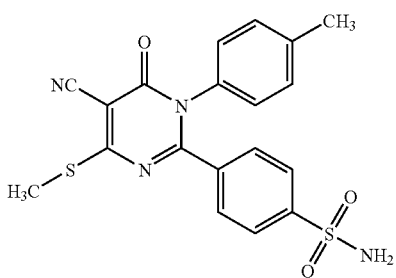

A solution of 5-cyano-1-(4-methylphenyl)-4-(methylthio)-6-oxo-2-phenyl-1,6-dihydropyrimidine (5 g, 15 mmol) (prepared according to the procedure described for example 23) in chlorosulfonic acid (87.7 g, 756 mmol) was stirred at ambient temperature for 20 hr. The resulted reaction mass was treated with dichloromethane (200 ml) and washed with water, dried over Na$_2$SO$_4$. The ammonia gas purged through the resulted dichloromethane layer for 1 hr slowly at 0-10° C. The dichloromethane layer was again washed with water, dried over Na$_2$SO$_4$. The solvent removed under vacuo and the solid obtained was purified by column chromatography using chloroform and methanol mixture as eluent to yield the title compound (0.25 g, yield 4.0%, purity 99.7% by HPLC). $^1$H-NMR (DMSO):δ 2.51 (s, 3H), 2.64 (s, 3H), 7.26-7.41 (m, 7H), 7.49 (s, 2H, D$_2$O exchangeable), 7.93-7.94 (d, 1H). MS m/z: 413 (M$^+$).

Described below are the examples of pharmacological assays used for finding out the efficacy of the compounds of the present invention wherein their protocols and results are provided.

Rat Carrageenan Paw Edema Test

The carrageenan paw edema test is performed as described by Winter et al (Proc. Soc. Exp. Biol. Med, 111, 544, 1962). Male Wistar rats are selected and the body weights are equivalent within each group. The rats are fasted for eighteen hours with free access to water. The rats are dosed orally with the test compound suspended in vehicle containing 0.5% methylcellulose. The control rats are administered the vehicle alone. After an hour, the rats are injected with 0.1 ml of 1% Carrageenan solution in 0.9% saline into the sub-plantar surface of the right hind paw. Paw volume is measured using water plethysmograph before and after 3 hours of carrageenan injection. The average of foot swelling in drug treated animals is compared with that of control animals. Anti-inflammatory activity is expressed as the percentage inhibition of edema compared with control group [Arzneim-Forsch/Drug Res., 43(I), 1, 44-50,1993; Ottemess and Bliven, Laboratory Models for Testing NSAIDs, In Non-Steroidal Anti-Inflammatory Drugs, (J. Lombardino, ed. 1985)]. In order to evaluate their role on the ulcer formation, the animals are sacrificed and the stomach is taken out and flushed with 1% formalin. The stomach is opened along the greater curvature. The haemorrhagic puncta and sulci are identified microscopically and images are captured. The stomach lesions are calculated. Representative results of rat paw edema inhibition and inicidence of ulceration are shown in Table I.

TABLE I

| Example No. | Rat Paw Edema model % inhibition (mg/kg body weight) | | Gastroulcerogenic potential (% incidence of ulceration) |
| --- | --- | --- | --- |
| 1 | 10 | 29.0 | 75 |
| 2 | 10 | 39.0 | 25 |
| 4 | 10 | 38.5 | 25 |
| 5 | 10 | 13.3 | 37.5 |
| 6 | 10 | 40.2 | 25 |
| 7 | 10 | 28.1 | 25 |
| 9 | 10 | 37.2 | 0 |
| 10 | 10 | 68.6 | 0 |
| 11 | 5 | 63.8 | ND |
| 12 | 5 | 41.2 | ND |

ND—Not done/determined

In Vivo Evaluation of Cyclooxygenase-2 (COX-2) Inhibition Activity

The compounds of this invention exhibited in vitro inhibition of COX-2. The COX-2 inhibition activities of the compounds illustrated in the examples are determined by the following method.

Human Whole Blood Assay

Human whole blood provides a protein and cell rich milieu appropriate for the study of biochemical efficacy of anti-inflammatory compounds such as selective COX-2 inhibitors. Studies have shown that normal human blood does not contain COX-2 enzyme. This is correlating with the observation that COX-2 inhibitors have no effect on prostaglandin E$_2$ (PGE2) production in normal blood. These inhibitors are active only after incubation of human blood with lipopolysaccharide (LPS), which induces COX-2 production in the blood.

Method

Fresh blood is collected in tubes containing potassium EDTA by vein puncture from make volunteers. The subjects should have no apparent inflammatory conditions and not taken NSAIDs for at least 7 days prior to blood collection. Blood is treated with aspirin in vitro (10 μg/ml, at time zero) to inactivate COX-1, and then with LPS (10 μg/ml) along with test agents or vehicle. The blood is incubated for 24 h at 37° C., after which the tubes are centrifuged, the plasma is separated and stored at −80° C. (J. Pharmacol. Exp. Ther, 271, 1705, 1994; Proc. Natl. Acad. Sci. USA., 96, 7563, 1999). The plasma is assayed for PGE2 using Cayman ELISA kit as per the procedure outlined by the manufacturer (Cayman Chemicals, Ann Arbor, USA). Representative results of COX-2 inhibition are shown in Table II.

TABLE II

| Example No. | Conc. (μM) | COX-2 Inhibition (%) |
| --- | --- | --- |
| 1 | 10 | 12.96 |
| 2 | 1 | 53.38 |
| 4 | 10 | 50.07 |
| 5 | 1 | 40.55 |
| 6 | 1 | 55.71 |
| 7 | 0.25 | 31.67 |
| 8 | 1 | 40.06 |
| 10 | 0.1 | 62.76 |
| 11 | 0.25 | 31.15 |
| 12 | 0.25 | 36.51 |
| 13 | 0.25 | 33.47 |
| 14 | 0.25 | 28.19 |
| 17 | 0.25 | 16.23 |
| 20 | 0.25 | 7.67 |
| 21 | 0.25 | 7.79 |
| 30 | 1 | 14.91 |
| 42 | 0.1 | 37.57 |
| 43 | 1 | 27.48 |
| 54 | 0.25 | 72.12 |
| 55 | 1 | 8.2 |

Tumor Necrosis Factor Alpha (TNF-α)

This assay determines the effect of test compounds on the production of TNF-α in human whole blood. TNF-α assay is carried out as described by Armin hatzelmann and Christian Schudt (J Pharm Exp Ther 297, 261, 2001). Compounds are tested for their ability to inhibit the activity of TNF-α in human whole blood. The test compounds are pre-incubated for 15 minutes at 37° C. and then stimulated with Lipopolysaccharide (*Salmonella abortus* equi, 1 μg/ml) for 4 h at 37° C. in 5% $CO_2$. The levels of TNF-α are estimated using Enzyme linked Immunosorbent assay performed in a 96 well format as per the procedure of the manufacturer (Cayman Chemical, Ann Arbor, USA). Representative results of TNF-α inhibition are shown in Table III

TABLE III

| Example No. | Conc. (μM) | TNF-α Inhibition (%) |
| --- | --- | --- |
| 1 | 0.1 | 56.87 |
| 6 | 1 | 28.83 |
| 10 | 10 | 26.37 |
| 11 | 0.25 | 63.84 |
| 12 | 0.25 | 27.18 |
| 15 | 0.1 | 18.41 |
| 16 | 10 | 59.82 |
| 17 | 10 | 47.42 |

TABLE III-continued

| Example No. | Conc. (μM) | TNF-α Inhibition (%) |
| --- | --- | --- |
| 18 | 1 | 35.66 |
| 20 | 1 | 61.41 |
| 21 | 1 | 46.57 |
| 22 | 1 | 62.68 |
| 25 | 1 | 59.56 |
| 26 | 1 | 30.63 |
| 31 | 0.1 | 20.20 |
| 32 | 0.1 | 17.90 |
| 42 | 0.1 | 49.6 |
| 43 | 1 | 36.35 |
| 54 | 1 | 15.6 |
| 55 | 1 | 54.40 |

Interleukin-6 (IL-6)

This assay determines the effect of test compounds on the production of IL-6 from human whole blood. Compounds are tested for their ability to downregulate the production of IL-6 in activated whole blood. The test compounds are pre-incubated for 15 minutes at 37° C. and then stimulated with Lipopolysaccharide (*Salmonella abortus* equi, 1 μg/ml) for 4 h at 37° C. in 5% $CO_2$. The levels of Interleukin-6 are estimated using Enzyme linked Immunosorbent assay performed in a 96 well format as per the procedure of the manufacturer (Cayman Chemical, Ann Arbor, USA). Representative results of IL-6 inhibition are shown in Table IV.

TABLE IV

| Example No. | Conc. (μM) | IL-6 Inhibition (%) |
| --- | --- | --- |
| 1 | 0.1 | 52.76 |
| 2 | 0.25 | 44.96 |
| 3 | 0.25 | 11.32 |
| 4 | 0.25 | 48.36 |
| 5 | 0.25 | 51.05 |
| 6 | 0.25 | 41.37 |
| 7 | 1 | 37.12 |
| 8 | 1 | 69.38 |
| 9 | 0.25 | 31.14 |
| 10 | 1 | 48.65 |
| 11 | 0.25 | 70.77 |
| 12 | 0.25 | 28.69 |
| 17 | 0.25 | 16.23 |
| 18 | 100 | 44.77 |
| 21 | 1 | 17.30 |
| 22 | 1 | 66.34 |
| 41 | 10 | 21.87 |
| 42 | 0.1 | 59.69 |
| 43 | 0.25 | 10.39 |
| 54 | 1 | 15.54 |

Inhibitory Action on Adjuvant Arthritis

Compounds are assayed for their activity on rat adjuvant induced arthritis according to Theisen-Popp et al., (Agents Actions, 42, 50-55, 1994). Six to seven weeks old, Wistar rats are weighed, marked and assigned to groups [a negative control group in which arthritis is not induced (non-adjuvant control), a vehicle-treated arthritis control group, test substance treated arthritis group]. Adjuvant induced arthritis is induced by an injection of *Mycobacterium butyricum* (Difco) suspended in liquid paraffin into the sub-plantar region of the right hind paw (J. Pharmacol. Exp. Ther., 284, 714, 1998). Body weight, paw volumes are measured at various days (0, 14, 21) for all the groups. The test compound or vehicle is administered orally beginning post injection of adjuvant and continued for 21 days. On day 21, body weight and paw volume of both right and left hind paw, spleen, and thymus weights are determined. In addition, the radiographs of both hind paws are taken to assess the tibio-tarsal joint integrity. Hind limb below the stifle joint is removed and fixed in 1% formalin saline. At the end of the experiment, plasma samples are analysed for cytokines, interleukins and prostaglandins. The presence or absence of lesions in the stomach is also observed.

Two-factor ('treatment' and 'time') Analysis of Variance with repeated measures on 'time' is applied to the percentage (%) changes for body weight and foot volumes. A post hoc Dunnett's test is conducted to compare the effect of treatments to vehicle. A one-way Analysis of Variance is applied to the thymus and spleen weights followed by the Dunnett's test to compare the effect of treatments to vehicle. Dose-response curves for percentage inhibition in foot volumes on days 4, 14 and 21 are fitted by a 4-parameter logistic function using a nonlinear Least Squares' regression. $ID_{50}$ is defined as the dose corresponding to a 50% reduction from the vehicle and is derived by interpolation from the fitted 4-parameter equation.

DTP Human Tumor Cell Line Screen

Methodology of the In Vitro Cancer Screen

The three cell lines, one-dose prescreen carried out which identifies a large proportion of the compounds that would be inactive in multi-dose 60 cell line screening. The current assay utilizes a 384 well plate format and fluorescent staining technologies resulting in greater screening capacity for testing of synthetic samples.

Cell Lines

The cell lines of the cancer-screening panel are grown in RPMI 1640 medium containing 5% fetal bovine serum and 2 mM L-glutamine. For a typical screening experiment, cells are inoculated into 96 well microtiter plates in 100 µL. After cell inoculation, the microtiter plates are incubated at 37° C., 5% $CO_2$, 95% air and 100% relative humidity for 24 h prior to addition of experimental drugs. The cells are plated a densities of 5000 cells/well (MCF7), 1000 cells/well (NC1—H460), and 7500 cells/well (SF-268) to allow for varying doubling time of the cell lines. Each plate contains all three cell lines, a series of dilutions of standard agents, total kill wells and appropriate controls. Plates are incubated under standard conditions for 24 hours prior to addition of experimental compounds or extracts.

Addition of Experimental Agents (Pure Compounds)

Experimental compounds are solubilized in dimethyl sulfoxide (DMSO) at 400-times the desired maximum test concentration (maximum final DMSO concentration of 0.25%) and stored frozen. Compounds are then diluted with complete media with 0.1% gentamicin sulfate (5 µl of test sample in 100% DMSO is added to 565 µl of complete medium). 20 µl of this solution is then dispensed into test wells containing 50 µl of cell suspension to yield a test concentration of 1.00E-04M.

Two standard drugs, meaning that their activities against the cell lines are well documented, are tested against each cell line: NSC 19893 (5-FU) and NSC 123127 (Adriamycin).

Endpoint Measurement

After compound addition, plates are incubated at standard conditions for 48 hours, 10 µl/well Alamar Blue is added and the plates are incubated for an additional 4 hours. Fluorescence is measured using an excitation wavelength of 530 nm and an emission wavelength of 590 nm.

Calculation of Percent Test Cell Growth/Control (Untreated) Cell Growth (T/C)

Percent growth is calculated on a plate-by-plate basis for test wells relative to control wells. Percent Growth is expressed as the ratio of fluorescence of the test well to the average fluorescence of the control wells x 100. The results are shown in table V.

TABLE V

| Example No. | Conc. (µM) | Percentage growth | | |
|---|---|---|---|---|
| | | Lung NCI-H460 | Breast MCF-7 | CNS SF-268 |
| 3 | 100 | 30 | 82 | 90 |
| 8 | 100 | 51 | 77 | 89 |
| 16 | 100 | 95 | 90 | ND |
| 18 | 100 | 98 | 89 | 86 |
| 21 | 100 | 92 | 84 | 91 |
| 22 | 50 | 80 | 83 | ND |
| 26 | 100 | 79 | 74 | 99 |
| 27 | 100 | 14 | 23 | 51 |
| 28 | 100 | 20 | 48 | 63 |
| 29 | 100 | 23 | 80 | 92 |
| 30 | 100 | 27 | 38 | 86 |
| 41 | 100 | 86 | 85 | 89 |
| 43 | 100 | 79 | 68 | ND |
| 49 | 50 | 72 | 79 | 88 |
| 50 | 50 | 94 | 92 | 97 |
| 56 | 50 | 54 | 63 | 87 |

The invention claimed is:

1. A pyrimidone of the formula (I)

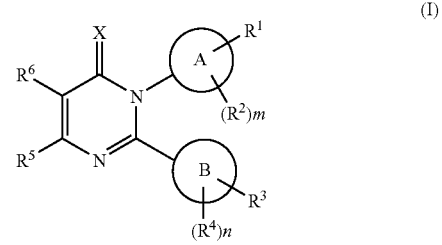

or its pharmaceutically acceptable salt, wherein X represents oxygen, sulfur or NR, wherein R represents hydrogen, hydroxyl, acyl, alkyl, alkoxy, aryl, amino, hydroxylamino, alkylamino, arylamino, acylamino, alkoxyamino group; the rings represented by A and B are selected from aryl or heteroaryl; $R^1$ and $R^3$ may be same or different and independently represent hydrogen, $SR^7$, $S(O)_pR^8$; $R^2$ and $R^4$ may be same or different and independently represent halogen, hydroxyl, nitro, cyano, azido, nitroso, amino, formyl, alkyl, haloalkyl, acyl, alkoxy, monoalkylamino, dialkylamino, acylamino, alkoxycarbonyl, $SR^7$, $S(O)_pR^8$, alkoxyalkyl groups or carboxylic acids; $R^5$ and $R^6$ may be same or different and independently represent halogen, hydroxyl, nitro, cyano, azido, nitroso, amino, formyl, aralkyl, haloalkyl, acyl, alkoxy, aryloxy, aralkoxy, heteroaryl, heterocyclyl, monoalkylamino, dialkylamino, acylamino, alkoxycarbonyl, $SR^7$, $S(O)_pR^8$, alkoxyalkyl groups or $COR^9$; $R^7$ represents hydrogen, alkyl or aryl; $R^8$ represents halogen, alkyl, amino, acylamino, arylamino or aryl group; $R^9$ represents hydrogen, hydroxyl, amino, halogen, alkyl, alkoxy, aryloxy, monoalkylamino, dialkylamino, acylamino, arylamino, groups; m is an integer and is in the range of 1 to 4; n is an integer and is in the range of 1 to 4; p represents an integer of 1 or 2.

2. The pyrimidone of the formula (I) as claimed in claim 1, wherein the ring systems represented by a and B are selected from phenyl, naphthyl, pyridyl, thienyl, furyl, pyrrolyl, oxazolyl, thiazolyl, imidazolyl, pyrazolyl, oxadiazolyl, thiadiazolyl, tetrazolyl, pyrimidinyl, benzopyranyl, benzofuranyl, benzimidazolyl, benzoxazolyl, benzothiazolyl, benzopyrrolyl, benzoxadiazolyl, benzothiadiazolyl, quinolinyl, isoquinolinyl, benzothienyl, benzofuranyl or indolyl.

3. A pyrimidone selected from:
   5-Cyano-2-(4-chlorophenyl)-4-(methylthio)-1-[4-(methylthio)phenyl]-6-oxo-1,6-dihydropyrimidine;
   5-Cyano-2-(4-fluorophenyl)-4-(methylthio)-1-[4-(methylthio)phenyl]-6-oxo-1,6-dihydropyrimidine;
   5-Cyano-2-phenyl-4-(methylthio)-1-[4-(methylthio)phenyl]-6-oxo-1,6-dihydropyrimidine;
   5-Cyano-2-(trifluoromethylphenyl)-4-(methylthio)-1-[4-(methylthio)phenyl]-6-oxo-1,6-dihydropyrimidine;
   5-Cyano-2-[(4-methylthio)phenyl]-4-(methylthio)-1-[4-fluorophenyl]-6-oxo-1,6-dihydropyrimidine;
   5-Cyano-1-(4-methylphenyl)-4-(methylthio)-2-[4-(methylthio)phenyl]-6-oxo-1,6-dihydropyrimidine;
   5-Cyano-2-[(4-methylsulphonyl)phenyl]-4-(methylthio)-1-[4-methylphenyl]-6-oxo-1,6-dihydropyrimidine;
   5-Carboxy-2-[(4-methylthio)phenyl]-4-(methylthio)-1-[4-methylphenyl]-6-oxo-1,6-dihydropyrimidine;
   5-Cyano-1-(4-isopropylphenyl)-4-(methylthio)-2-[4-(methylthio)phenyl]-6-oxo-1,6-dihydropyrimidine;
   5-Cyano-1-(3,4-dimethylphenyl)-4-(methylthio)-2-[4-(methylthio)phenyl]-6-oxo-1,6-dihydropyrimidine;
   5-Cyano-1-(4-isopropylphenyl)-2-[4-(methylsulfonyl)phenyl]-4-(methylthio)-6-oxo-1,6-dihydropyrimidine;
   5-Cyano-1-(3,4-dimethylphenyl)-2-[4-(methylsulfonyl)phenyl]-4-(methylthio)-6-oxo-1,6-dihydropyrimidine;
   5-Cyano-1-(3,4,5-trimethoxyphenyl)-4-(methylthio)-2-[4-(methylthio)phenyl]-6-oxo-1,6-dihydropyrimidine;
   5-Cyano-1-(4-ethylphenyl)-4-(methylthio)-2-[4-(methylthio)phenyl]-6-oxo-1,6-dihydropyrimidine;
   1-(4-Bromophenyl)-5-cyano-4-(methylthio)-2-[4-(methylthio)phenyl]-6-oxo-1,6-dihydropyrimidine;
   5-Cyano-1-(4-methoxyphenyl)-4-(methylthio)-2-[4-(methylthio)phenyl]-6-oxo-1,6-dihydropyrimidine;
   5-Cyano-1-(4-fluorophenyl)-4-(methylthio)-2-phenyl-6-oxo-1,6-dihydropyrimidine;
   1-(4-Chlorophenyl)-5-cyano-4-(methylthio)-2-[4-(methylthio)phenyl]-6-oxo-1,6-dihydropyrimidine;
   5-Cyano-1-(2,4-dimethylphenyl)-4-(methylthio)-2-[4-(methylthio)phenyl]-6-oxo-1,6-dihydropyrimidine;
   5-Cyano-2-(4-methylphenyl)-4-(methylthio)-1-[4-(methylthio)phenyl]-6-oxo-1,6-dihydropyrimidine;
   5-Cyano-1-(4-methoxyphenyl)-4-(methylthio)-2-[4-(methylthio)phenyl]-6-oxo-1,6-dihydropyrimidine;
   1-(4-tert-Butylphenyl)-5-cyano-4-(methylthio)-2-[4-(methylthio)phenyl]-6-oxo-1,6-dihydropyrimidine;
   5-Cyano-1-(4-methylphenyl)-4-(methylthio)-6-oxo-2-phenyl-1,6-dihydropyrimidine;
   1-(4-n-Butylphenyl)-5-cyano-4-(methylthio)-2-[4-(methylthio)phenyl]-6-oxo-1,6-dihydropyrimidine;
   5-Cyano-1-(4-fluorophenyl)-4-(methylthio)-6-oxo-2-pyridin-4-yl-1,6-dihydropyrimidine;
   5-Cyano-1-(4-fluorophenyl)-4-(methylthio)-6-oxo-2-pyridin-3-yl-1,6-dihydropyrimidine;
   5-Cyano-4-(methylthio)-1-[4-(methylthio)phenyl]-6-oxo-2-pyridin-3-yl-1,6-dihydropyrimidine;
   5-Cyano-4-(methylthio)-1-[4-(methylthio)phenyl]-6-oxo-2-pyridin-4-yl-1,6-dihydropyrimidine;
   5-Cyano-1-(4-fluorophenyl)-4-(methylthio)-6-oxo-2-pyridin-2-yl-1,6-dihydropyrimidine;
   5-Cyano-4-(methylthio)-1-[4-(methylthio)phenyl]-6-oxo-2-pyridin-2-yl-1,6-dihydropyrimidine;
   5-Cyano-4-(methylthio)-1-(4-methoxyphenyl)-6-oxo-2-pyridin-2-yl-1,6- dihydropyrimidine;
   5-Cyano-4-(methylthio)-1-(3,4-dimethylphenyl)-6-oxo-2-pyridin-2-yl-1,6-dihydropyrimidine;
   5-Cyano-4-(methylthio)-1-(4-ethylphenyl)-6-oxo-2-pyridin-2-yl-1,6-dihydropyrimidine;
   5-Cyano-4-(methylthio)-1-(4-methylphenyl)-6-oxo-2-pyridin-2-yl-1,6-dihydropyrimidine;
   5-Cyano-4-(methylthio)-1-(4-ethoxyphenyl)-6-oxo-2-pyridin-4-yl-1,6-dihydropyrimidine;
   5-Cyano-4-(methylthio)-1-(4-methylphenyl)-6-oxo-2-pyridin-4-yl-1,6-dihydropyrimidine;
   5-Cyano-4-(methylthio)-1-(4-isopropylphenyl)-6-oxo-2-pyridin-4-yl-1,6-dihydropyrimidine;
   5-Cyano-4-(methylthio)-1-(4-ethylphenyl)-6-oxo-2-pyridin-3-yl-1,6-dihydropyrimidine;
   5-Cyano-4-(methylthio)-1-(3,4-dimethylphenyl)-6-oxo-2-pyridin-3-yl-1,6-dihydropyrimidine;
   5-Cyano-4-(methylthio)-1-(4-methoxyphenyl)-6-oxo-1-pyridin-3-yl-1,6-dihydropyrimidine;
   Ethyl 1-(4-methylphenyl)-4-(methylthio)-2-[4-(methylthio)phenyl]-6-oxo-1,6-dihydropyrimidine-5-carboxylate;
   Ethyl 1-(4-fluorophenyl)-4-(methylthio)-2-[4-(methylthio)phenyl]-6-oxo-1,6-dihydropyrimidine-5-carboxylate;
   Ethyl 2-(4-fluorophenyl)-4-(methylthio)-1-[4-(methylthio)phenyl]-6-oxo-1,6-dihydropyrimidine-5-carboxylate;
   5-Carboxamido-1-(4-methylphenyl)-4-(methylsulfonyl)-2-[4-(methylsulfonyl)phenyl]-6-oxo-1,6-dihydropyrimidine;
   5-Carboxamido-1-(4-methylphenyl)-2-[4-(methylsulfonyl)phenyl]-6-oxo-4-piperazin-1-yl-1,6-dihydropyrimidine;
   5-Carboxamido-4-(methylamino)-1-(4-methylphenyl)-2-[4-(methylsulfonyl)phenyl]-6-oxo-1,6-dihydropyrimidine;
   5-Carboxamido-1-(4-methylphenyl)-2-[4-(methylsulfonyl)phenyl]-4-morpholin-4-yl-6-oxo-1,6-dihydropyrimidine;
   5-Carboxamido-2-(4-fluorophenyl)-4-(methylsulfonyl)-1-[4-(methylsulfonyl)phenyl]-6-oxo-1,6-dihydropyrimidine;
   5-Carboxamido-2-(4-fluorophenyl)-4-(methylamino)-1-[4-(methylsulfonyl)phenyl]-6-oxo-1,6-dihydropyrimidine;
   5-Carboxamido-2-(4-fluorophenyl)-1-[4-(methylsulfonyl)phenyl]-4-morpholin-4-yl-6-oxo-1,6-dihydropyrimidine;
   5-Carboxamido-1-(3,4-dimethylphenyl)-4-(methylsulfonyl)-2-[4-(methylsulfonyl)phenyl]-6-oxo-1,6-dihydropyrimidine;
   5-Cyano-2-(4-fluorophenyl)-4-hydroxy-1-[4-(methylsulfonyl)phenyl]-6-oxo-1,6-dihydropyrimidine;
   5-Cyano-1-(3,4-dimethylphenyl)-4-hydroxy-2-[4-(methylsulfonyl)phenyl]-6-oxo-1,6-dihydropyrimidine;
   5-Cyano-4-(methylamino)-1-(4-methylphenyl)-2-[4-(methylthio)phenyl]-6-oxo-1,6-dihydropyrimidine;
   5-Cyano-1-(3,4-dimethylphenyl)-4-(methylamino)-2-[4-(methylthio)-phenyl]-6-oxo-1,6-dihydropyrimidine;
   5-Cyano-2-(4-fluorophenyl)-4-(methylamino)-1-[4-(methylthio)phenyl]-6-oxo-1,6-dihydropyrimidine;

4-[5-Cyano-1-(3,4-dimethylphenyl)-4-(methylthio)-6-oxo-1,6-dihydropyrimidin-2-yl]benzenesulfonyl chloride;

4-[5-Cyano-2-(4-ethoxyphenyl)-4-(methylthio)-6-oxopyrimidin-1(6H)-yl]benzenesulfonyl chlorid;

4-[5-Cyano-1-(4-methylphenyl)-4-(methylthio)-6-oxo-1,6-dihydropyrimidin-2-yl]benzenesulfonamide;

N-({4-[5-Cyano-1-(4-methylphenyl)-4-(methylthio)-6-oxo-1,6-dihydropyrimidin-2-yl]phenyl}sulfonyl)acetamide;

N-({4-[5-Cyano-1-(3,4-dimethylphenyl)-4-(methylthio)-6-oxo-1,6-dihydropyrimidin-2-yl]phenyl}sulfonyl)acetamide;

N-({4-[5-Cyano-1-(4-methylphenyl)-4-(methylthio)-6-oxo-1,6-dihydropyrimidin-2-yl]phenyl}sulfonyl)-2,2,2-trifluoroacetamide;

N-({4-[5-Cyano-1-(3,4-dimethylphenyl)-4-(methylthio)-6-oxo-1,6-dihydropyrimidin-2-yl]phenyl}sulfonyl)-2,2,2-trifluoroacetamide;

N-({4-[5-Cyano-1-(4-methylphenyl)-4-(methylthio)-6-oxo-1,6-dihydropyrimidin-2-yl]phenyl}sulfonyl)benzamide and N-({4-[5-Cyano-1-(3,4-dimethylphenyl)-4-(methylthio)-6-oxo-1,6-dihydropyrimidin-2-yl]phenyl}sulfonyl)benzamide.

4. A process for the preparation of a pyrimidone of the formula (I)

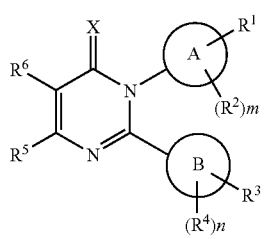

(I)

or its pharmaceutically acceptable salt, wherein X represents oxygen, sulfur or NR, wherein R represents hydrogen, hydroxyl, acyl, alkyl, alkoxy, aryl, amino, hydroxylamino, alkylamino, arylamino, acylamino, alkoxyamino group; the rings represented by A and B are selected from aryl or hereroaryl; $r^1$ and $R^3$ may be same or different and independently represent hydrogen, $SR^7$, $S(O)_p R^8$; $R^2$ and $R^4$ may be same or different and independently represent halogen, hydroxyl, nitro, cyano, azido, nitroso, amino, formyl, alkyl, haloalkyl, acyl, alkoxy, monoalkylamino, dialkylamino, acylamino, alkoxycarbonyl, $SR^7$, $S(O)_p R^8$, alkoxyalkyl groups or carboxylic acids; $R^5$ and $R^6$ may be same or different and independently represent halogen, hydroxyl, nitro, cyano, azido, nitroso, amino, formyl, aralkyl, haloalkyl, acyl, alkoxy, aryloxy, aralkoxy, heteroaryl, heterocyclyl, monoalkylamino, dialkylamino, acylamino, alkoxycarbonyl, $SR^7$, $S(O)_p R^8$, alkoxyalkyl groups or $COR^9$; $R^7$ represents hydrogen, alkyl or aryl; $R^8$ represents halogen, alkyl, amino, acylamino, arylamino or aryl group; $R^9$ represents hydrogen, hydroxyl, amino, halogen, alkyl, alkoxy, aryloxy, monoalkylamino, dialkylamino, acylamino, arylamino, groups; m is an integer and is in the range of 1 to 4; n is an integer and is in the range of 1 to 4; p represents an integer of 1 or 2; which comprises reacting a compound of the formula (Ia)

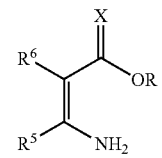

(Ia)

where R represent $(C_1-C_3)$ alkyl group, X, $R^5$ and $R^6$ are as defined above, with a compound of the formula (Ib)

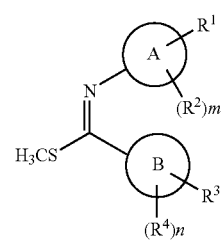

(Ib)

wherein all symbols are as defined above, to produce a compound of formula (I).

5. A process for the preparation of a pyrimidone of the formula (I)

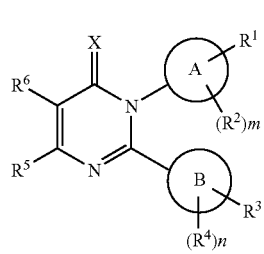

(I)

or its pharmaceutically acceptable salt, wherein X represents oxygen, sulfur or NR, wherein R represents hydrogen, hydroxyl, acyl, alkyl, alkoxy, aryl, amino, hydroxylamino, alkylamino, arylamino, acylamino, alkoxyamino group; the rings represented by A and B are selected from aryl or heteroaryl; $R^1$ and $R^3$ may be same or different and independently represent hydrogen, $SR^7$, $S(O)_p R^8$; $R^2$ and $R^4$ may be same or different and independently represent halogen, hydroxyl, nitro, cyano, azido, nitroso, amino, formyl, alkyl, haloalkyl, acyl, alkoxy, monoalkylamino, dialkylamino, acylamino, alkoxycarbonyl, $SR^7$, $S(O)_p R^8$, alkoxyalkyl groups or carboxylic acids; $R^5$ and $R^6$ may be same or different and independently represent halogen, hydroxyl, nitro, cyano, azido, nitroso, amino, formyl, aralkyl, haloalkyl, acyl, alkoxy, aryloxy, aralkoxy, heteroaryl, heterocyclyl, monoalkylamino, dialkylamino, acylamino, alkoxycarbonyl, $SR^7$, $S(O)_p R^8$, alkoxyalkyl groups or $COR^9$; $R^7$ represents hydrogen, alkyl or aryl; $R^8$ represents halogen, alkyl, amino, acylamino, arylamino or aryl group; $R^9$ represents hydrogen, hydroxyl, amino, halogen, alkyl, alkoxy, aryloxy, monoalkylamino, dialkylamino, acylamino, arylamino, groups; m is an integer and is in the range of 1 to 4; n is an integer and is in the range of 1 to 4; p represents an integer of 1 or 2; with a proviso that when $R^1$ represents hydrogen $R^2$ is not hydrogen, which comprises reacting a compound of the formula (Ic)

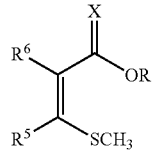
(Ic)

where R represent $(C_1-C_3)$ alkyl group and all other symbols are as defined above, with a compound of the formula (Id)

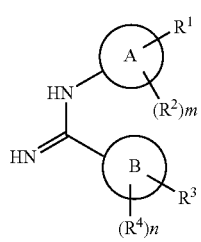
(Id)

wherein all symbols are as defined above, to produce a compound of formula (I).

6. A process for the conversion of the pyrimidone of the formula (I) as claimed in claim 1,

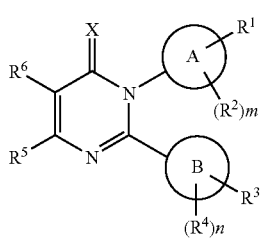
(I)

wherein any one of the groups $R^1$ and $R^3$ represent $SR^7$, wherein $R^7$ represents alkyl or aryl and all other symbols are as defined in claim 1, to pyrimidones of the formula (I) wherein any one of the groups $R^1$ and $R^3$ represent $S(O)_pR^8$, where p represents 1 or 2 and $R^8$ represents alkyl or aryl, and all other symbols are as defined above, using an oxidizing agent.

7. A process for the conversion of the pyrimidone of the formula (I) as claimed in claim 1,

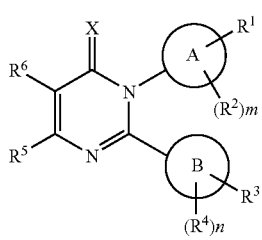
(I)

wherein either of the groups $R^1$ or $R^3$ represent $S(O)_pR^8$, wherein $R^8$ represents amino group and p represents an integer of 1 or 2 and all other symbols are as defined in claim 1, which comprises reacting compound of formula (Ie)

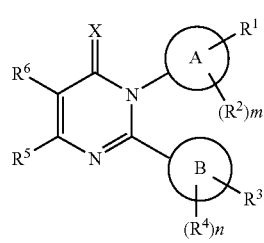
(Ie)

wherein $R^1$ or $R^3$ represents hydrogen and all other symbols are as defined in claim 1, with chlorosulfonic acid and ammonia.

8. A pharmaceutical composition which comprises a compound of formula (I)

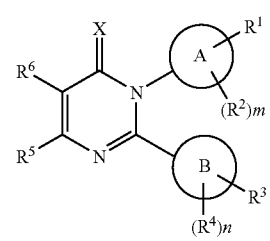
(I)

as defined in claim 1 and a pharmaceutically acceptable carrier, diluent, excipient or solvate.

9. A pharmaceutical composition as claimed in claim 8, in the form of a tablet, capsule, powder, syrup, aerosol, solution or suspension.

10. A pharmaceutical composition which comprises a compound as claimed in claim 3 and a pharmaceutically acceptable carrier, diluent, excipient or solvate.

11. A pharmaceutical composition as claimed in claim 10, in the form of a tablet, capsule, powder, syrup, aerosol, solution or suspension.

12. A method of treating a condition selected from the group consisting of rheumatoid arthritis; lung cancer, breast cancer and central nervous system cancer; inflammatory bowel disease; and psoriasis comprising administering the compound of formula (I) as claimed in claim 1 in a pharmaceutically effective amount to a subject afflicted with one or more of the foregoing conditions and in need of treatment.

13. A method of treating a condition selected from the group consisting of rheumatoid arthritis; lung cancer, breast cancer and central nervous system cancer; inflammatory bowel disease; and psoriasis comprising administering the compound as claimed in claim 3 in a pharmaceutically effective amount to a subject afflicted with one or more of the foregoing conditions and in need of treatment.

14. A method of treating a condition selected from the group consisting of rheumatoid arthritis, and psoriasis comprising administering the composition as claimed in claim 8 in a pharmaceutically effective amount to a subject afflicted with one or more of the foregoing conditions in need of treatment.

* * * * *